United States Patent
Dirienzo

(10) Patent No.: US 8,920,809 B2
(45) Date of Patent: Dec. 30, 2014

(54) CHIMERA COMPRISING BACTERIAL CYTOTOXIN AND METHODS OF USING THE SAME

(75) Inventor: Joseph M. Dirienzo, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 360 days.

(21) Appl. No.: 12/858,312

(22) Filed: Aug. 17, 2010

(65) Prior Publication Data

US 2012/0027785 A1 Feb. 2, 2012

Related U.S. Application Data

(63) Continuation-in-part of application No. PCT/US2009/038740, filed on Mar. 30, 2009.

(60) Provisional application No. 61/064,862, filed on Mar. 31, 2008.

(51) Int. Cl.
| | | |
|---|---|---|
| *A61K 39/00* | (2006.01) | |
| *A61K 39/02* | (2006.01) | |
| *A61K 39/38* | (2006.01) | |
| *A61K 39/116* | (2006.01) | |
| *A61K 31/7088* | (2006.01) | |
| *C07K 16/12* | (2006.01) | |
| *C12N 9/22* | (2006.01) | |
| *C12N 5/095* | (2010.01) | |
| *C07K 14/195* | (2006.01) | |
| *C12N 15/62* | (2006.01) | |
| *A61K 38/00* | (2006.01) | |

(52) U.S. Cl.
CPC ......... *A61K 31/7088* (2013.01); *C07K 16/1203* (2013.01); *C07K 2319/21* (2013.01); *C12N 9/22* (2013.01); *C07K 2319/00* (2013.01); *C12N 5/0695* (2013.01); *A61K 38/00* (2013.01); *C07K 14/195* (2013.01); *C12N 2500/72* (2013.01); *C12N 15/62* (2013.01)
USPC .................. 424/192.1; 424/184.1; 424/185.1; 424/190.1; 424/203.1; 424/234.1; 424/236.1; 424/278.1; 424/282.1; 514/1.1; 514/16.1; 514/19.2; 514/19.3; 514/19.8; 514/21.2

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 5,279,823 A * | 1/1994 | Frenz et al. | 424/94.61 |

FOREIGN PATENT DOCUMENTS

WO  WO 01/34205 A2 *  5/2001  ............. A61K 47/48

OTHER PUBLICATIONS

Linardou et al., (Int. J. Cancer. 2000. vol. 86:561-569).*
Mayer (Infect. Immun. 1999. vol. 67:1227-1237).*
Nishikubo et al., "An N-terminal segment of the active component of the bacterial genotoxin cytolethal distending toxin B (CDTB) directs CDTB into the nucleus", J Biol Chem. 2003, 12;278(50):50671-81.
Pan et al., "Mutational analysis of human DNase I at the DNA binding interface: implications for DNA recognition, catalysis and metal ion dependence", Protein Science 7: 628-636, 1998.
Field et al., "Purification of a RAS-Responsive Adenylyl Cyclase Complex from *Saccharomyces cerevisiae* by Use of an Epitope Addition Method" Mol. Cell. Biol., 8: 2159-2165 (1988).
Evan et al., "Isolation of Monoclonal Antibodies Specific for Human c-myc Proto-Oncogene Product", Molecular and Cellular Biology, 5: 3610-3616 (1985).
Skinner et al., "Use of the Glu-Glu-Phe C-terminal Epitope for Rapid Purification of the Catalytic Domain of Normal and Mutanrta s GTPase-activating Proteins" J. Biol. Chem., 266:15163-15166 (1991).
Lutz-Freyermuth et al., "Quantitative determination that one of two potential RNA-binding domains of the a protein component of the U1 small nuclear ribonucleoprotein complex binds with high affinity to stem-loop II of U1 RNA" Proc. Natl. Acad. Sci. USA, 87: 6393-6397 (1990).
LaRochelle et al. "Specific receptor detection by a function keratinocyte growth factor-immunoglobulin chimera", J. Cell Biol., 139(2): 357-66 (1995).
Heidaran et al., "Beta PDGFR-IgG chimera demonstrates that human Beta PDGFR-Ig-like domains 1 to 3 are sufficient for high affinity PDGF BB binding", FASEB J., 9(1): 140-5 (1995).
Cheon et al., "High-affinity binding sites for related fibroblast growth factor ligands reside within different receptor immunoglobulin-like domains" PNAS USA, 91(3): 989-93 (1994).
Buskin and Hauschka, "Identification of a Myocyte Nuclear Factor That Binds to the Muscle-Specific Enhancer of the Mouse Muscle Creatine Kinase Gene" (1989) *Mol. Cell Biol.* 9:2627.
Mar and Ordahl, "A conserved CATTCCT motif is required for skeletal muscle-specific activity of the cardiac troponin T gene promoter" (1988) *Proc. Natl. Acad. Sci. USA.* 85:6404.
Jho Sh et al, "Negative Response Elements in Keratin Genes Mediate Transcriptional Repression and the Cross-talk among Nuclear Receptors" (2001). J. Biol Chem.

(Continued)

*Primary Examiner* — Ja'na Hines
(74) *Attorney, Agent, or Firm* — Mark S. Cohen; Pearl Cohen; Zedek Latzer Baratz LLP

(57) ABSTRACT

This invention provides, a recombinant polypeptide encoding a chimera. The chimera includes a DNase I fragment or a homologue thereof and a Cdt fragment or a homologue thereof. Further, the invention provides methods, utilizing the recombinant polypeptide encoding the chimera, such as a method for inhibiting the proliferation of a neoplastic cell, a method for treating a neoplastic disease in a human subject, a method for inhibiting or suppressing a neoplastic disease in a human subject, and a method for reducing the symptoms associated with a neoplastic disease in a human subject.

13 Claims, 24 Drawing Sheets

(56) References Cited

OTHER PUBLICATIONS

Figure 6A:
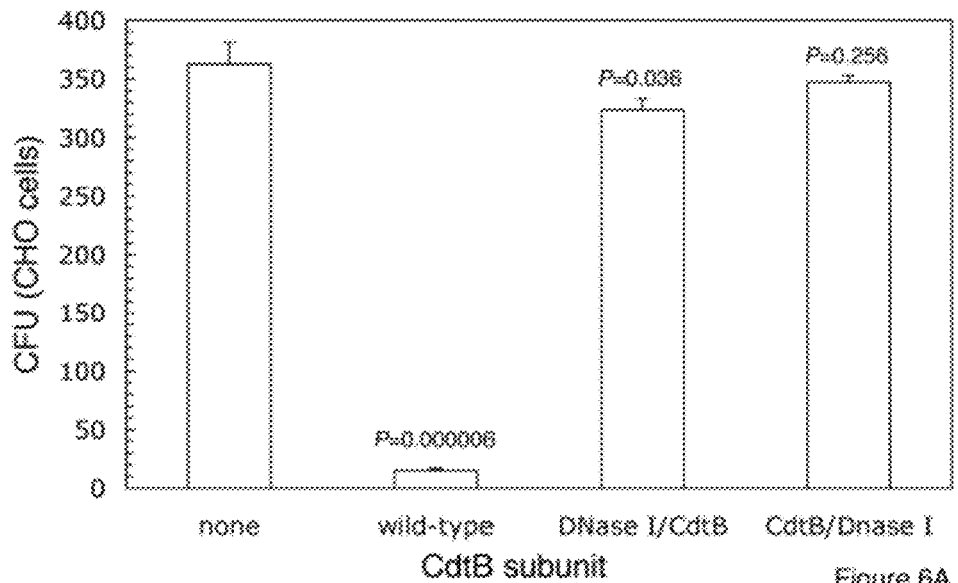

Mader, S. and White, J. H. "A steroid-inducible promoter for the controlled overexpression of cloned genes in eukaryotic cells" (1993) *Proc. Natl. Acad. Sci. USA* 90:5603-5607.

Manome, Y. et al. "Coinduction of c-jun Gene Expression and Internucleosomal DNA Fragmentation by Ionizing Radiation" (1993) *Biochemistry* 32:10607-10613.

Datta, R. et al. "Ionizing radiation activates transcription of the EGRI gene via CArG elements" (1992) Proc. *Natl. Acad. Sci. USA* 89:1014-10153.

Shak, et al., "Recombinant human DNase I reduces the viscosity of cystic fibrosis sputum", Proc. Nat. Acad. Sci. 87:9188-9192 (1990).

Hubbard, et al., "A preliminary study of aerosolized recombinant human deoxyribonuclease I in the treatment of cystic fibrosis", New. Engl. J. Med. 326:812-815 (1992).

Fuchs, et al., "Effect of aerosolized recombinant human DNase on exacerbations of respiratory symptoms and on pulmonary function in patients with cystic fibrosis", New Engl. J. Med. 331:637-642 (1994).

Langer, "New methods of drug delivery", Science, vol. 249, p. 1527-1533.

Treat et al., In Liposomes in the Therapy of Infectious Disease and Cancer, Lopez-Berestein and Fidler (eds.), Liss, New York, pp. 353-365 (1989).

Lopez-Berestein et al., In Liposomes in the Therapy of Infectious Disease and Cancer, Lopez-Berestein and Fidler (eds.), Liss, New York, pp. 317-327 (1989).

Sefton, "Implantable pumps", CRC Crit. Ref. Biomed. Eng. 14:201 (1987).

Buchwald et al., "Long-term, continuous intravenous heparin administration by an implantable infusion pump in ambulatory patients with recurrent venous thrombosis", Surgery 1980, p. 507.

Saudek et al., "A preliminary trial of the programmable implantable medication system for insulin delivery", The New England Journal of Medicine, vol. 321, No. 9, p. 574-579, 1989.

Goodson et al., Medical applications of controlled release, vol. 2, p. 115-138, 1984.

Abuchowski et al., "Immunosuppresive properties and circulating life of *Achromobacter* glutaminase-asparaginase covalently attached to polyethylene glycol in man", Cancer Treat Rep. 1981, 65(11-12): 1077-1081.

Katre et al., "Chemical modification of recombinant interleukin 2 by polyethylene glycol increases its potency in the murine Meth a sarcoma model" Proc. Natl. Acad. Sci., vol. 84, pp. 1487-1491, 1987.

Cao et al., "Role of Intrachain Disulfides in the Activities of the CdtA and CdtC Subunits of the Cytolethal Distending Toxin of *Actinobacillus actinomycetemcomitans*" Infection and Immunity, Sep. 2006, p. 4990-5002.

Elwell & Dreyfus, "DNase I homologous residues in CdtB are critical for cytolethal distending toxin-mediated cell cycle arrest", Molecular Microbiology, 2000, 37(4): 952-963.

Ulmer et al, "Engineering actin-resistant human DNase I for treatment of cystic fibrosis", PNAS, vol. 93, pp. 8225-8229 (1996).

Nešić et al., "Assembly and function of a bacterial genotoxin", Nature vol. 429, pp. 429-433, 2004.

Mao X, DiRienzo JM (2002). "Functional studies of the recombinant subunits of a cytolethal distending holotoxin", Cell Microbiol 4:245-455.

Cao L, Volgina A, Huang, CM, Korostoff J, DiRienzo JM (2005). "Characterization of point mutations in the cdtA gene of the cytolethal distending toxin of *Actinobacillus actinomycetemcomitans*", Mol Microbiol 58:1303-1321.

Cao L, Bandelac G, Volgina A, Korostoff J, DiRienzo JM (2008) "Role of aromatic amino acids in receptor binding activity and subunit assembly of the cytolethal distending toxin of *Aggregatibacter actinomycetemcomitans*", Infect Immun 76:2812-2821.

Yamada et al., "Variation of Loop Sequence Alters Stability of Cytolethal Distending Toxin (CDT): Crystal Structure of CDT from *Actinobacillus actinomycetemcomitans*" Protein Science (2006) 15(2).

Pettersen et al., "UCSF Chimera—A Visualization System for Exploratory Research and Analysis", Journal of Computational Chemistry, vol. 25, No. 13, pp. 1605-1612, 2004.

Price, "The essential role of CA2+ in the activity of bovine pancreatic deoxyribonuclease", The Journal of Biological Chemistry 1975, vol. 250, No. 6, , pp. 1981-1186.

Allen, C. M. "Animal models of oral candidiasis", 1994. Oral Surg Oral Med Oral Pathol 78:216-221.

Samaranayake et al., "Experimental Oral Candidiasis in Animal Models" 2001. Clin Microbiol Rev 14:398-429.

Kanno et al., "Resistance of Human Periodontal Ligament Fibroblasts to the Cytolethal Distending Toxin of *Actinobacillus actinomycetemcomitans*" J Periodontol, 2005, vol. 76 • No. 7, pp. 1188-1200.

Elwell et al., 2001.

NCBI submission AAC70898m Mar. 9, 1999, retrieved from the internet: URL: http://www.ncbi.nlm.nih.gov/protein/3786346.

Hu et al., "Comparitive structure-function analysis of cytolethal distending toxins", Proteins 2006, vol. 62, No. 2, pp. 421-434.

Shenker et al., "Induction of cell cycle arrest in lymphocytes by *Actinobacillus actinomycetemcomitans* cytolethal distending toxin requires three subunits for maximum activity", Journal of Immunology, 2005, vol. 174, No. 4, pp. 2228-2234.

\* cited by examiner

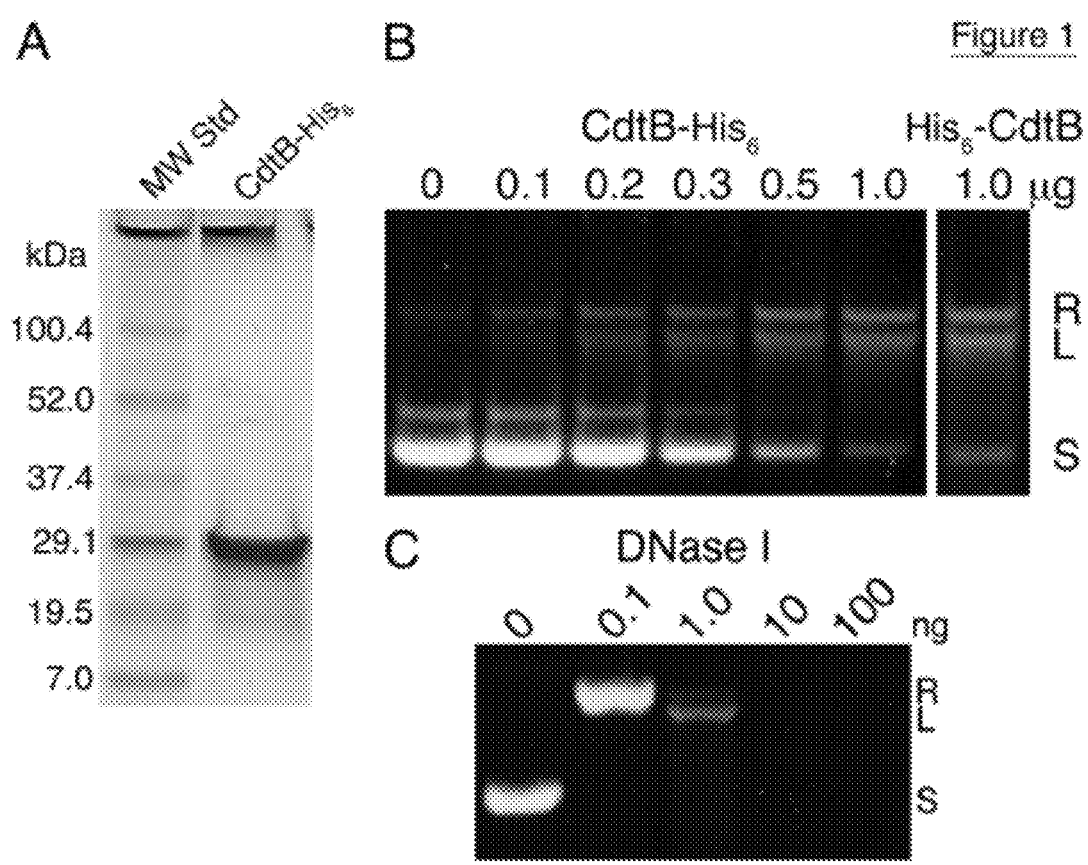

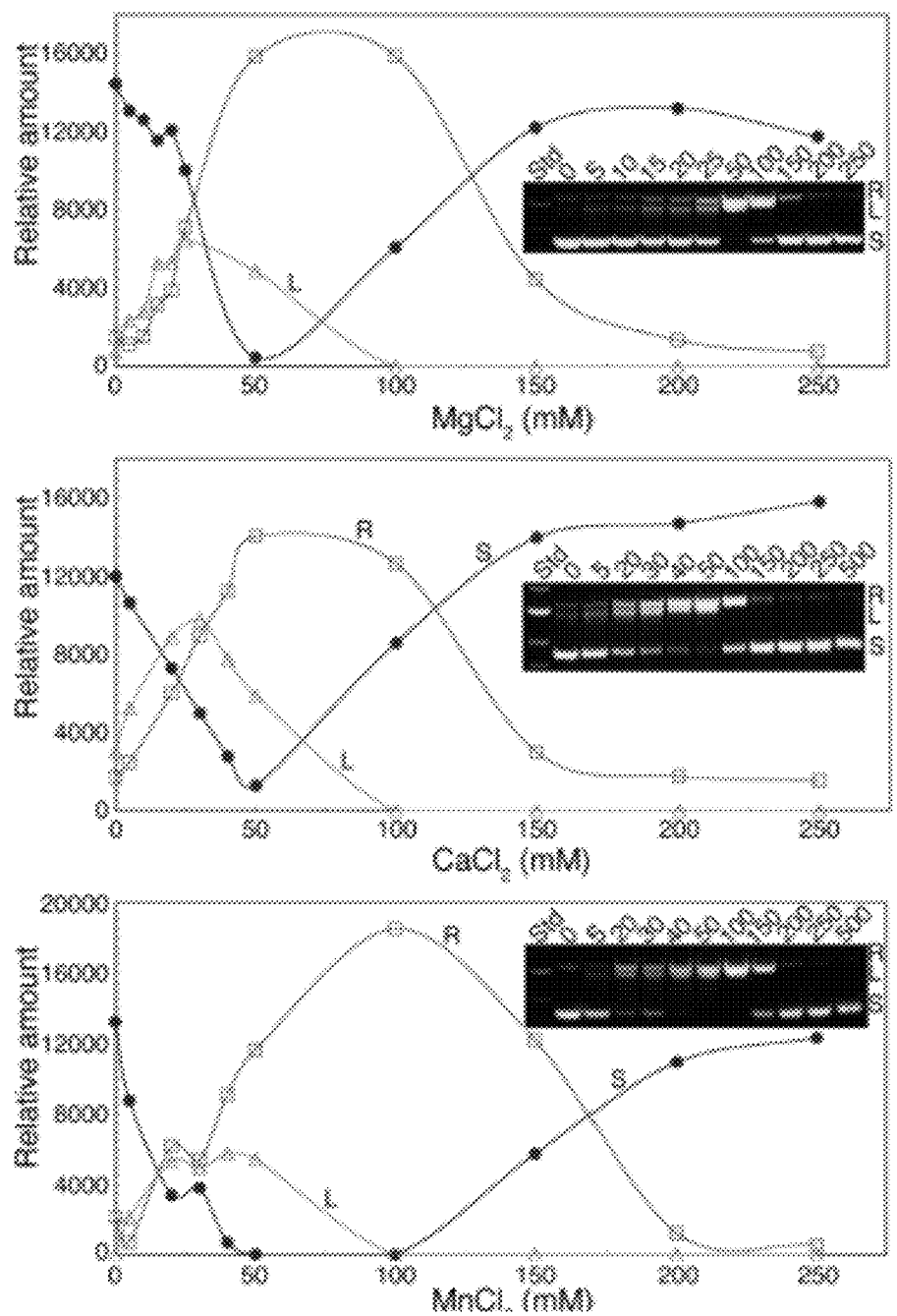

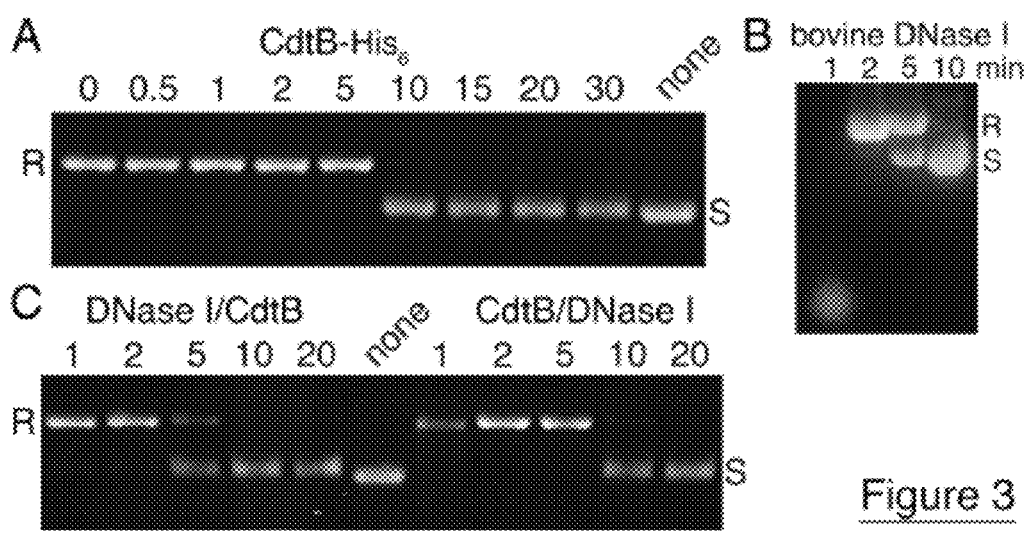
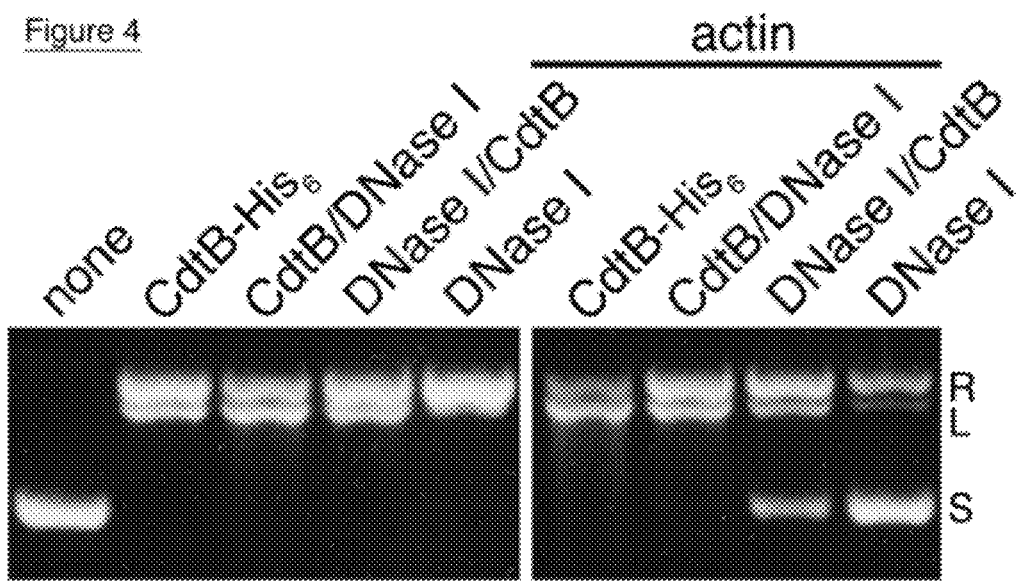

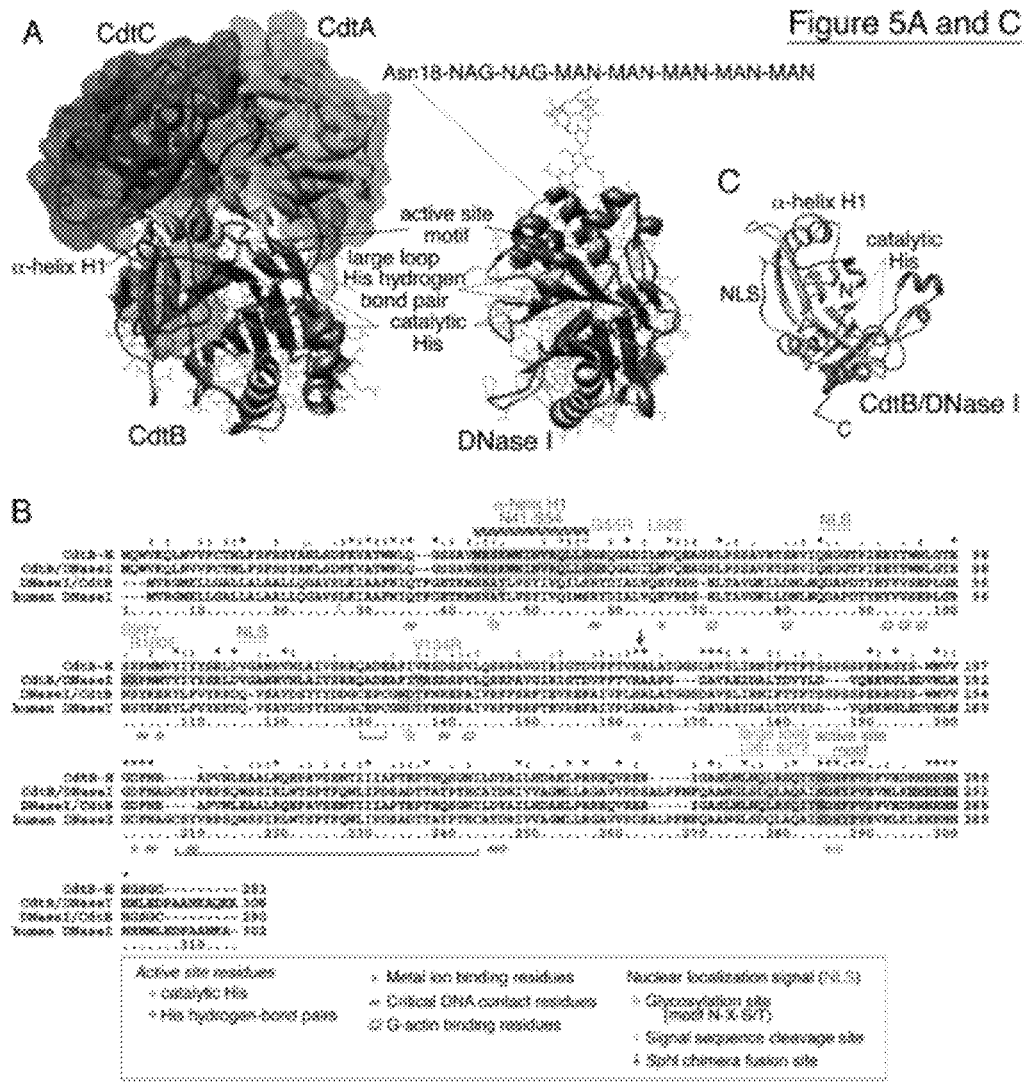

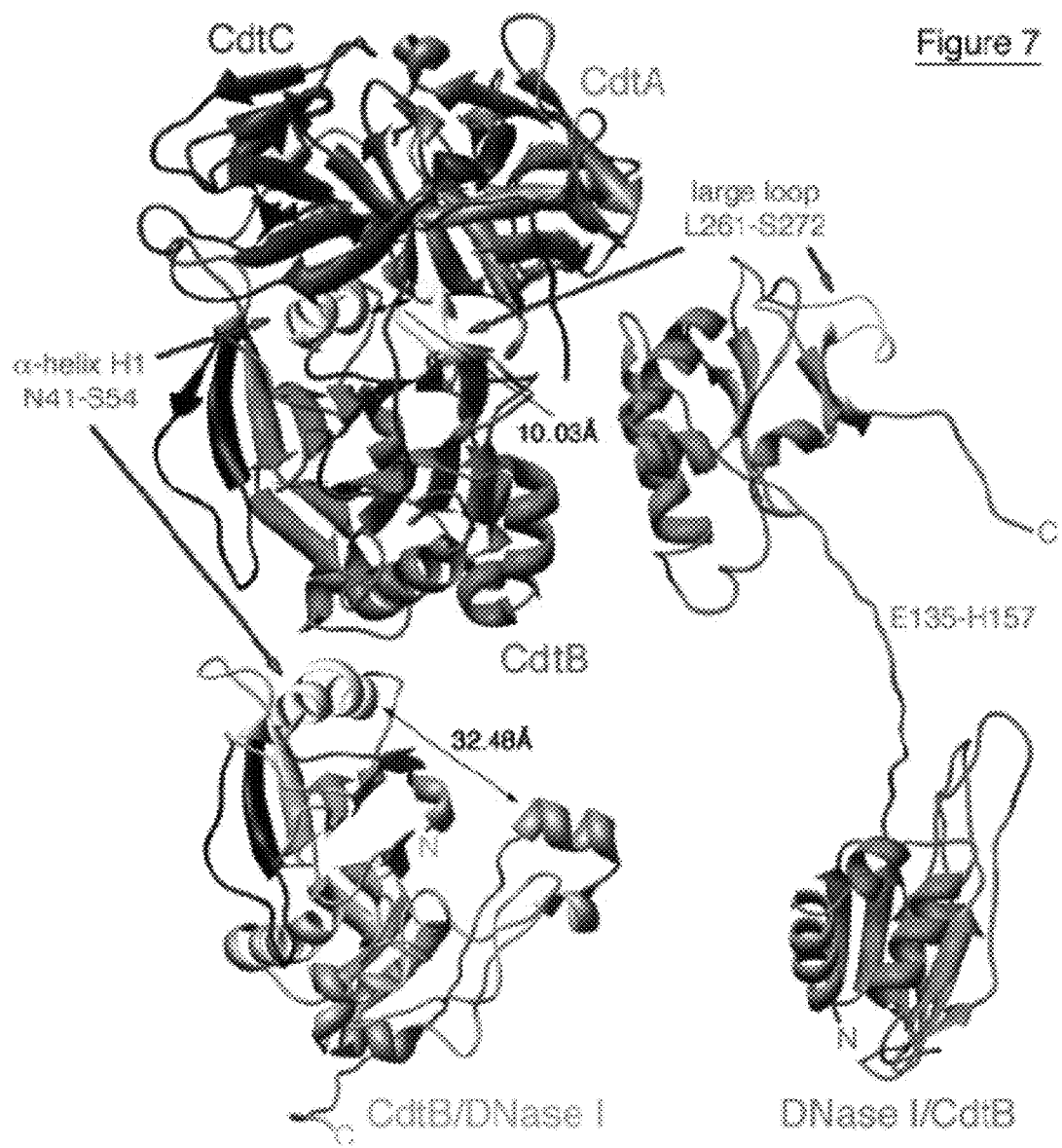

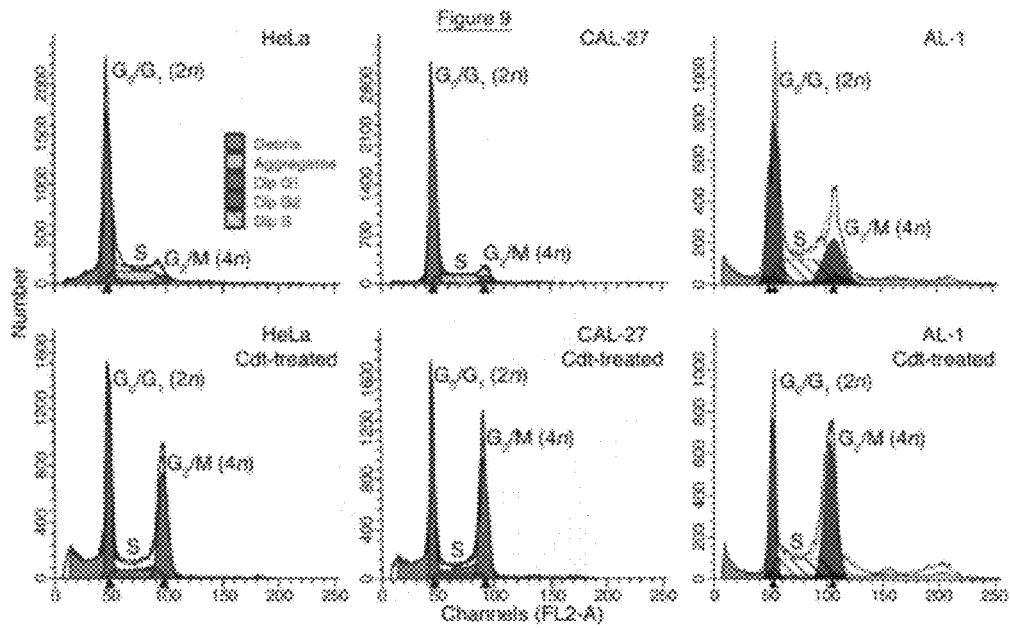
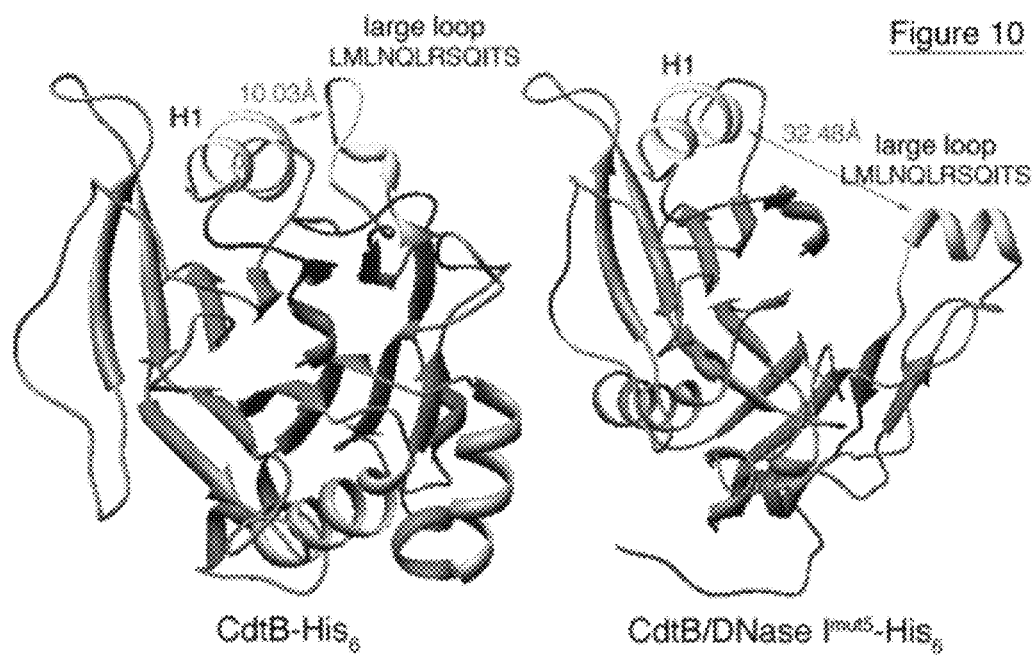

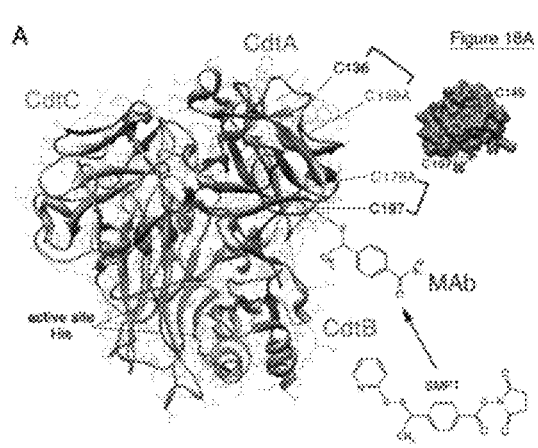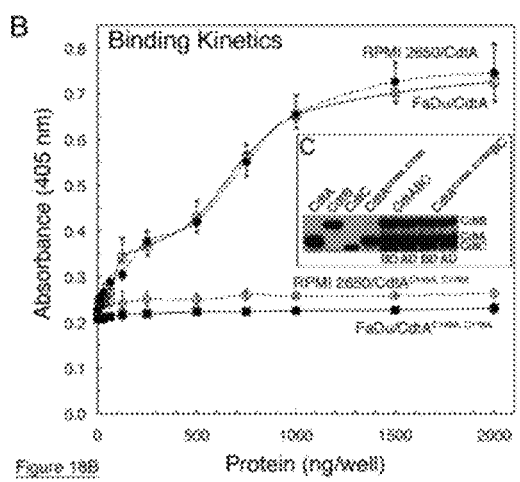

SEQUENCE LISTING

<160> NUMBER OF SEQ ID NOS: 59

<210> SEQ ID NO 1
<211> LENGTH: 918
<212> TYPE: DNA
<213> ORGANISM: Homo sapiens

<400> SEQUENCE: 1

```
ttgtacaaaa aagcaggctt ggaaggagtt cgaaccatga ggggcatgaa gctgctgggg      60
gcgctgctgg cactggcggc cctactgcag ggggccgtgt ccctgaagat cgcagccttc     120
aacatccaga catttgggga gaccaagatg tccaatgcca ccctcgtcag ctacattgtg     180
cagatcctga gccgctatga catcgccctg gtccaggagg tcagagacag ccacctgact     240
gccgtgggga agctgctgga caacctcaat caggatgcac cagacaccta tcactacgtg     300
gtcagtgagc cactgggacg gaacagctat aaggagcgct acctgttcgt gtacaggcct     360
gaccaggtgt ctgcggtgga cagctactac tacgatgatg gctgcgagcc ctgcgggaac     420
gacaccttca accgagagcc agccattgtc aggttcttct cccggttcac agaggtcagg     480
gagtttgcca ttgttcccct gcatgcggcc ccgggggacg cagtatccga gatcgacgct     540
ctctatgacg tctacctgga tgtccaagag aaatggggct tggaggacgt catgttgatg     600
ggcgacttca atgcgggctg cagctatgtg agaccctccc agtggtcatc catccgcctg     660
tggacaagcc ccaccttcca gtggctgatc cccgacagcg ctgacaccac agctacaccc     720
acgcactgtg cctatgacag gatcgtggtt gcagggatgc tgctccgagg cgccgttgtt     780
cccgactcgg ctcttcccct taacttccag gctgccaatg gcctgagtga ccaactggcc     840
caagccatca gtgaccacta tccagtggag gtgatgctga agtagctcga gtgcggccgc     900
aacccagctt tcttgtac                                                    918
```

<210> SEQ ID NO 2
<211> LENGTH: 849
<212> TYPE: DNA
<213> ORGANISM: Homo sapiens

<400> SEQUENCE: 2

```
atgaggggca tgaagctgct ggggggcgctg ctggcactgg cggccctact gcaggggggcc      60
gtgtccctga agatcgcagc cttcaacatc cagacatttg gggagaccaa gatgtccaat     120
gccaccctcg tcagctacat tgtgcagatc ctgagccgct atgacatcgc cctggtccag     180
gaggtcagag acagccacct gactgccgtg gggaagctgc tggacaacct caatcaggat     240
gcaccagaca cctatcacta cgtggtcagt gagccactgg gacggaacag ctataaggag     300
cgctacctgt tcgtgtacag gcctgaccag gtgtctgcgg tggacagcta ctactacgat     360
gatggctgcg agccctgcgg gaacgacacc ttcaaccgag agcagccat tgtcaggttc     420
```

```
ttctcccggt tcacagaggt cagggagttt gccattgttc ccctgcatgc ggccccgggg      480
gacgcagtat ccgagatcga cgctctctat gacgtctacc tggatgtcca agagaaatgg      540
ggcttggagg acgtcatgtt gatgggcgac ttcaatgcgg gctgcagcta tgtgagaccc      600
tcccagtggt catccatccg cctgtggaca agccccacct tccagtggct gatccccgac      660
agcgctgaca ccacagctac acccacgcac tgtgcctatg acaggatcgt ggttgcaggg      720
atgctgctcc gaggcgccgt tgttcccgac tcggctcttc cctttaactt ccaggctgcc      780
aatggcctga gtgaccaact ggcccaagcc atcagtgacc actatccagt ggaggtgatg      840
ctgaagtag                                                              849

<210> SEQ ID NO 3
<211> LENGTH: 906
<212> TYPE: DNA
<213> ORGANISM: Homo sapiens

<400> SEQUENCE: 3
atggtgaggg gaatgaagct gctggggggcg ctgctggcac tggcggccct actgcagggg      60
gccgtgtccc tgaagatcgc agccttcaac atccagacat tggggagac caagatgtcc      120 aatgccaccc tcgtcagcta cattgtgcag atcctgagcc gctatgacat cgccctggtc      180
caggaggtca gagacagcca cctgactgcc gtggggaagc tgctggacaa cctcaatcag      240
gatgcaccag acacctatca ctacgtggtc agtgagccac tggacggaa cagctataag      300 gagcgctacc tgttcgtgta caggcctgac caggtgtctg cggtggacag ctactactac      360
gatgatggct gcgagccctg cgggaacgac accttcaacc gagagccagc cattgtcagg      420
ttcttctccc ggttcacaga ggtcaggag tttgccattg ttcccctgca tgcggccccg      480
ggggacgcag tagccgagat cgacgctctc tatgacgtct acctggatgt ccaagagaaa      540
tggggcttgg aggacgtcat gttgatgggc gacttcaatg cgggctgcag ctatgtgaga      600
ccctcccagt ggtcatccat ccgcctgtgg acaagcccca ccttccagtg gctgatcccc      660
gacagcgctg acaccacagc tacacccacg cactgtgcct atgacaggat cgtggttgca      720
gggatgctgc tccgaggcgc cgttgttccc gactcggctc ttccctttaa cttccaggct      780
gccaatggcc tgagtgacca actggcccaa gccatcagtg accactatcc agtggaggtg      840
atgctgaagc tcgagcacca ccaccaccac caccatatgc tcgaggatcc ggctgctaac      900
aaagcc                                                                 906

<210> SEQ ID NO 4
<211> LENGTH: 282
<212> TYPE: PRT
<213> ORGANISM: Homo sapiens

<400> SEQUENCE: 4

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80
```

```
Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ser Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
        210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Asn Gly Leu Ser Asp Gln Leu Ala Gln Ala Ile Ser
            260                 265                 270

Asp His Tyr Pro Val Glu Val Met Leu Lys
        275                 280

<210> SEQ ID NO 5
<211> LENGTH: 302
<212> TYPE: PRT
<213> ORGANISM: Homo sapiens

<400> SEQUENCE: 5

Met Val Arg Gly Met Lys Leu Leu Gly Ala Leu Leu Ala Leu Ala Ala
1               5                   10                  15

Leu Leu Gln Gly Ala Val Ser Leu Lys Ile Ala Ala Phe Asn Ile Gln
                20                  25                  30

Thr Phe Gly Glu Thr Lys Met Ser Asn Ala Thr Leu Val Ser Tyr Ile
            35                  40                  45

Val Gln Ile Leu Ser Arg Tyr Asp Ile Ala Leu Val Gln Glu Val Arg
        50                  55                  60

Asp Ser His Leu Thr Ala Val Gly Lys Leu Leu Asp Asn Leu Asn Gln
65                  70                  75                  80

Asp Ala Pro Asp Thr Tyr His Tyr Val Val Ser Glu Pro Leu Gly Arg
                85                  90                  95

Asn Ser Tyr Lys Glu Arg Tyr Leu Phe Val Tyr Arg Pro Asp Gln Val
            100                 105                 110

Ser Ala Val Asp Ser Tyr Tyr Tyr Asp Asp Gly Cys Glu Pro Cys Gly
            115                 120                 125

Asn Asp Thr Phe Asn Arg Glu Pro Ala Ile Val Arg Phe Phe Ser Arg
        130                 135                 140

Phe Thr Glu Val Arg Glu Phe Ala Ile Val Pro Leu His Ala Ala Pro
145                 150                 155                 160

Gly Asp Ala Val Ala Glu Ile Asp Ala Leu Tyr Asp Val Tyr Leu Asp
                165                 170                 175
```

Val Gln Glu Lys Trp Gly Leu Glu Asp Val Met Leu Met Gly Asp Phe
            180                 185                 190

Asn Ala Gly Cys Ser Tyr Val Arg Pro Ser Gln Trp Ser Ser Ile Arg
            195                 200                 205

Leu Trp Thr Ser Pro Thr Phe Gln Trp Leu Ile Pro Asp Ser Ala Asp
        210                 215                 220

Thr Thr Ala Thr Pro Thr His Cys Ala Tyr Asp Arg Ile Val Val Ala
225                 230                 235                 240

Gly Met Leu Leu Arg Gly Ala Val Val Pro Asp Ser Ala Leu Pro Phe
            245                 250                 255

Asn Phe Gln Ala Ala Asn Gly Leu Ser Asp Gln Leu Ala Gln Ala Ile
            260                 265                 270

Ser Asp His Tyr Pro Val Glu Val Met Leu Lys Leu Glu His His His
            275                 280                 285

His His His His Met Leu Glu Asp Pro Ala Ala Asn Lys Ala
            290                 295                 300

<210> SEQ ID NO 6
<211> LENGTH: 302
<212> TYPE: PRT
<213> ORGANISM: Homo sapiens

<400> SEQUENCE: 6

Met Val Arg Gly Met Lys Leu Leu Gly Ala Leu Leu Ala Leu Ala Ala
1               5                   10                  15

Leu Leu Gln Gly Ala Val Ser Leu Lys Ile Ala Ala Phe Asn Ile Gln
            20                  25                  30

Thr Phe Gly Glu Thr Lys Met Ser Asn Ala Thr Leu Val Ser Tyr Ile
        35                  40                  45

Val Gln Ile Met Ser Arg Tyr Asp Ile Ala Leu Val Gln Glu Val Arg
    50                  55                  60

Asp Ser His Leu Thr Ala Val Gly Lys Leu Leu Asp Asn Leu Asn Gln
65                  70                  75                  80

Asp Ala Pro Asp Thr Tyr His Tyr Val Val Ser Glu Pro Leu Gly Arg
                85                  90                  95

Asn Ser Tyr Lys Glu Arg Tyr Leu Phe Val Tyr Arg Pro Asp Gln Val
            100                 105                 110

Ser Ala Val Asp Ser Tyr Tyr Tyr Asp Asp Gly Cys Glu Pro Cys Gly
            115                 120                 125

Asn Asp Thr Phe Asn Arg Glu Pro Ala Ile Val Arg Phe Phe Ser Arg
        130                 135                 140

Phe Thr Glu Val Arg Glu Phe Ala Ile Val Pro Leu His Ala Ala Pro
145                 150                 155                 160

Gly Asp Ala Val Ala Glu Ile Asp Ala Leu Tyr Asp Val Tyr Leu Asp
            165                 170                 175

Val Gln Glu Lys Trp Gly Leu Glu Asp Val Met Leu Met Gly Asp Phe
            180                 185                 190

Asn Ala Gly Cys Ser Tyr Val Arg Pro Ser Gln Trp Ser Ser Ile Arg
            195                 200                 205

Leu Trp Thr Ser Pro Thr Phe Gln Trp Leu Ile Pro Asp Ser Ala Asp
        210                 215                 220

Thr Thr Ala Thr Pro Thr His Cys Ala Tyr Asp Arg Ile Val Val Ala
225                 230                 235                 240

Gly Met Leu Leu Arg Gly Ala Val Val Pro Asp Ser Ala Leu Pro Phe

```
                     245                 250                 255
Asn Phe Gln Ala Ala Asn Gly Leu Ser Asp Gln Leu Ala Gln Ala Ile
                 260                 265                 270

Ser Asp His Tyr Pro Val Glu Val Met Leu Lys Leu Glu His His His
             275                 280                 285

His His His Met Leu Glu Asp Pro Ala Ala Asn Lys Ala
290                 295                 300

<210> SEQ ID NO 7
<211> LENGTH: 302
<212> TYPE: PRT
<213> ORGANISM: Homo sapiens

<400> SEQUENCE: 7

Met Val Arg Gly Met Lys Leu Leu Gly Ala Leu Leu Ala Leu Ala Ala
1               5                   10                  15

Leu Leu Gln Gly Ala Val Ser Leu Lys Ile Ala Ala Phe Asn Ile Gln
                20                  25                  30

Thr Phe Gly Glu Thr Lys Met Ser Asn Ala Thr Leu Val Ser Tyr Ile
            35                  40                  45

Val Gln Ile Met Ser Arg Tyr Asp Ile Ala Leu Gln Glu Val Arg
    50                  55                  60

Asp Ser His Leu Thr Ala Val Gly Lys Leu Leu Asp Asn Leu Asn Gln
65                  70                  75                  80

Asp Ala Pro Asp Thr Tyr His Tyr Val Val Ser Glu Pro Leu Gly Arg
                85                  90                  95

Asn Ser Tyr Lys Glu Arg Tyr Leu Phe Val Tyr Arg Pro Asp Gln Val
            100                 105                 110

Ser Ala Val Asp Ser Tyr Tyr Tyr Asp Asp Gly Cys Glu Pro Cys Gly
        115                 120                 125

Asn Asp Thr Phe Asn Arg Glu Pro Ala Ile Val Arg Phe Phe Ser Arg
130                 135                 140

Phe Thr Glu Val Arg Glu Phe Ala Ile Val Pro Leu His Ala Ala Pro
145                 150                 155                 160

Gly Asp Ala Val Ala Glu Ile Asp Ala Leu Tyr Asp Val Tyr Leu Asp
                165                 170                 175

Val Gln Glu Lys Trp Gly Leu Glu Asp Val Met Leu Met Gly Asp Phe
            180                 185                 190

Asn Ala Gly Cys Ser Tyr Val Arg Pro Ser Gln Trp Ser Ser Ile Arg
        195                 200                 205

Leu Trp Thr Ser Pro Thr Phe Gln Trp Leu Ile Pro Asp Ser Ala Asp
    210                 215                 220

Thr Thr Ala Thr Pro Thr His Cys Ala Tyr Asp Arg Ile Val Val Ala
225                 230                 235                 240

Gly Met Leu Leu Arg Gly Ala Val Val Pro Asp Ser Ala Leu Pro Phe
                245                 250                 255

Asn Phe Gln Ala Ala Asn Gly Leu Ser Asp Gln Leu Ala Gln Ala Ile
            260                 265                 270

Ser Asp His Tyr Pro Val Glu Val Met Leu Lys Leu Glu His His His
        275                 280                 285

His His His Met Leu Glu Asp Pro Ala Ala Asn Lys Ala
    290                 295                 300

<210> SEQ ID NO 8
<211> LENGTH: 740
```

```
<212> TYPE: DNA
<213> ORGANISM: Actinobacillus actinomycetemcomitans

<400> SEQUENCE: 8
atggctccga ggagaggtac aatgaaaaag tttttacctg gtctttttatt gatgggttta      60
gtggcttgtt cgtcaaatca acgaatgagt gactattctc agcctgaatc tcaatctgat     120
ttagcaccta aatcttcaac aacacaattc caaccccaac cctattatc aaaagcatct      180
tcaatgccat tgaatttgct ctcttcatcc aagaatggac aggtatcgcc gtctgaacca     240
tcaaactta tgactttgat gggacaaaat ggggcactgt tgactgtctg gcgctagca       300
aaacgcaatt ggttatgggc ttatcccaat atatattcgc aggactttgg aaatattcgt     360
aattggaaga tagaacctgg taaacaccgt gaatattttc gttttgttaa tcaatcttta     420
ggtacatgta ttgaagctta cggtaatggt ttaattcatg atacttgtag tctggacaaa     480
ttagcacaag agtttgagtt attacctact gatagtggtg cggttgtcat taaaagtgtg     540
tcacaaggac gttgtgtcac ttataatcct gtaagtccaa catattattc aacagttaca     600
ttatcaactt gtgatggcgc aacagaacca ttacgtgatc aaacatggta tctcgctcct     660
cctgtattag aagcaacagc ggttaatcac caccaccacc accacggatc cgggctgcta     720
acaaagcccc gaaaggaagc                                                 740

<210> SEQ ID NO 9
<211> LENGTH: 239
<212> TYPE: PRT
<213> ORGANISM: Actinobacillus actinomycetemcomitans

<400> SEQUENCE: 9

Met Lys Lys Phe Leu Pro Gly Leu Leu Leu Met Gly Leu Val Ala Cys
1               5                   10                  15

Ser Ser Asn Gln Arg Met Ser Asp Tyr Ser Gln Pro Glu Ser Gln Ser
            20                  25                  30

Asp Leu Ala Pro Lys Ser Ser Thr Thr Gln Phe Gln Pro Gln Pro Leu
        35                  40                  45

Leu Ser Lys Ala Ser Ser Met Pro Leu Asn Leu Leu Ser Ser Ser Lys
    50                  55                  60

Asn Gly Gln Val Ser Pro Ser Glu Pro Ser Asn Phe Met Thr Leu Met
65                  70                  75                  80

Gly Gln Asn Gly Ala Leu Leu Thr Val Trp Ala Leu Ala Lys Arg Asn
                85                  90                  95

Trp Leu Trp Ala Tyr Pro Asn Ile Tyr Ser Gln Asp Phe Gly Asn Ile
            100                 105                 110

Arg Asn Trp Lys Ile Glu Pro Gly Lys His Arg Glu Tyr Phe Arg Phe
        115                 120                 125

Val Asn Gln Ser Leu Gly Thr Cys Ile Glu Ala Tyr Gly Asn Gly Leu
    130                 135                 140

Ile His Asp Thr Cys Ser Leu Asp Lys Leu Ala Gln Glu Phe Glu Leu
145                 150                 155                 160

Leu Pro Thr Asp Ser Gly Ala Val Val Ile Lys Ser Val Ser Gln Gly
                165                 170                 175

Arg Cys Val Thr Tyr Asn Pro Val Ser Pro Thr Tyr Ser Thr Val
            180                 185                 190

Thr Leu Ser Thr Cys Asp Gly Ala Thr Glu Pro Leu Arg Asp Gln Thr
        195                 200                 205

Trp Tyr Leu Ala Pro Pro Val Leu Glu Ala Thr Ala Val Asn His His
```

```
                      210                 215                 220
His His His His Gly Ser Gly Leu Leu Thr Lys Pro Arg Lys Glu
225                 230                 235

<210> SEQ ID NO 10
<211> LENGTH: 163
<212> TYPE: PRT
<213> ORGANISM: Actinobacillus actinomycetemcomitans

<400> SEQUENCE: 10

Leu Leu Ser Ser Lys Asn Gly Gln Val Ser Pro Ser Glu Pro Ser
1               5                   10                  15

Asn Phe Met Thr Leu Met Gly Gln Asn Gly Ala Leu Leu Thr Val Trp
            20                  25                  30

Ala Leu Ala Lys Arg Asn Trp Leu Trp Ala Tyr Pro Asn Ile Tyr Ser
                35                  40                  45

Gln Asp Phe Gly Asn Ile Arg Asn Trp Lys Ile Glu Pro Gly Lys His
        50                  55                  60

Arg Glu Tyr Phe Arg Phe Val Asn Gln Ser Leu Gly Thr Cys Ile Glu
65                  70                  75                  80

Ala Tyr Gly Asn Gly Leu Ile His Asp Thr Cys Ser Leu Asp Lys Leu
                85                  90                  95

Ala Gln Glu Phe Glu Leu Leu Pro Thr Asp Ser Gly Ala Val Val Ile
            100                 105                 110

Lys Ser Val Ser Gln Gly Arg Cys Val Thr Tyr Asn Pro Val Ser Pro
        115                 120                 125

Thr Tyr Tyr Ser Thr Val Thr Leu Ser Thr Cys Asp Gly Ala Thr Glu
    130                 135                 140

Pro Leu Arg Asp Gln Thr Trp Tyr Leu Ala Pro Val Leu Glu Ala
145                 150                 155                 160

Thr Ala Val

<210> SEQ ID NO 11
<211> LENGTH: 489
<212> TYPE: DNA
<213> ORGANISM: Actinobacillus actinomycetemcomitans

<400> SEQUENCE: 11
ttgctctctt catccaagaa tggacaggta tcgccgtctg aaccatcaaa ctttatgact      60
ttgatgggac aaaatggggc actgttgact gtctgggcgc tagcaaaacg caattggtta    120
tgggcttatc ccaatatata ttcgcaggac tttggaaata ttcgtaattg aagatagaa     180 cctggtaaac accgtgaata ttttcgtttt gttaatcaat ctttaggtac atgtattgaa    240
gcttacggta atggtttaat tcatgatact tgtagtctgg acaaattagc acaagagttt    300
gagttattac ctactgatag tggtgcggtt gtcattaaaa gtgtgtcaca aggacgttgt    360
gtcacttata atcctgtaag tccaacatat tattcaacag ttacattatc aacttgtgat    420
ggcgcaacag aaccattacg tgatcaaaca tggtatctcg ctcctcctgt attagaagca    480
acagcggtt                                                            489

<210> SEQ ID NO 12
<211> LENGTH: 261
<212> TYPE: PRT
<213> ORGANISM: Actinobacillus actinomycetemcomitans

<400> SEQUENCE: 12
```

```
Asn Leu Ser Asp Phe Lys Val Ala Thr Trp Asn Leu Gln Gly Ser Ser
1               5                   10                  15

Ala Val Asn Glu Ser Lys Trp Asn Ile Asn Val Arg Gln Leu Leu Ser
            20                  25                  30

Gly Glu Gln Gly Ala Asp Ile Leu Met Val Gln Glu Ala Gly Ser Leu
        35                  40                  45

Pro Ser Ser Ala Val Arg Thr Ser Arg Val Ile Gln His Gly Gly Thr
    50                  55                  60

Pro Ile Glu Glu Tyr Thr Trp Asn Leu Gly Thr Arg Ser Arg Pro Asn
65                  70                  75                  80

Met Val Tyr Ile Tyr Tyr Ser Arg Leu Asp Val Gly Ala Asn Arg Val
                85                  90                  95

Asn Leu Ala Ile Val Ser Arg Arg Gln Ala Asp Glu Ala Phe Ile Val
            100                 105                 110

His Ser Asp Ser Ser Val Leu Gln Ser Arg Pro Ala Val Gly Ile Arg
        115                 120                 125

Ile Gly Thr Asp Val Phe Phe Thr Val His Ala Leu Ala Thr Gly Gly
    130                 135                 140

Ser Asp Ala Val Ser Leu Ile Arg Asn Ile Phe Thr Thr Phe Thr Ser
145                 150                 155                 160

Ser Pro Ser Ser Pro Glu Arg Arg Gly Tyr Ser Trp Met Val Val Gly
                165                 170                 175

Asp Phe Asn Arg Ala Pro Val Asn Leu Glu Ala Ala Leu Arg Gln Glu
            180                 185                 190

Pro Ala Val Ser Glu Asn Thr Ile Ile Ala Pro Thr Glu Pro Thr
        195                 200                 205

His Arg Ser Gly Asn Ile Leu Asp Tyr Ala Ile Leu His Asp Ala His
    210                 215                 220

Leu Pro Arg Arg Glu Gln Ala Arg Glu Arg Ile Gly Ala Ser Leu Met
225                 230                 235                 240

Leu Asn Gln Leu Arg Ser Gln Ile Thr Ser Asp His Phe Pro Val Ser
                245                 250                 255

Phe Val Arg Asp Arg
            260
```

<210> SEQ ID NO 13
<211> LENGTH: 781
<212> TYPE: DNA
<213> ORGANISM: Actinobacillus actinomycetemcomitans

<400> SEQUENCE: 13

```
aacttgagtg atttcaaagt agcaacttgg aatctgcaag gttcttcagc tgtaaatgaa      60
agtaaatgga atattaatgt gcgccaatta ttatcgggag aacaaggtgc agatattttg     120
atggtacaag aagcgggttc attaccaagt tcggcagtaa gaacctcacg agtaattcaa     180
catgggggaa cgccaattga ggaatatacc tggaatttag gtactcgctc ccgtccaaat     240
atggtctata tttattattc ccgtttagat gttggggcaa accgagtgaa cttagctatc     300
gtgtcacgtc gtcaagccga tgaagctttt atcgtacatt ctgattcttc tgtgcttcaa     360
tctcgcccgg cagtaggtat ccgcattggt actgatgtat tttttacagt gcatgctttg     420
gccacaggtg gttctgatgc ggtaagttta attcgtaata tcttcactac ttttacctca     480
tcaccatcat caccggaaag acgaggatat agctggatgg ttgttggtga tttcaatcgt     540
gcgccggtta atctggaagc tgcattaaga caggaaccgg ccgtgagtga aaatacaatt     600
```

```
attattgcgc aacagaacc gactcatcgg tccggtaata ttttagatta tgcgatttta    660
catgacgcac atttaccacg tcgagagcaa gcacgtgaac gtatcggcgc aagtttaatg    720
ttaaatcagt tacgctcaca aattacatcc gatcattttc ctgttagttt tgttcgtgat    780
c                                                                    781
```

<210> SEQ ID NO 14
<211> LENGTH: 276
<212> TYPE: PRT
<213> ORGANISM: Actinobacillus Actinomycetemcomitans

<400> SEQUENCE: 14

```
Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Ser Arg Pro Asn Met Val Tyr Ile Tyr Tyr Ser Arg Leu Asp
            100                 105                 110

Val Gly Ala Asn Arg Val Asn Leu Ala Ile Val Ser Arg Gln Ala
        115                 120                 125

Asp Glu Ala Phe Ile Val His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Leu Ala Thr Gly Gly Ser Asp Ala Val Ser Leu Ile Arg Asn Ile
                165                 170                 175

Phe Thr Thr Phe Thr Ser Ser Pro Ser Ser Pro Glu Arg Gly Tyr
            180                 185                 190

Ser Trp Met Val Val Gly Asp Phe Asn Arg Ala Pro Val Asn Leu Glu
        195                 200                 205

Ala Ala Leu Arg Gln Glu Pro Ala Val Ser Glu Asn Thr Ile Ile Ile
    210                 215                 220

Ala Pro Thr Glu Pro Thr His Gln Ser Gly Asn Ile Leu Asp Tyr Ala
225                 230                 235                 240

Ile Leu His Asp Ala His Leu Pro Arg Arg Glu Gln Val Arg Glu Arg
                245                 250                 255

Ile Gly Ala Ser Leu Met Leu Asn Gln Leu Arg Ser Gln Ile Thr Ser
            260                 265                 270

Asp His Phe Pro
            275
```

<210> SEQ ID NO 15
<211> LENGTH: 828
<212> TYPE: DNA
<213> ORGANISM: Actinobacillus actinomycetemcomitans

<400> SEQUENCE: 15

```
atgcaatggg taaagcaatt aaatgtggtt ttctgtacga tgttatttag cttttcaagt    60
```

```
tatgctaact tgagtgattt caaagtagca acttggaatc tgcaaggttc ttcagctgta      120
aatgaaagta aatggaatat taatgtgcgc caattattat cgggagaaca aggtgcagat      180
attttgatgg tacaagaagc gggttcatta ccaagttcgg cagtaagaac ctcacgagta      240
attcaacatg ggggaacgcc aattgaggaa tatacctgga atttaggtac tcgctcccgt      300
ccaaatatgg tctatattta ttattcccgt ttagatgttg gggcaaaccg agtgaactta      360
gctatcgtgt cacgtcgtca agccgatgaa gcttttatcg tacattctga ttcttctgtg      420
cttcaatctc gcccggcagt aggtatccgc attggtactg atgtattttt tacagtgcat      480
gctttggcca caggtggttc tgatgcggta agtttaattc gtaatatctt cactactttt      540
acctcatcac catcatcacc ggaaagacga ggatatagct ggatggttgt tggtgatttc      600
aatcgtgcgc cggttaatct ggaagctgca ttaagacagg aacccgccgt gagtgaaaat      660
acaattatta ttgcgccaac agaaccgact catcagtccg gtaatatttt agattatgcg      720
attttacatg acgcacattt accacgtcga gagcaagtac gtgaacgtat cggcgcaagt      780
ttaatgttaa atcagttacg ctcacaaatt acatccgatc attttcct                   828
```

<210> SEQ ID NO 16
<211> LENGTH: 293
<212> TYPE: PRT
<213> ORGANISM: Actinobacillus actinomycetemcomitans

<400> SEQUENCE: 16

```
Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Ser Arg Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
        115                 120                 125

Asp Glu Ala Phe Ile Val His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Leu Ala Thr Gly Gly Ser Asp Ala Val Ser Leu Ile Arg Asn Ile
                165                 170                 175

Phe Thr Thr Phe Thr Ser Ser Pro Ser Pro Glu Arg Arg Gly Tyr
            180                 185                 190

Ser Trp Met Val Val Gly Asp Phe Asn Arg Ala Pro Val Asn Leu Glu
        195                 200                 205

Ala Ala Leu Arg Gln Glu Pro Ala Val Ser Glu Asn Thr Ile Ile Ile
    210                 215                 220

Ala Pro Thr Glu Pro Thr His Gln Ser Gly Asn Ile Leu Asp Tyr Ala
225                 230                 235                 240
```

Ile Leu His Asp Ala His Leu Pro Arg Arg Glu Gln Val Arg Glu Arg
            245                 250                 255

Ile Gly Ala Ser Leu Met Leu Asn Gln Leu Arg Ser Gln Ile Thr Ser
            260                 265                 270

Asp His Phe Pro Val Ser Phe Val His Asp Arg His His His His
            275                 280                 285

His Gly Ser Gly Cys
    290

<210> SEQ ID NO 17
<211> LENGTH: 612
<212> TYPE: DNA
<213> ORGANISM: Actinobacillus actinomycetemcomitans

<400> SEQUENCE: 17

| | | |
|---|---|---|
| atggtcgcta aggagaatac tatgaaaaaa tatttattga gcttcttatt aagcatgata | 60 |
| ttgactttga cgagtcatgc agaatcaaat cctgatccga ctacttatcc tgatgtagag | 120 |
| ttatcgcctc ctccacgtat tagcttgcgt agtttgctta cggctcaacc aattaaaaat | 180 |
| gaccattatg attcacataa ttatttaagt acacattggg aattaattga ttacaaggga | 240 |
| aaagaatatg aaaaattacg tgacggtggt acgttggttc aatttaaagt ggtcggtgca | 300 |
| gcaaaatgtt ttgctttccc aggcgaaggc acaactgatt gtaaagatat tgatcatact | 360 |
| gtgtttaacc ttattccaac taatacaggt gcgttttttaa tcaaagatgc cctattagga | 420 |
| ttttgtatga caagccatga ctttgatgat ttgaggcttg aaccttgtgg aatttcagtg | 480 |
| agtggtcgaa ccttttcgtt ggcgtatcaa tggggaatat acctcctttt tgggccaagt | 540 |
| aaaattttaa gaccaccggt ggggagaaat cagggtagcc accaccacca ccaccacgga | 600 |
| tccggctgct aa | 612 |

<210> SEQ ID NO 18
<211> LENGTH: 203
<212> TYPE: PRT
<213> ORGANISM: Actinobacillus actinomycetemcomitans

<400> SEQUENCE: 18

Met Val Ala Lys Glu Asn Thr Met Lys Lys Tyr Leu Leu Ser Phe Leu
1               5                   10                  15

Leu Ser Met Ile Leu Thr Leu Thr Ser His Ala Glu Ser Asn Pro Asp
            20                  25                  30

Pro Thr Thr Tyr Pro Asp Val Glu Leu Ser Pro Pro Arg Ile Ser
            35                  40                  45

Leu Arg Ser Leu Leu Thr Ala Gln Pro Ile Lys Asn Asp His Tyr Asp
    50                  55                  60

Ser His Asn Tyr Leu Ser Thr His Trp Glu Leu Ile Asp Tyr Lys Gly
65                  70                  75                  80

Lys Glu Tyr Glu Lys Leu Arg Asp Gly Gly Thr Leu Val Gln Phe Lys
                85                  90                  95

Val Val Gly Ala Ala Lys Cys Phe Ala Phe Pro Gly Glu Gly Thr Thr
            100                 105                 110

Asp Cys Lys Asp Ile Asp His Thr Val Phe Asn Leu Ile Pro Thr Asn
            115                 120                 125

Thr Gly Ala Phe Leu Ile Lys Asp Ala Leu Leu Gly Phe Cys Met Thr
        130                 135                 140

Ser His Asp Phe Asp Asp Leu Arg Leu Glu Pro Cys Gly Ile Ser Val

```
                145                 150                 155                 160
Ser Gly Arg Thr Phe Ser Leu Ala Tyr Gln Trp Gly Ile Leu Pro Pro
                    165                 170                 175

Phe Gly Pro Ser Lys Ile Leu Arg Pro Pro Val Gly Arg Asn Gln Gly
                180                 185                 190

Ser His His His His His Gly Ser Gly Cys
                195                 200

<210> SEQ ID NO 19
<211> LENGTH: 196
<212> TYPE: PRT
<213> ORGANISM: Actinobacillus Actinomycetemcomitans

<400> SEQUENCE: 19

Met Lys Lys Tyr Leu Leu Ser Phe Leu Leu Ser Met Ile Leu Thr Leu
1               5                   10                  15

Thr Ser His Ala Glu Ser Asn Pro Asp Pro Thr Thr Tyr Pro Asp Val
                20                  25                  30

Glu Leu Ser Pro Pro Arg Ile Ser Leu Arg Ser Leu Leu Thr Ala
            35                  40                  45

Gln Pro Ile Lys Asn Asp His Tyr Asp Ser His Asn Tyr Leu Ser Thr
    50                  55                  60

His Trp Glu Leu Ile Asp Tyr Lys Gly Lys Glu Tyr Glu Lys Leu Arg
65                  70                  75                  80

Asp Gly Gly Thr Leu Val Gln Phe Lys Val Val Gly Ala Ala Lys Cys
                85                  90                  95

Phe Ala Phe Pro Gly Glu Gly Thr Thr Asp Cys Lys Asp Ile Asp His
                100                 105                 110

Thr Val Phe Asn Leu Ile Pro Thr Asn Thr Gly Ala Phe Leu Ile Lys
            115                 120                 125

Asp Ala Leu Leu Gly Phe Cys Met Thr Ser His Asp Phe Asp Asp Leu
    130                 135                 140

Arg Leu Glu Pro Cys Gly Ile Ser Val Ser Gly Arg Thr Phe Ser Leu
145                 150                 155                 160

Ala Tyr Gln Trp Gly Ile Leu Pro Pro Phe Gly Pro Ser Lys Ile Leu
                165                 170                 175

Arg Pro Pro Val Gly Arg Asn Gln Gly Ser His His His His His His
            180                 185                 190

Gly Ser Gly Cys
    195

<210> SEQ ID NO 20
<211> LENGTH: 166
<212> TYPE: PRT
<213> ORGANISM: Actinobacillus Actinomycetemcomitans

<400> SEQUENCE: 20

Glu Ser Asn Pro Asp Pro Thr Thr Tyr Pro Asp Val Glu Leu Ser Pro
1               5                   10                  15

Pro Pro Arg Ile Ser Leu Arg Ser Leu Leu Thr Ala Gln Pro Ile Lys
                20                  25                  30

Asn Asp His Tyr Asp Ser His Asn Tyr Leu Ser Thr His Trp Glu Leu
            35                  40                  45

Ile Asp Tyr Lys Gly Lys Glu Tyr Glu Lys Leu Arg Asp Gly Gly Thr
    50                  55                  60

Leu Val Gln Phe Lys Val Val Gly Ala Ala Lys Cys Phe Ala Phe Pro
```

Gly Glu Gly Thr Thr Asp Cys Lys Asp Ile Asp His Thr Val Phe Asn
65                  70                  75                  80

Leu Ile Pro Thr Asn Thr Gly Ala Phe Leu Ile Lys Asp Ala Leu Leu
            85                  90                  95

Gly Phe Cys Met Thr Ser His Asp Phe Asp Asp Leu Arg Leu Glu Pro
        100                 105                 110

Cys Gly Ile Ser Val Ser Gly Arg Thr Phe Ser Leu Ala Tyr Gln Trp
    115                 120                 125

Gly Ile Leu Pro Pro Phe Gly Pro Ser Lys Ile Leu Arg Pro Pro Val
130                 135                 140

Gly Arg Asn Gln Gly Ser
145                 150                 155                 160

Gly Arg Asn Gln Gly Ser
            165

<210> SEQ ID NO 21
<211> LENGTH: 498
<212> TYPE: DNA
<213> ORGANISM: Actinobacillus actinomycetemcomitans

<400> SEQUENCE: 21
gaatcaaatc ctgatccgac tacttatcct gatgtagagt tatcgcctcc tccacgtatt      60
agcttgcgta gtttgcttac ggctcaacca attaaaaatg accattatga ttcacataat     120
tatttaagta cacattggga attaattgat tacaagggaa agaatatga aaaattacgt     180 gacggtggta cgttggttca atttaaagtg gtcggtgcag caaatgtttt tgctttccca     240
ggcgaaggca caactgattg taaagatatt gatcatactg tgtttaacct tattccaact     300
aatacaggtg cgttttaat caaagatgcc ctattaggat tttgtatgac aagccatgac     360
tttgatgatt tgaggcttga accttgtgga atttcagtga gtggtcgaac cttttcgttg     420
gcgtatcaat ggggaatatt acctcctttt gggccaagta aaattttaag accaccggtg     480
gggagaaatc agggtagc                                                    498

<210> SEQ ID NO 22
<211> LENGTH: 926
<212> TYPE: DNA
<213> ORGANISM: Artificial
<220> FEATURE:
<223> OTHER INFORMATION: CdtB-DNase I chimera

<400> SEQUENCE: 22
tgctaaattc ccctctagaa aatttttgtt aactttaag aaggagatat accatggtga      60
ggggaatgaa gctgctgggg gcgctgctgg cactggcggc cctactgcag ggggccgtgt    120
ccctgaagat cgcagccttc aacatccaga catttgggga gaccaagatg tccaatgcca    180
ccctcgtcag ctacattgtg cagatcctga gccgctatga catcgccctg gtccaggagg    240
tcagagacag ccacctgact gccgtgggga gctgctgga acctcaat caggatgcac       300 cagacaccta tcactacgtg gtcagtgagc cactgggacg gaacagctat aaggagcgct    360
acctgttcgt gtacaggcct gaccaggtgt ctgcggtgga cagctactac tacgatgatg    420
gctgcgagcc ctgcgggaac gacaccttca accgagagcc agccattgtc aggttcttct    480
cccggttcac agaggtcagg gagtttgcca ttgttcccct gcatgctttg gccacaggtg    540
gttctgatgc ggtaagttta attcgtaata tcttcactac ttttacctcg tcaccatcat    600
caccggaaag acgaggatat agctggatgg ttgttggtga tttcaatcgt gcgcggtta    660 atctggaagc tgcattaaga caggaacccg ccgtgagtga aaatacaatt attattgcgc    720

-continued

```
caacagaacc gactcatcag tccggtaata ttttagatta tgcgatttta catgacgcac      780
atttaccacg tcgagagcaa gtacgtgaac gtatcggcgc aagtttaatg ttaaatcagt      840
tacgctcaca aattacatcc gatcattttc ctgttagttt tgttcatgat cgccaccacc      900
accaccacca cggatccggc tgctaa                                           926
```

<210> SEQ ID NO 23
<211> LENGTH: 1073
<212> TYPE: DNA
<213> ORGANISM: Artificial
<220> FEATURE:
<223> OTHER INFORMATION: CdtB-DNase I chimera

<400> SEQUENCE: 23

```
atgcaatggg taaagcaatt aaatgtggtt ttctgtacga tgttatttag cttttcaagt       60
tatgctaact tgagtgattt caaagtagca acttggaatc tgcaaggttc ttcagctgta      120
aatgaaagta atggaatat taatgtgcgc caattattat cgggagaaca aggtgcagat      180
attttgatgg tacaagaagc gggttcatta ccaagttcgg cagtaagaac ctcacgagta      240
attcaacatg ggggaacgcc aattgaggaa tatacctgga atttaggtac tcgctcccgt      300
ccaaatatgg tctatattta ttattcccgt ttagatgttg gggcaaaccg agtgaactta      360
gctatcgtgt cacgtcgtca agccgatgaa gctttatcg tacattctga ttcttctgtg      420
cttcaatctc gcccggcagt aggtatccgc attggtactg atgtattttt tacagtgcat      480
gcggccccgg gggacgcagt agccgagatc gacgctctct atgacgtcta cctggatgtc      540
caagagaaat ggggcttgga ggacgtcatg ttgatgggcg acttcaatgc gggctgcagc      600
tatgtgagac cctcccagtg gtcatccatc cgcctgtgga caagccccac cttccagtgg      660
ctgatccccg acagcgctga caccacagct acacccacgc actgtgccta tgacaggatc      720
gtggttgcag gatgctgct ccgaggcgcc gttgttccg actcggctct ccctttaac       780 ttccaggctg ccaatggcct gagtgaccaa ctggcccaag ccatcagtga ccactatcca      840
gtggaggtga tgctgaaggg atcccgggag ctcgtggatc cgaattctgt acaggcgcgc      900
ctgcaggacg tcgacggtac catcgatacg cgttcgaagc ttgcggccgc acagctgtat      960
acacgtgcaa gccagccaga actcgctcct gaagacccag aggatctcga gcaccaccac     1020
caccaccacc atatgctcga ggatccggct gctaacaaag cccgaaaaga agg            1073
```

<210> SEQ ID NO 24
<211> LENGTH: 290
<212> TYPE: PRT
<213> ORGANISM: Artificial
<220> FEATURE:
<223> OTHER INFORMATION: CdtB-DNase I chimera

<400> SEQUENCE: 24

```
Met Val Arg Gly Met Lys Leu Leu Gly Ala Leu Leu Ala Leu Ala Ala
1               5                   10                  15

Leu Leu Gln Gly Ala Val Ser Leu Lys Ile Ala Ala Phe Asn Ile Gln
                20                  25                  30

Thr Phe Gly Glu Thr Lys Met Ser Asn Ala Thr Leu Val Ser Tyr Ile
            35                  40                  45

Val Gln Ile Leu Ser Arg Tyr Asp Ile Ala Leu Val Gln Glu Val Arg
        50                  55                  60

Asp Ser His Leu Thr Ala Val Gly Lys Leu Leu Asp Asn Leu Asn Gln
65                  70                  75                  80
```

```
Asp Ala Pro Asp Thr Tyr His Tyr Val Val Ser Glu Pro Leu Gly Arg
                 85                  90                  95

Asn Ser Tyr Lys Glu Arg Tyr Leu Phe Val Tyr Arg Pro Asp Gln Val
            100                 105                 110

Ser Ala Val Asp Ser Tyr Tyr Asp Asp Gly Cys Glu Pro Cys Gly
            115                 120                 125

Asn Asp Thr Phe Asn Arg Glu Pro Ala Ile Val Arg Phe Phe Ser Arg
    130                 135                 140

Phe Thr Glu Val Arg Glu Phe Ala Ile Val Pro Leu His Ala Leu Ala
145                 150                 155                 160

Thr Gly Gly Ser Asp Ala Val Ser Leu Ile Arg Asn Ile Phe Thr Thr
                165                 170                 175

Phe Thr Ser Ser Pro Ser Pro Glu Arg Arg Gly Tyr Ser Trp Met
            180                 185                 190

Val Val Gly Asp Phe Asn Arg Ala Pro Val Asn Leu Glu Ala Ala Leu
            195                 200                 205

Arg Gln Glu Pro Ala Val Ser Glu Asn Thr Ile Ile Ile Ala Pro Thr
            210                 215                 220

Glu Pro Thr His Gln Ser Gly Asn Ile Leu Asp Tyr Ala Ile Leu His
225                 230                 235                 240

Asp Ala His Leu Pro Arg Arg Glu Gln Val Arg Glu Arg Ile Gly Ala
                245                 250                 255

Ser Leu Met Leu Asn Gln Leu Arg Ser Gln Ile Thr Ser Asp His Phe
            260                 265                 270

Pro Val Ser Phe Val His Asp Arg His His His His His Gly Ser
            275                 280                 285

Gly Cys
    290

<210> SEQ ID NO 25
<211> LENGTH: 358
<212> TYPE: PRT
<213> ORGANISM: Artificial
<220> FEATURE:
<223> OTHER INFORMATION: CdtB-DNase I

<400> SEQUENCE: 25

Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Ser Arg Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
            115                 120                 125

Asp Glu Ala Phe Ile Val His Ser Asp Ser Ser Val Leu Gln Ser Arg
    130                 135                 140
```

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
            165                 170                 175

Tyr Leu Asp Val Gln Glu Lys Trp Gly Leu Glu Asp Val Met Leu Met
        180                 185                 190

Gly Asp Phe Asn Ala Gly Cys Ser Tyr Val Arg Pro Ser Gln Trp Ser
    195                 200                 205

Ser Ile Arg Leu Trp Thr Ser Pro Thr Phe Gln Trp Leu Ile Pro Asp
210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Asn Gly Leu Ser Asp Gln Leu Ala
            260                 265                 270

Gln Ala Ile Ser Asp His Tyr Pro Val Glu Val Met Leu Lys Gly Ser
        275                 280                 285

Arg Glu Leu Val Asp Pro Asn Ser Val Gln Ala Arg Leu Gln Asp Val
    290                 295                 300

Asp Gly Thr Ile Asp Thr Arg Ser Lys Leu Ala Ala Gln Leu Tyr
305                 310                 315                 320

Thr Arg Ala Ser Gln Pro Glu Leu Ala Pro Glu Asp Pro Glu Asp Leu
            325                 330                 335

Glu His His His His His His Met Leu Glu Asp Pro Ala Ala Asn
                340                 345                 350

Lys Ala Arg Lys Glu Gly
        355

<210> SEQ ID NO 26
<211> LENGTH: 306
<212> TYPE: PRT
<213> ORGANISM: Artificial
<220> FEATURE:
<223> OTHER INFORMATION: CdtB-DNase I chimera

<400> SEQUENCE: 26

Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Ser Arg Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
        115                 120                 125

Asp Glu Ala Phe Ile Val His Ser Asp Ser Ser Val Leu Gln Ser Arg
    130                 135                 140

```
Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
        195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Asn Gly Leu Ser Asp Gln Leu Ala
            260                 265                 270

Gln Ala Ile Ser Asp His Tyr Pro Val Glu Val Met Leu Lys His His
        275                 280                 285

His His His His His Met Leu Glu Asp Pro Ala Ala Asn Lys Ala Gln
        290                 295                 300

Lys Lys
305

<210> SEQ ID NO 27
<211> LENGTH: 290
<212> TYPE: PRT
<213> ORGANISM: Artificial
<220> FEATURE:
<223> OTHER INFORMATION: CdtB-DNase I chimera

<400> SEQUENCE: 27

Met Val Arg Gly Met Lys Leu Leu Gly Ala Leu Leu Ala Leu Ala Ala
1               5                   10                  15

Leu Leu Gln Gly Ala Val Ser Leu Lys Ile Ala Ala Phe Asn Ile Gln
            20                  25                  30

Thr Phe Gly Glu Thr Lys Met Ser Asn Ala Thr Leu Val Ser Tyr Ile
        35                  40                  45

Val Gln Ile Leu Ser Arg Tyr Asp Ile Ala Leu Val Gln Glu Val Arg
    50                  55                  60

Asp Ser His Leu Thr Ala Val Gly Lys Leu Leu Asp Asn Leu Asn Gln
65                  70                  75                  80

Asp Ala Pro Asp Thr Tyr His Tyr Val Val Ser Glu Pro Leu Gly Arg
                85                  90                  95

Asn Ser Tyr Lys Glu Arg Tyr Leu Phe Val Tyr Arg Pro Asp Gln Val
            100                 105                 110

Ser Ala Val Asp Ser Tyr Tyr Tyr Asp Asp Gly Cys Glu Pro Cys Gly
        115                 120                 125

Asn Asp Thr Phe Asn Arg Glu Pro Ala Ile Val Arg Phe Phe Ser Arg
    130                 135                 140

Phe Thr Glu Val Arg Glu Phe Ala Ile Val Pro Leu His Ala Leu Ala
145                 150                 155                 160

Thr Gly Gly Ser Asp Ala Val Ser Leu Ile Arg Asn Ile Phe Thr Thr
                165                 170                 175

Phe Thr Ser Ser Pro Ser Ser Pro Glu Arg Arg Gly Tyr Ser Trp Met
            180                 185                 190
```

Val Val Gly Asp Phe Asn Arg Ala Pro Val Asn Leu Glu Ala Ala Leu
        195                 200                 205

Arg Gln Glu Pro Ala Val Ser Glu Asn Thr Ile Ile Ile Ala Pro Thr
    210                 215                 220

Glu Pro Thr His Gln Ser Gly Asn Ile Leu Asp Tyr Ala Ile Leu His
225                 230                 235                 240

Asp Ala His Leu Pro Arg Arg Glu Gln Val Arg Glu Arg Ile Gly Ala
                245                 250                 255

Ser Leu Met Leu Asn Gln Leu Arg Ser Gln Ile Thr Ser Asp His Phe
        260                 265                 270

Pro Val Ser Phe Val His Asp Arg His His His His His Gly Ser
        275                 280                 285

Gly Cys
    290

<210> SEQ ID NO 28
<211> LENGTH: 917
<212> TYPE: DNA
<213> ORGANISM: Artificial
<220> FEATURE:
<223> OTHER INFORMATION: CdtB/DNaseY174 chimera

<400> SEQUENCE: 28
atggaatggg taaagcaatt aaatgtggtt ttctgtacga tgttatttag cttttcaagt      60
tatgctaact tgagtgattt caaagtagca acttggaatc tgcaaggttc ttcagctgta    120
aatgaaagta atggaatata taatgtgcgc caattattat cgagggaaca aggtgcagat    180
attgagatgg tacaagaagc gggttcatta ccaagttcgg cagtaagaac ctcacgagta    240
attcaacatg ggggaacgcc aattgaggaa tatacctgga atttaggtac tcgctatgag    300
ccaaatatgg tctatattta ttattcccgt ttagatgttg gggcaaaccg agtgaactta    360
gctatcgtgt cacgtcgtca agccgatgaa gcttttatcc gacattctga ttcttctgtg    420
cttcaatctc gcccggcagt aggtatccgc attggtactg atgtattttt tacagtgcat    480
gcggccccgg gggacgcagt agccgagatc gacgctctcc ctgacgtcta cctggatgtc    540
caagagaaat ggggcttgga ggacgtcatg ttgatgggcg acttcaatgc gggctgcagc    600
tatgtgagac cctcccagtg gtcatccatc cgcctgtgga caagcccccac cttccagtgg    660 ctgatccccg acagcgctga caccacagct acacccacgc actgtgccta tgacaggatc    720
gtggttgcag ggatgctgct ccgaggcgcc gttgttcccg actcggctct tccctttaac    780
ttccaggctg ccttaatgtt aaatcagtta cgctcacaaa ttacaagtga ccactatcca    840
gtggaggtga tgctgaagca ccaccaccac caccatata tgctcgagga tccggctgct    900
aacaagctga agaagc                                                    917

<210> SEQ ID NO 29
<211> LENGTH: 306
<212> TYPE: PRT
<213> ORGANISM: Artificial
<220> FEATURE:
<223> OTHER INFORMATION: CdtB/DNaseY174 chimera

<400> SEQUENCE: 29

Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
            35                  40                  45

Val Arg Gln Leu Leu Ser Arg Glu Gln Gly Ala Asp Ile Glu Met Val
 50                  55                  60

Gln Glu Ala Gly Ser Leu Pro Ser Ser Ala Val Arg Thr Ser Arg Val
 65                  70                  75                  80

Ile Gln His Gly Gly Thr Pro Ile Glu Glu Tyr Thr Trp Asn Leu Gly
                 85                  90                  95

Thr Arg Tyr Glu Pro Asn Met Val Tyr Ile Tyr Ser Arg Leu Asp
            100                 105                 110

Val Gly Ala Asn Arg Val Asn Leu Ala Ile Val Ser Arg Arg Gln Ala
            115                 120                 125

Asp Glu Ala Phe Ile Arg His Ser Asp Ser Ser Val Leu Gln Ser Arg
130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Pro Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
            195                 200                 205

Ser Ile Arg Leu Trp Thr Ser Pro Thr Phe Gln Trp Leu Ile Pro Asp
            210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Leu Met Leu Asn Gln Leu Arg Ser
            260                 265                 270

Gln Ile Thr Ser Asp His Tyr Pro Val Glu Val Met Leu Lys His His
            275                 280                 285

His His His His Met Leu Glu Asp Pro Ala Ala Asn Lys Leu Lys
        290                 295                 300

Glu Ala
305

<210> SEQ ID NO 30
<211> LENGTH: 917
<212> TYPE: DNA
<213> ORGANISM: Artificial
<220> FEATURE:
<223> OTHER INFORMATION: CdtB/DNase I chimera mutant

<400> SEQUENCE: 30
atggaatggg taaagcaatt aaatgtggtt ttctgtacga tgttatttag cttttcaagt      60
tatgctaact tgagtgattt caaagtagca acttggaatc tgcaaggttc ttcagctgta     120
aatgaaagta atggaatat taatgtgcgc caattattat cgagggaaca aggtgcagat     180
attgagatgg tacaagaagc gggttcatta ccaagttcgg cagtaagaac ctcacgagta     240
attcaacatg ggggaacgcc aattgaggaa tatacctgga atttaggtac cgctatgag     300 ccaaatatgg tctatattta ttattcccgt ttagatgttg ggcaaaccg agtgaactta     360 gctatcgtgt cacgtcgtca agccgatgaa gcttttatcc gacattctga ttcttctgtg     420

```
cttcaatctc gcccggcagt aggtatccgc attggtactg atgtattttt tacagtgcat    480
gcggccccgg gggacgcagt agccgagatc gacgctctct atgacgtcta cctggatgtc    540
caagagaaat ggggcttgga ggacgtcatg ttgatgggcg acttcaatgc gggctgcagc    600
tatgtgagac cctcccagtg gtcatccatc cgcctgtgga caagcccac cttccagtgg     660 ctgatccccg acagcgctga caccacagct acacccacgc actgtgccta tgacaggatc    720
gtggttgcag gatgctgct ccgaggcgcc gttgttcccg actcggctct tccctttaac     780
ttccaggctg ccaatggcct gagtgaccaa ctggcccaag ccatcagtga ccactatcca    840
gtggaggtga tgctgaagca ccaccaccac caccaccata tgctcgagga tccggctgct    900
aacaagctga agaagc                                                    917
```

<210> SEQ ID NO 31
<211> LENGTH: 306
<212> TYPE: PRT
<213> ORGANISM: Artificial
<220> FEATURE:
<223> OTHER INFORMATION: CdtB/DNase I chimera mutant

<400> SEQUENCE: 31

```
Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Arg Glu Gln Gly Ala Asp Ile Glu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Tyr Glu Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
        115                 120                 125

Asp Glu Ala Phe Ile Arg His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
        195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Asn Gly Leu Ser Asp Gln Leu Ala
            260                 265                 270
```

Gln Ala Ile Ser Asp His Tyr Pro Val Glu Val Met Leu Lys His His
        275                 280                 285

His His His His His Met Leu Glu Asp Pro Ala Ala Asn Lys Leu Lys
    290                 295                 300

Glu Ala
305

<210> SEQ ID NO 32
<211> LENGTH: 917
<212> TYPE: DNA
<213> ORGANISM: Artificial
<220> FEATURE:
<223> OTHER INFORMATION: CdtB/DNase I chimera mutant

<400> SEQUENCE: 32
atggaatggg taaagcaatt aaatgtggtt ttctgtacga tgttatttag cttttcaagt      60
tatgctaact tgagtgattt caaagtagca acttggaatc tgcaaggttc ttcagctgta     120
aatgaaagta atggaatat taatgtgcgc caattattat cgggagaaca aggtgcagat     180
attttgatgg tacaagaagc gggttcatta ccaagttcgg cagtaagaac ctcacgagta     240
attcaacatg ggggaacgcc aattgaggaa tatacctgga atttaggtac cgctatgag     300
ccaaatatgg tctatattta ttattcccgt ttagatgttg gggcaaaccg agtgaactta     360
gctatcgtgt cacgtcgtca agccgatgaa gcttttatcg tacattctga ttcttctgtg     420
cttcaatctc gcccggcagt aggtatccgc attggtactg atgtattttt tacagtgcat     480
gcggccccgg gggacgcagt agccgagatc gacgctctct atgacgtcta cctggatgtc     540
caagagaaat ggggcttgga ggacgtcatg ttgatgggcg acttcaatgc gggctgcagc     600
tatgtgagac cctcccagtg gtcatccatc cgcctgtgga caagcccac cttccagtgg     660
ctgatccccg acagcgctga caccacagct acacccacgc actgtgccta tgacaggatc     720
gtggttgcag gatgctgct ccgaggcgcc gttgttcccg actcggctct tccctttaac     780
ttccaggctg ccaatggcct gagtgaccaa ctggcccaag ccatcagtga ccactatcca     840
gtggaggtga tgctgaagca ccaccaccac caccaccata tgctcgagga tccggctgct     900
aacaagctga agaagc                                                    917

<210> SEQ ID NO 33
<211> LENGTH: 306
<212> TYPE: PRT
<213> ORGANISM: Artificial
<220> FEATURE:
<223> OTHER INFORMATION: CdtB/DNase I chimera mutant

<400> SEQUENCE: 33

Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

```
Thr Arg Tyr Glu Pro Asn Met Val Tyr Ile Tyr Ser Arg Leu Asp
            100                 105                 110

Val Gly Ala Asn Arg Val Asn Leu Ala Ile Val Ser Arg Gln Ala
        115                 120                 125

Asp Glu Ala Phe Ile Val His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
            195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Asn Gly Leu Ser Asp Gln Leu Ala
            260                 265                 270

Gln Ala Ile Ser Asp His Tyr Pro Val Glu Val Met Leu Lys His His
            275                 280                 285

His His His His Met Leu Glu Asp Pro Ala Ala Asn Lys Leu Lys
290                 295                 300

Glu Ala
305

<210> SEQ ID NO 34
<211> LENGTH: 917
<212> TYPE: DNA
<213> ORGANISM: Artificial
<220> FEATURE:
<223> OTHER INFORMATION: CdtB/DNase I chimera mutant

<400> SEQUENCE: 34
atggaatggg taaagcaatt aaatgtggtt ttctgtacga tgttatttag cttttcaagt      60
tatgctaact tgagtgattt caaagtagca acttggaatc tgcaaggttc ttcagctgta     120
aatgaaagta atggaatat taatgtgcgc caattattat cgagggaaca aggtgcagat     180
attgagatgg tacaagaagc gggttcatta ccaagttcgg cagtaagaac ctcacgagta     240
attcaacatg ggggaacgcc aattgaggaa tatacctgga atttaggtac tcgctatgag     300
ccaaatatgg tctatattta ttattcccgt ttagatgttg gggcaaaccg agtgaactta     360
gctatcgtgt cacgtcgtca agccgatgaa gcttttatcc gacattctga ttcttctgtg     420
cttcaatctc gcccggcagt aggtatccgc attggtactg atgtattttt tacagtgcat     480
gcggccccgg ggacgcagt agccgagatc gacgctctct atgacgtcta cctggatgtc     540
caagagaaat ggggcttgga ggacgtcatg ttgatgggcg acttcaatgc gggctgcagc     600
tatgtgagac cctcccagtg gtcatccatc cgcctgtgga caagccccac cttccagtgg     660 ctgatcccg acagcgctga caccacagct acacccacgc actgtgccta tgacaggatc     720
gtggttgcag ggatgctgct ccgaggcgcc gttgttcccg actcggctct tccctttaac     780
ttccaggctg cctaatgtt aaatcagtta cgctcacaaa ttacaagtga ccactatcca     840
```

```
gtggaggtga tgctgaagca ccaccaccac caccaccata tgctcgagga tccggctgct    900
aacaagctga aagaagc                                                  917
```

<210> SEQ ID NO 35
<211> LENGTH: 306
<212> TYPE: PRT
<213> ORGANISM: Artificial
<220> FEATURE:
<223> OTHER INFORMATION: CdtB/DNase I chimera mutant

<400> SEQUENCE: 35

```
Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Arg Glu Gln Gly Ala Asp Ile Glu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Tyr Glu Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
        115                 120                 125

Asp Glu Ala Phe Ile Arg His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
        195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Leu Met Leu Asn Gln Leu Arg Ser
            260                 265                 270

Gln Ile Thr Ser Asp His Tyr Pro Val Glu Val Met Leu Lys His His
        275                 280                 285

His His His His His Met Leu Glu Asp Pro Ala Ala Asn Lys Leu Lys
    290                 295                 300

Glu Ala
305
```

<210> SEQ ID NO 36
<211> LENGTH: 917
<212> TYPE: DNA

<213> ORGANISM: Artificial
<220> FEATURE:
<223> OTHER INFORMATION: CdtB/DNase I chimera mutant

<400> SEQUENCE: 36

```
atggaatggg taaagcaatt aaatgtggtt ttctgtacga tgttatttag cttttcaagt    60
tatgctaact tgagtgattt caaagtagca acttggaatc tgcaaggttc ttcagctgta   120
aatgaaagta atggaatat taatgtgcgc caattattat cgggagaaca aggtgcagat   180
attgagatgg tacaagaagc gggttcatta ccaagttcgg cagtaagaac ctcacgagta   240
attcaacatg ggggaacgcc aattgaggaa tatacctgga atttaggtac cgctatgag   300
ccaaatatgg tctatattta ttattcccgt ttagatgttg gggcaaaccg agtgaactta   360
gctatcgtgt cacgtcgtca agccgatgaa gcttttatcg tacattctga ttcttctgtg   420
cttcaatctc gcccggcagt aggtatccgc attggtactg atgtattttt tacagtgcat   480
gcggccccgg gggacgcagt agccgagatc gacgctctct atgacgtcta cctggatgtc   540
caagagaaat ggggcttgga ggacgtcatg ttgatgggcg acttcaatgc gggctgcagc   600
tatgtgagac cctcccagtg gtcatccatc cgcctgtgga caagcccac cttccagtgg   660
ctgatccccg acagcgctga caccacagct acacccacgc actgtgccta tgacaggatc   720
gtggttgcag gatgctgctc cgaggcgcc gttgttcccg actcggctct tccctttaac   780
ttccaggctg ccaatggcct gagtgaccaa ctggcccaag ccatcagtga ccactatcca   840
gtggaggtga tgctgaagca ccaccaccac caccacata tgctcgagga tccggctgct   900
aacaagctga agaagc                                                  917
```

<210> SEQ ID NO 37
<211> LENGTH: 306
<212> TYPE: PRT
<213> ORGANISM: Artificial
<220> FEATURE:
<223> OTHER INFORMATION: CdtB/DNase I chimera mutant

<400> SEQUENCE: 37

```
Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gln Gly Ala Asp Ile Glu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Tyr Glu Pro Asn Met Val Tyr Ile Tyr Tyr Ser Arg Leu Asp
            100                 105                 110

Val Gly Ala Asn Arg Val Asn Leu Ala Ile Val Ser Arg Arg Gln Ala
        115                 120                 125

Asp Glu Ala Phe Ile Val His Ser Asp Ser Ser Val Leu Gln Ser Arg
    130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
```

```
                165                 170                 175
Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
        195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Pro Asp Ser Ala
                245                 250                 255

Leu Pro Phe Asn Phe Gln Ala Ala Asn Gly Leu Ser Asp Gln Leu Ala
            260                 265                 270

Gln Ala Ile Ser Asp His Tyr Pro Val Glu Val Met Leu Lys His His
        275                 280                 285

His His His His His Met Leu Glu Asp Pro Ala Ala Asn Lys Leu Lys
    290                 295                 300

Glu Ala
305
```

<210> SEQ ID NO 38
<211> LENGTH: 917
<212> TYPE: DNA
<213> ORGANISM: Artificial
<220> FEATURE:
<223> OTHER INFORMATION: CdtB/DNase I chimera mutant

<400> SEQUENCE: 38

```
atggaatggg taaagcaatt aaatgtggtt ttctgtacga tgttatttag cttttcaagt      60
tatgctaact tgagtgattt caaagtagca acttggaatc tgcaaggttc ttcagctgta    120
aatgaaagta atggaatat taatgtgcgc caattattat cgagggaaca aggtgcagat    180
attgagatgg tacaagaagc gggttcatta ccaagttcgg cagtaagaac ctcacgagta    240
attcaacatg ggggaacgcc aattgaggaa tatacctgga atttaggtac tcgctatgag    300
ccaaatatgg tctatattta ttattcccgt ttagatgttg gggcaaaccg agtgaactta    360
gctatcgtgt cacgtcgtca agccgatgaa gcttttatcg tacattctga ttcttctgtg    420
cttcaatctc gcccggcagt aggtatccgc attggtactg atgtattttt tacagtgcat    480
gcggccccgg ggacgcagt agccgagatc gacgctctct atgacgtcta cctggatgtc    540
caagagaaat ggggcttgga ggacgtcatg ttgatgggcg acttcaatgc gggctgcagc    600
tatgtgagac cctcccagtg gtcatccatc cgcctgtgga caagcccac cttccagtgg    660
ctgatccccg acagcgctga caccacagct acacccacgc actgtgccta tgacaggatc    720
gtggttgcag ggatgctgct ccgaggcgcc gttgttcccg actcggctct tccctttaac    780
ttccaggctg ccaatggcct gagtgaccaa ctggcccaag ccatcagtga ccactatcca    840
gtggaggtga tgctgaagca ccaccaccac caccacata tgctcgagga tccggctgct    900
aacaagctga agaagc                                                   917
```

<210> SEQ ID NO 39
<211> LENGTH: 306
<212> TYPE: PRT
<213> ORGANISM: Artificial
<220> FEATURE:
<223> OTHER INFORMATION: CdtB/DNase I chimera mutant

<400> SEQUENCE: 39

```
Met Glu Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Arg Glu Gln Gly Ala Asp Ile Glu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Tyr Glu Pro Asn Met Val Tyr Ile Tyr Ser Arg Leu Asp
            100                 105                 110

Val Gly Ala Asn Arg Val Asn Leu Ala Ile Val Ser Arg Arg Gln Ala
            115                 120                 125

Asp Glu Ala Phe Ile Val His Ser Asp Ser Ser Val Leu Gln Ser Arg
130                 135                 140

Pro Ala Val Gly Ile Arg Ile Gly Thr Asp Val Phe Phe Thr Val His
145                 150                 155                 160

Ala Ala Pro Gly Asp Ala Val Ala Glu Ile Asp Ala Leu Tyr Asp Val
                165                 170                 175

Tyr Leu Asp Val Gln Glu Lys Trp Gly Leu Glu Asp Val Met Leu Met
            180                 185                 190

Gly Asp Phe Asn Ala Gly Cys Ser Tyr Val Arg Pro Ser Gln Trp Ser
        195                 200                 205

Ser Ile Arg Leu Trp Thr Ser Pro Thr Phe Gln Trp Leu Ile Pro Asp
    210                 215                 220

Ser Ala Asp Thr Thr Ala Thr Pro Thr His Cys Ala Tyr Asp Arg Ile
225                 230                 235                 240

Val Val Ala Gly Met Leu Leu Arg Gly Ala Val Val Pro Asp Ser Ala
                245                 250                 255

Leu Pro Phe Asn Phe Gln Ala Ala Asn Gly Leu Ser Asp Gln Leu Ala
            260                 265                 270

Gln Ala Ile Ser Asp His Tyr Pro Val Glu Val Met Leu Lys His His
        275                 280                 285

His His His His His Met Leu Glu Asp Pro Ala Ala Asn Lys Leu Lys
    290                 295                 300

Glu Ala
305
```

<210> SEQ ID NO 40
<211> LENGTH: 27
<212> TYPE: DNA
<213> ORGANISM: Artificial
<220> FEATURE:
<223> OTHER INFORMATION: N-DNase-F primer

<400> SEQUENCE: 40
aaattaccat ggtgagggga atgaagc                                27

<210> SEQ ID NO 41
<211> LENGTH: 27
<212> TYPE: DNA
<213> ORGANISM: Artificial

```
<220> FEATURE:
<223> OTHER INFORMATION: X-DNase-R Primer

<400> SEQUENCE: 41
taatattctc gagcttcagc atcacct                                          27

<210> SEQ ID NO 42
<211> LENGTH: 28
<212> TYPE: DNA
<213> ORGANISM: Artificial
<220> FEATURE:
<223> OTHER INFORMATION: N-cdtB-F Primer

<400> SEQUENCE: 42
aaacgcgcca tggagtgggt aaagcaat                                         28

<210> SEQ ID NO 43
<211> LENGTH: 22
<212> TYPE: DNA
<213> ORGANISM: Artificial
<220> FEATURE:
<223> OTHER INFORMATION: S-cdtB-R Primer

<400> SEQUENCE: 43
ggccaaagca tgcactgtaa aa                                               22

<210> SEQ ID NO 44
<211> LENGTH: 37
<212> TYPE: DNA
<213> ORGANISM: Artificial
<220> FEATURE:
<223> OTHER INFORMATION: NdeI-His Primer

<400> SEQUENCE: 44
attaacttaa ttacatatgg tggtggtggt ggtggtg                               37

<210> SEQ ID NO 45
<211> LENGTH: 39
<212> TYPE: DNA
<213> ORGANISM: Artificial
<220> FEATURE:
<223> OTHER INFORMATION: DNaseI-His Primer

<400> SEQUENCE: 45
tttggatccg tggtggtggt ggtggtgctt cagcatcac                             39

<210> SEQ ID NO 46
<211> LENGTH: 41
<212> TYPE: DNA
<213> ORGANISM: Artificial
<220> FEATURE:
<223> OTHER INFORMATION: H160Afor Primer

<400> SEQUENCE: 46
actgatgtat tttttacagt ggctgctttg gccacaggtg g                          41

<210> SEQ ID NO 47
<211> LENGTH: 41
<212> TYPE: DNA
<213> ORGANISM: Artificial
<220> FEATURE:
<223> OTHER INFORMATION: H160Arev Primer

<400> SEQUENCE: 47
ccacctgtgg ccaaagcagc cactgtaaaa aatacatcag t                          41
```

<210> SEQ ID NO 48
<211> LENGTH: 58
<212> TYPE: DNA
<213> ORGANISM: Artificial
<220> FEATURE:
<223> OTHER INFORMATION: CdtB-DN-S99Y, R100E-F Primer

<400> SEQUENCE: 48
gaggaatata cctggaattt aggtactcgc tatgagccaa atatggtcta tatttatt       58

<210> SEQ ID NO 49
<211> LENGTH: 58
<212> TYPE: DNA
<213> ORGANISM: Artificial
<220> FEATURE:
<223> OTHER INFORMATION: CdtB-DN-S99Y, R100E-R Primer

<400> SEQUENCE: 49
aataaatata gaccatattt ggctcatagc gagtacctaa attccaggta tattcctc       58

<210> SEQ ID NO 50
<211> LENGTH: 49
<212> TYPE: DNA
<213> ORGANISM: Artificial
<220> FEATURE:
<223> OTHER INFORMATION: CdtB-DN-L62E-F Primer

<400> SEQUENCE: 50
aattattatc gcgagaacaa ggtgcagata ttgagatggt acaagaagc              49

<210> SEQ ID NO 51
<211> LENGTH: 49
<212> TYPE: DNA
<213> ORGANISM: Artificial
<220> FEATURE:
<223> OTHER INFORMATION: CdtB-DN-L62E-R Primer

<400> SEQUENCE: 51
gcttcttgta ccatctcaat atctgcacct tgttctcgcg ataataatt              49

<210> SEQ ID NO 52
<211> LENGTH: 35
<212> TYPE: DNA
<213> ORGANISM: Artificial
<220> FEATURE:
<223> OTHER INFORMATION: CdtB-DN-G55R-F Primer

<400> SEQUENCE: 52
aatgtgcgcc aattattatc gagggaacaa ggtgc                              35

<210> SEQ ID NO 53
<211> LENGTH: 35
<212> TYPE: DNA
<213> ORGANISM: Artificial
<220> FEATURE:
<223> OTHER INFORMATION: CdtB-DN-G55R-R Primer

<400> SEQUENCE: 53
gcaccttgtt ccctcgataa taattggcgc acatt                              35

<210> SEQ ID NO 54
<211> LENGTH: 44
<212> TYPE: DNA
<213> ORGANISM: Artificial

```
<220> FEATURE:
<223> OTHER INFORMATION: CdtB-DN-V134R-F Primer

<400> SEQUENCE: 54
caagccgatg aagcttttat ccgacattct gattcttctg tgct                 44

<210> SEQ ID NO 55
<211> LENGTH: 44
<212> TYPE: DNA
<213> ORGANISM: Artificial
<220> FEATURE:
<223> OTHER INFORMATION: CdtB-DN-V134R-R Primer

<400> SEQUENCE: 55
agcacagaag aatcagaatg tcggataaaa gcttcatcgg cttg                 44

<210> SEQ ID NO 56
<211> LENGTH: 31
<212> TYPE: DNA
<213> ORGANISM: Artificial
<220> FEATURE:
<223> OTHER INFORMATION: Loop-F Primer

<400> SEQUENCE: 56
cgctcacaaa ttacaagtga ccactatcca g                               31

<210> SEQ ID NO 57
<211> LENGTH: 31
<212> TYPE: DNA
<213> ORGANISM: Artificial
<220> FEATURE:
<223> OTHER INFORMATION: Loop-R Primer

<400> SEQUENCE: 57
taactgattt aacattaagg cagcctggaa g                               31

<210> SEQ ID NO 58
<211> LENGTH: 11
<212> TYPE: PRT
<213> ORGANISM: Actinobacillus actinomycetemcomitans

<400> SEQUENCE: 58

Leu Met Leu Asn Gln Leu Arg Ser Gln Ile Thr
1               5                   10

<210> SEQ ID NO 59
<211> LENGTH: 11
<212> TYPE: PRT
<213> ORGANISM: Homo sapiens

<400> SEQUENCE: 59

Asn Gly Leu Ser Asp Gln Leu Ala Gln Ala Ile
1               5                   10
```

CHIMERA COMPRISING BACTERIAL CYTOTOXIN AND METHODS OF USING THE SAME

CROSS REFERENCE TO RELATED APPLICATIONS

This is a continuation-in-part of PCT Patent Application PCT/US2009/038740, filed Mar. 30, 2009, which claims priority to U.S. Provisional Patent Application 61/064,862, filed Mar. 31, 2008, both of which are incorporated by reference herein in their entirety.

FIELD OF THE INVENTION

The invention relates to recombinant polypeptides comprising a chimera that inhibits cell proliferation and a method of using the same.

BACKGROUND OF THE INVENTION

Over the last few decades there has been developing interest in non-traditional treatments for certain types of cancer. Recombinant toxins, hybrid proteins composed of a bacterial toxin and either a growth factor or a portion of a recombinant monoclonal antibody, have received significant attention in cancer therapeutics.

Human DNase I has been used as a therapeutic agent for the treatment of wounds and ulcers, bronchitis, inflammatory conditions, herpes infection and most notably, cystic fibrosis. The cytolethal distending toxin (Cdt) is a genotoxin, produced by several species of bacteria including the periodontal pathogen *Actinobacillus actinomycetemcomitans*.

Cytolethal distending toxin (Cdt) is a family of secreted bacterial protein holotoxins that classically arrest the growth of specific types of eukaryotic cells or cell lines at either the G0/G1 or G2/M phase of the cell cycle. The holotoxin is the product of three genes expressed by a handful of facultative or microaerophilic gram-negative pathogenic bacterial species. The species identified to date that express a biologically active CDT include select strains of enteropathogenic *Escherichia coli, Campylobacter jejuni, Campylobacter upsaliensis, Campylobacter coli, Shigella dysenteriae, Haemophilus ducreyi, Helicobacter hepaticus, Helicobacter flexispira, Helicobacter bilis, Helicobacter canis* and, the periodontal pathogen, *Actinobacillus actinomycetemcomitans*. Organization of the genetic locus as well as the structure and biological activity of the holotoxin are fairly well conserved among the bacterial genera that express the Cdt. Biologically active toxin is a heterotrimer composed of approximately 18-25 kDa (CdtA), 31 kDa (CdtB) and 21 kDa (CdtC) protein subunits expressed from a polycistronic operon. An adjunct property of the cdt genes is that they appear to have a eukaryotic rather than prokaryotic heritage. The cdt gene products exhibit deduced amino acid sequence and structure/function similarities (albeit weak) to those of eukaryotic proteins.

SUMMARY OF THE INVENTION

This invention provides, in one embodiment, a recombinant polypeptide comprising a chimera, wherein said chimera comprises a DNase I fragment or a homologue thereof and a Cdt fragment or a homologue thereof.

In another embodiment, the present invention provides a recombinant polynucleotide encoding a recombinant polypeptide comprising a chimera, wherein said chimera comprises a DNase I fragment or a homologue thereof and a Cdt fragment or a homologue thereof.

In another embodiment, the present invention provides a DNA vector comprising a recombinant polynucleotide encoding a recombinant polypeptide comprising a chimera, wherein said chimera comprises a DNase I fragment or a homologue thereof and a Cdt fragment or a homologue thereof.

In another embodiment, the present invention provides a plasmid comprising a recombinant polynucleotide encoding a recombinant polypeptide comprising a chimera, wherein said chimera comprises a DNase I fragment or a homologue thereof and a Cdt fragment or a homologue thereof.

In another embodiment, the present invention provides a method for inhibiting the proliferation of a neoplastic cell comprising the step of contacting said cell with a recombinant polypeptide comprising a chimera or a nucleic acid molecule encoding the same, wherein said chimera comprises a DNase I fragment or a homologue thereof and a Cdt fragment or a homologue thereof, thereby inhibiting the proliferation of a neoplastic cell.

In another embodiment, the present invention provides a method for treating a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby treating a neoplastic disease in a subject.

In another embodiment, the present invention provides a method for inhibiting or suppressing a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby inhibiting or suppressing a neoplastic disease in a subject.

In another embodiment, the present invention provides a method for reducing the symptoms associated with a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby reducing the symptoms associated with a neoplastic disease in a subject.

In another embodiment, the invention provides a composition comprising: a recombinant CdtA polypeptide comprising at least one of the mutations C149A and C178A, said polypeptide operably linked to a ligand that binds specifically to an antigen expressed on the surface of a cancerous epithelial cell type.

In another embodiment, the invention provides a recombinant CdtA polypeptide operably linked to a ligand that binds specifically to an antigen expressed on the surface of a cancerous epithelial cell type, wherein said recombinant CdtA polypeptide comprises at least one of the mutations C149A and C178A.

In another embodiment, the invention provides a chimeric CdtA polypeptide comprising at least one of the mutations C149A and C178A.

In another embodiment, the invention provides an isolated nucleic acid sequence encoding (i) a CdtA polypeptide comprising at least one of the mutations C149A and C178A or (ii) a nucleic acid sequence that is at least 85% identical to the sequence of (i).

In another embodiment, the invention provides a method for inhibiting the proliferation of a cancerous epithelial cell type comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, the invention provides a method for inhibiting the proliferation of a cancerous epithelial cell comprising: contacting said cell with a recombinant CdtA polypeptide comprising at least one of the mutations C149A and C178A, said polypeptide operably linked to a ligand that binds specifically to an antigen expressed on the surface of said cell.

In another embodiment, the invention provides a method for treating cancer comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, the invention provides a method for treating a disease associated with oral candidiasis comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, the invention provides a method for treating a disease associated with oral candidiasis comprising: administering a toxin composition specific to *Candida albicans*, said toxin composition comprising a recombinant CdtA polypeptide comprising at least one of the mutations C149A and C178A, said polypeptide operably linked to a ligand that binds specifically to an antigen expressed on the surface of a cancerous epithelial cell type.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

FIG. 1. Characterization of recombinant CdtB-$His_6$. (A) Sodium dodecyl sulfate-polyacrylamide gel electrophoresis of affinity purified recombinant *A. actinomycetemcomitans* CdtB-$His_6$. The gel is stained with Coomassie Brilliant Blue. (B) Dose response kinetics of the conversion of supercoiled (S) plasmid DNA to relaxed (R) and linear (L) forms by CdtB-$His_6$. Agarose gel stained with ethidium bromide. The activity of CdtB labeled with a histidine tag at the amino terminal end of the protein is compared at the highest concentration (1 μg/1 μg of DNA) of CdtB-$His_6$ tested. (C) Dose response kinetics of the activity of bovine DNase I.

FIG. 2. DNA nicking assay containing increasing concentrations of either $MgCl_2$ (top panel), $CaCl_2$ (middle panel) or $MnCl_2$ (bottom panel) in the standard reaction buffer. Supercoiled (S), relaxed (R) and linear (L) forms of DNA were quantified by densitometry of ethidium bromide stained agarose gels (insets). The data shown is representative of several repeat experiments FIG. 3. Heat liability of recombinant CdtB-$His_6$ and DNase I. (A) CdtB-$His_6$ heated for various periods in boiling water and then assayed for supercoiled DNA nicking activity. (B) bovine DNase I treated as in panel A. (C) effects of heating on the nicking activity of CdtB-DNase I and DNase I-CdtB. Numbers above gels lanes represent minutes. Abbreviations are the same as in FIG. 1.

FIG. 4. The effect of globular (G) actin on the supercoiled DNAs nicking activity of CdtB-$His_6$, bovine DNase I and the two hybrid proteins. Abbreviations are the same as in FIG. 1.

FIG. 5. (A) Computer models of the *A. actinomycetemcomitans* CdtB (as part of the Cdt heterotrimer) and bovine DNase I. (B) Theoretical model of the CdtB/DNase I hybrid protein construct. The CdtB (amino-terminal half) and DNase I (carboxy-terminal half) portions of the hybrid protein are shown in orange and magenta, respectively. The amino-(N) and carboxy (C)-termini are labeled. (C) Sequence alignment of the four His-tagged constructs (CdtB-H (SEQ ID NO: 16); CdtB/DNaseI (SEQ ID NO: 26); DNaseI/CdtB (SEQ ID NO: 27); human DNAse I (SEQ ID NO: 7)). Conserved and identical residues are marked by dots and asterisks, respectively. The blue and orange arrows mark the gene fusion position and predicted signal sequence cleavage sites, respectively Amino acid substitutions are marked in green and predicted functional domains are in red. Location of the nuclear localization signal (NLS) and information about the location of functional residues in DNase I was from Nishikubo et al. (2003) and Pan et al. (1998), respectively. Disulfides in DNase I are designated by brackets.

FIG. 6. The biological and binding activities of the hybrid proteins. (A) heterotoxins were reconstituted with wild-type CdtA and CdtC and each of the hybrid proteins. CHO cells were treated with the preparations. Colonies were fixed, stained and counted after growth for six days and expressed as colony-forming units (CFU). (B) Saturation binding kinetics of the two hybrid proteins were compared to that of CdtB-$His_6$. The same proteins were incubated with wild-type CdtA and CdtC in refolding buffer and subjected to differential dialysis. The reconstituted samples were examined before (BD) and after (AD) dialysis on a western blot (inset). (C) The stoichiometric binding of the two hybrid proteins to wild-type CdtA and CdtC immobilized on thyroglobulin was examined by ELISA. Numbers above the columns are absorbance ratios calculated as described in Methods. The hybrid proteins, and CdtB-$His_6$ as a control, were mixed with wild-type CdtA and CdtC, as in the differential dialysis experiment in the inset in panel A, and the reconstituted samples assayed for DNA nicking activity (inset). The reaction examined in the first lane contained non-complexed CdtB-$His_6$. Abbreviations are the same as in the legend for FIG. 1. Experiments were performed a minimum of three times. Mean values and standard deviations were plotted where appropriate.

FIG. 7. A computer models of CdtB (as part of the Cdt heterotrimer) and the two hybrid proteins. The α-helix H1 and large loop domains are labeled. Note that the orientation of the DNase I/CdtB structure is flipped 180° relative to that of CdtB/DNase I. The *A. actinomycetemcomitans* Cdt was modeled using the program UCSF Chimera version 1.2197 and PDB coordinate file 2F2F. The theoretical hybrid protein structures were generated with Modeller 9.1 and visualized with UCSF Chimera.

FIG. 8. Nuclease activity of CdtB/DNase $I^{mut5}$ was compared to that of CdtB-$His_6$ and the original CdtB/DNase I construct. The data is expressed as a percentage of the supercoiled (S) form DNA remaining after the reaction. These values were obtained by densitometry of ethidium bromide stained agarose gels (inset A). Semilogarithmic plot of the log of the substrate concentration [S] versus time of the reaction (expressed in minutes) for CdtB/DNase $I^{mut5}$ (inset B). [S] represents the amount of S-form DNA obtained by densitometry of the agarose gel in the inset). The control lacked enzyme. The data shown is representative of several repeat experiments.

FIG. 9 depicts a flow cytometry of untreated and Cdt-treated HeLa cells, the human cancer cell line CAL-27 and primary HGEC (AL-1). Cultures treated with Cdt received 10 μg of reconstituted recombinant protein/ml. Cell nuclei were prepared 36 h post-intoxication and were stained with propidium iodide. Quantitative values for the diploid G1, diploid G2 and S peaks are provided in Table 4.

FIG. 10 shows computer models of CdtB-His$_6$ and CdtB/DNase I$^{mut5}$ containing the large loop substitution. The amino- and carboxy-terminal halves of the proteins are in red and magenta, respectively. The α-helix H1 and large loop domains (yellow) are labeled. Distances are labeled in angstroms. The theoretical computer models were generated as described in the legend to FIG. 6.

Figure 11:
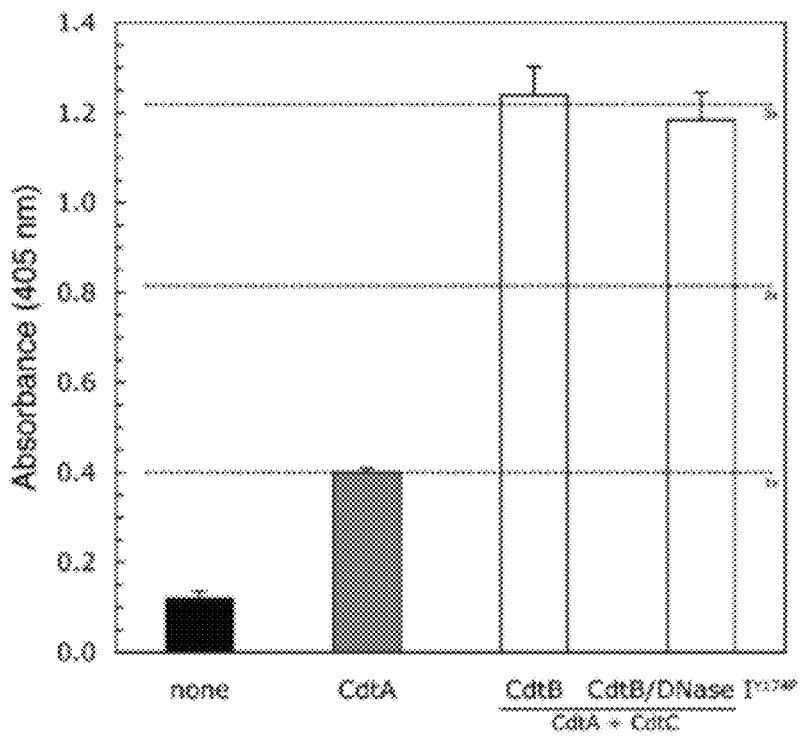

FIG. 11 is a bar graph showing wild-type and hybrid proteins that were added sequentially to CdtA pre-bound to thyroglobulin-coated 96-well plates. Bound protein was detected as described in the legend to FIG. 6C.

Figure 12:
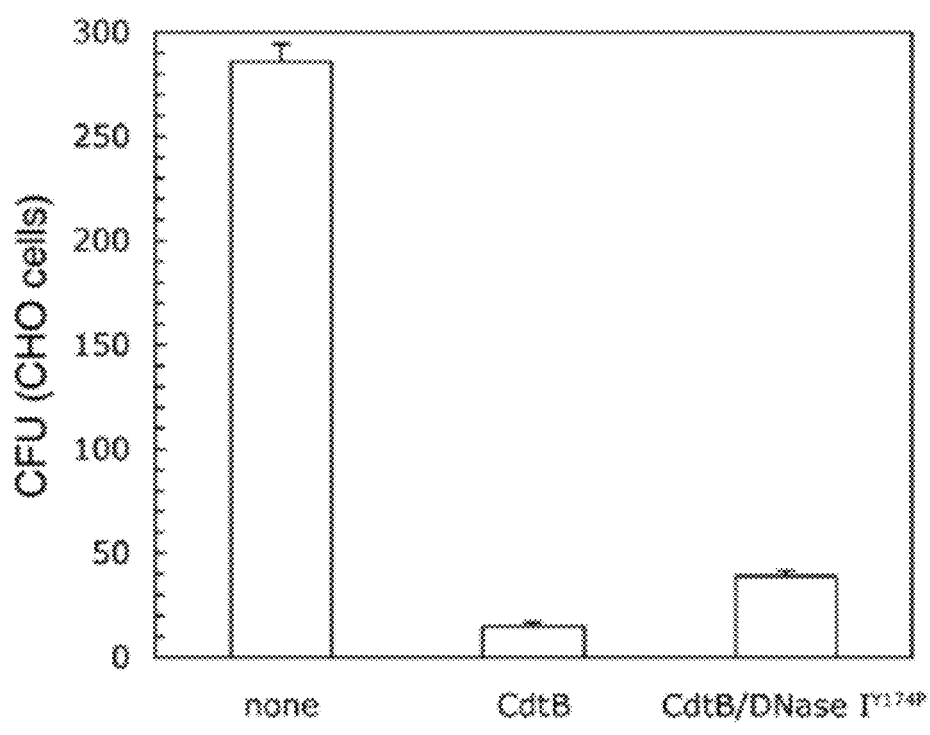

FIG. 12 is a bar graph showing heterotoxins that were reconstituted with wild-type CdtA, wild-type CdtC and either wild-type CdtB or CdtB/DNase IY174P (SEQ. ID NO: 14 and 15). CHO cells were treated with the preparations. Colonies were fixed, stained and counted after growth for six days and expressed as colony-forming units (CFU).

Figure 13:
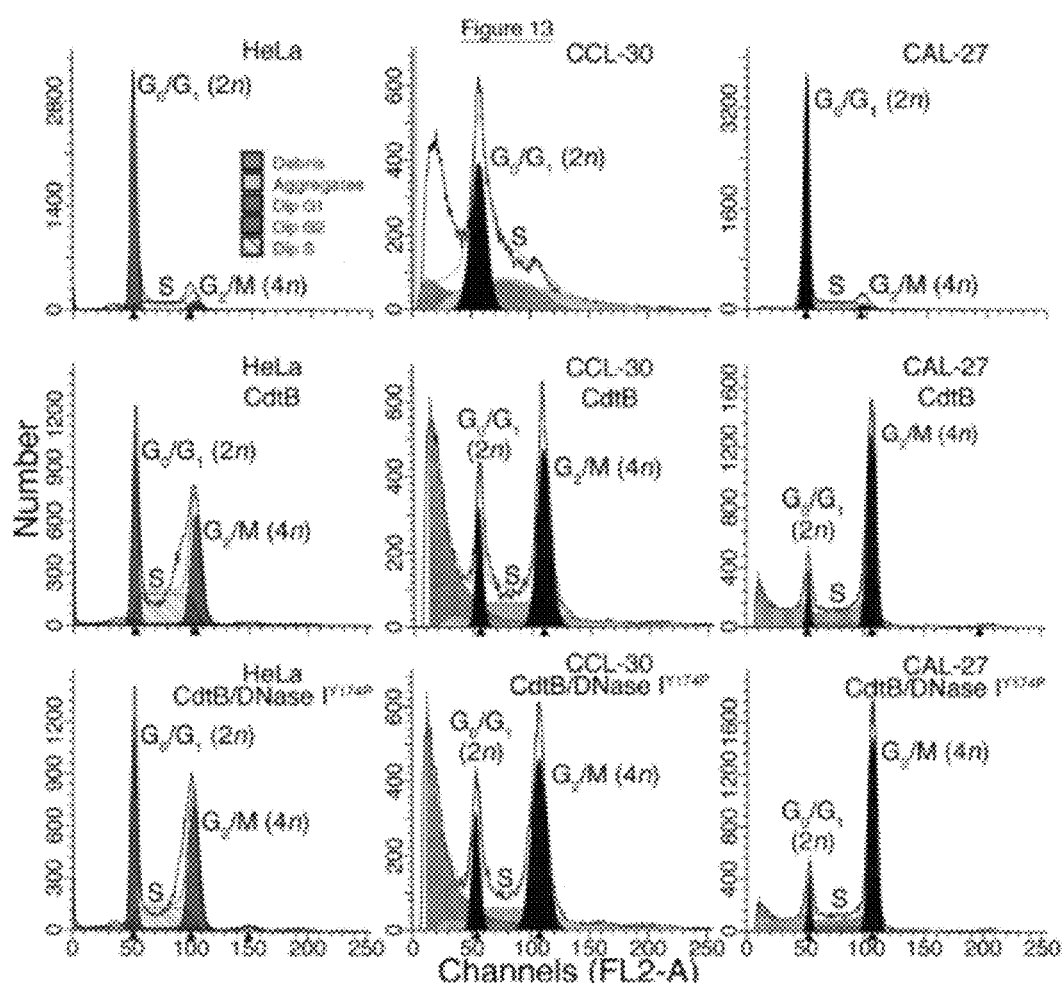

FIG. 13 depicts flow cytometry of HeLa, CCL-30 and CAL-27 cancer cell lines with heterotoxin containing CdtB or CdtB/DNase I$^{Y174P}$. Cultures treated with heterotoxin received 10 μg of reconstituted recombinant protein/ml. Cell nuclei were prepared 36 h post-intoxication and were stained with propidium iodide. Quantitative values for the diploid G1, diploid G2 and S peaks are provided in Table 5.

Figure 14:
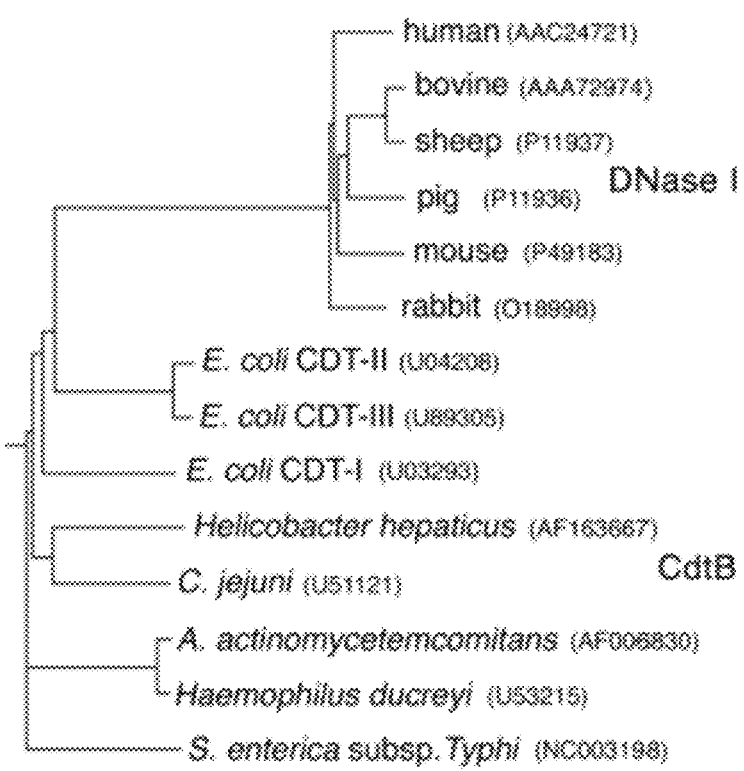

FIG. 14 is a phylogenetic tree showing the relationship of bacterial CdtB and mammalian DNase I deduced amino acid sequences. GenBank accession numbers are given in parentheses.

Figure 15:
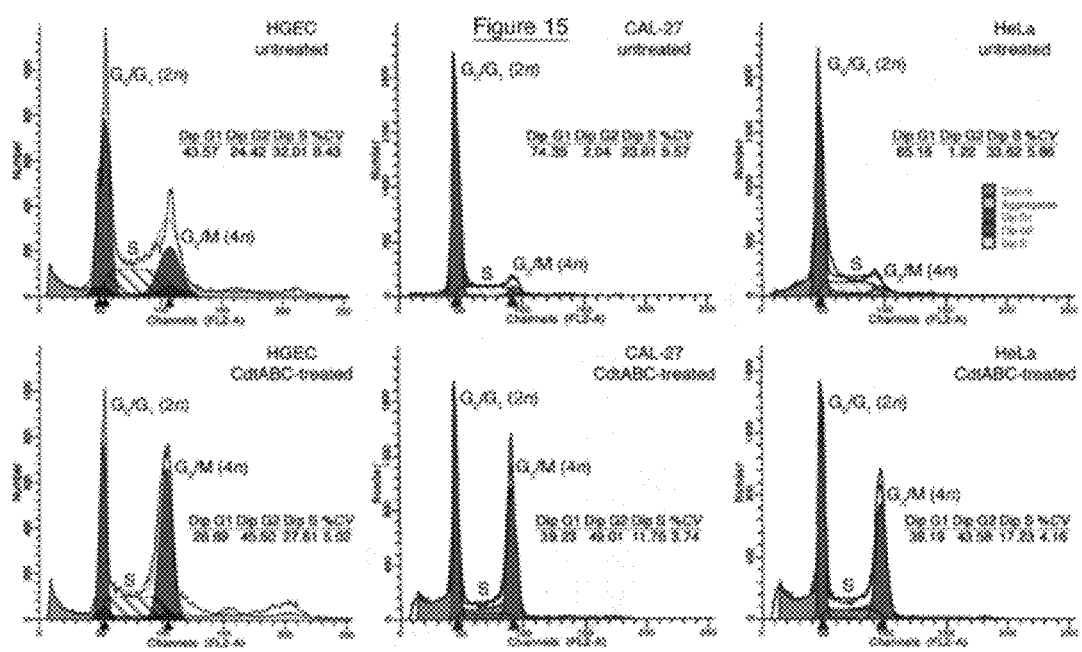

FIG. 15. Cell cycle arrest of epithelial cells following exposure to the Cdt. Cultures (24 h) of primary HGEC, CAL-27 (SCC) and HeLa cells were left untreated or treated with 10 μg/ml of reconstituted toxin (CdtABC-treated)/3.5×10$^6$ cells for 36 h. Propidium iodide stained nuclei were examined by flow cytometry. ModFit was used to generate the plots. The stained DNA profile is shown as the heavy line. The dark grey filled peaks designate the proportions of the cell population at the G0/G1 (2n) and G2/M (4n) interphases of the cell cycle. The diagonal line filled peak shows the S phase population. Quantitative values represent the percent of the total cell population that is diploid G1, diploid G2 and diploid S. The increase in the percent of the total cell population accumulated at the G2/M interphase, indicates that cell cycle arrest occurred in all three types of epithelial cells following exposure to the Cdt.

Figure 16:
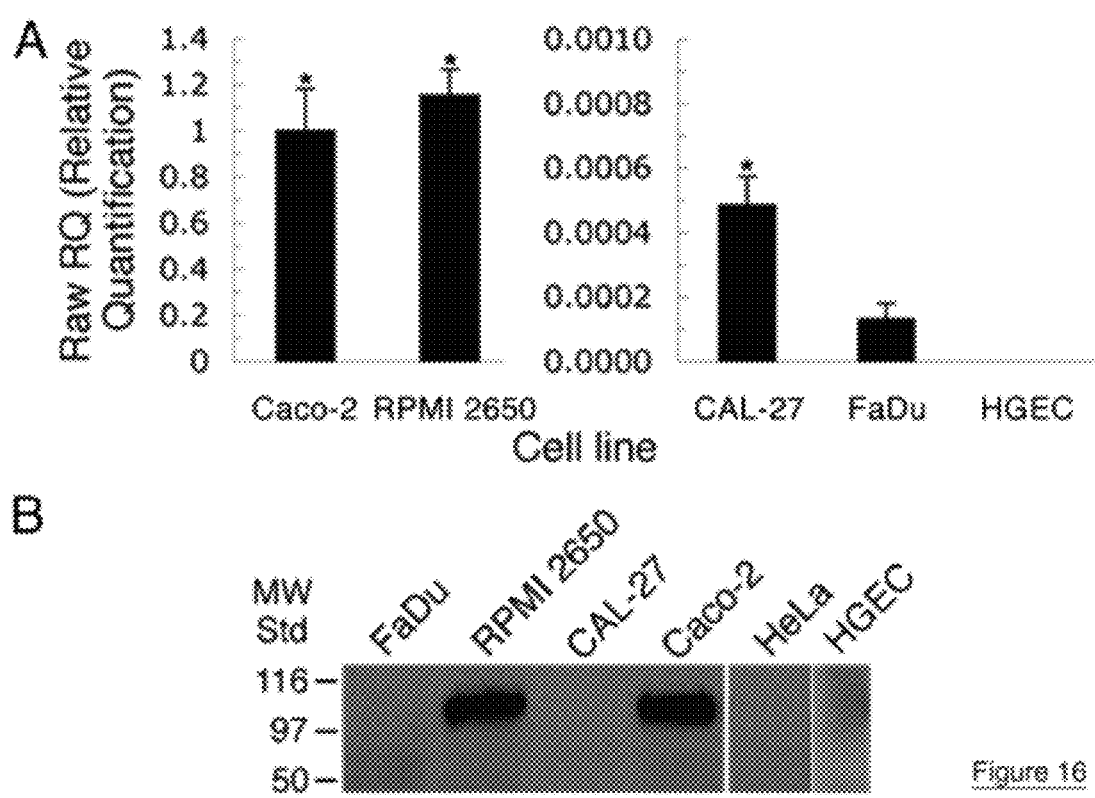

FIG. 16. Expression of the prominin-1 gene in epithelial cells. (A) Real time (RT)-PGR of prominin-1 mRNA from the SCC cell lines RPMI 2650, CAL-27 and FaDu and primary HGEC. PCR primers and conditions are described in Materials and Methods. Values for the amount of PCR amplicon were normalized to that for the ubiquitous, constitutively expressed TATA-binding protein (TBP) gene mRNA. Values were plotted relative to that for Caco-2 prominin-1 mRNA (positive control). The data were plotted on two scales to depict the large difference between levels of prominin-1 gene expression in the cell lines examined and are represented as mean values±SD; n=3 in each group. Asterisks mark statistically significant differences between the relative amount of the prominin-1 amplicon obtained from the particular SCC line mRNA and that from HGEC mRNA (no expression). Presence of CD133 in cell lysates of SCC cells assessed by western blotting. CD 133 was detected with an Enhanced Chemiluminescence Western Blotting Detection Kit (Amersham Pharmacia Biotech) after binding of CD 133/1 (AC133) mouse anti-human MAb (Miltenyi Biotec; 1:100) and horseradish peroxidase-conjugated anti-mouse IgG (Novagen; 1:3000). Prestained molecular weight standards were obtained from New England Biolabs.

Figure 17:
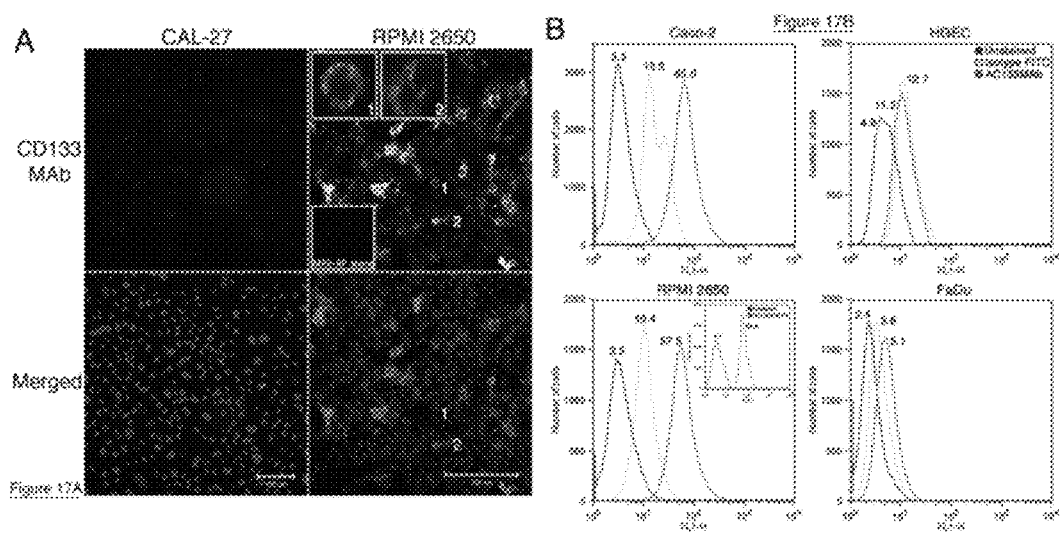
Figure 19A:
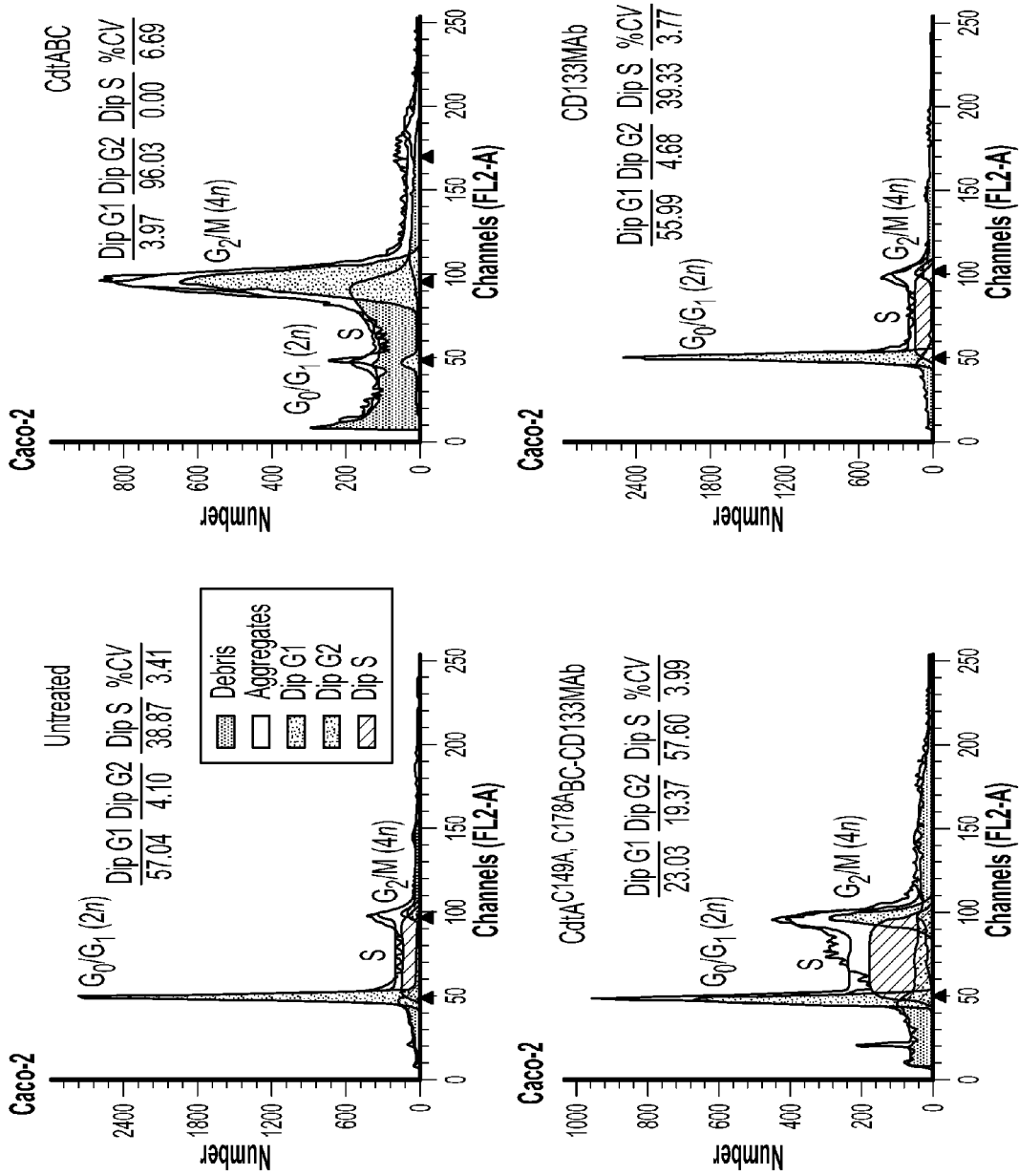
Figure 19B:
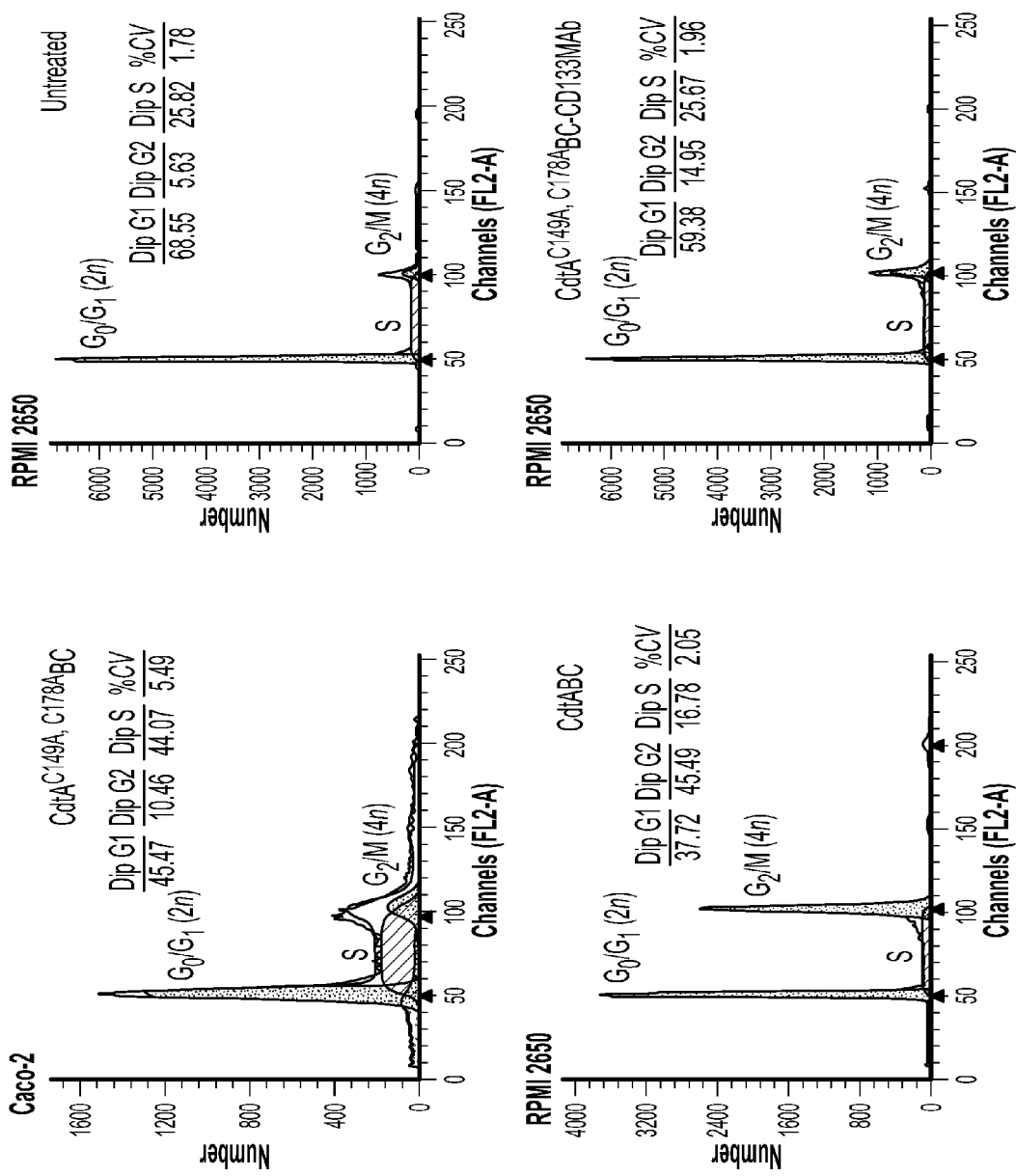
Figure 19C:
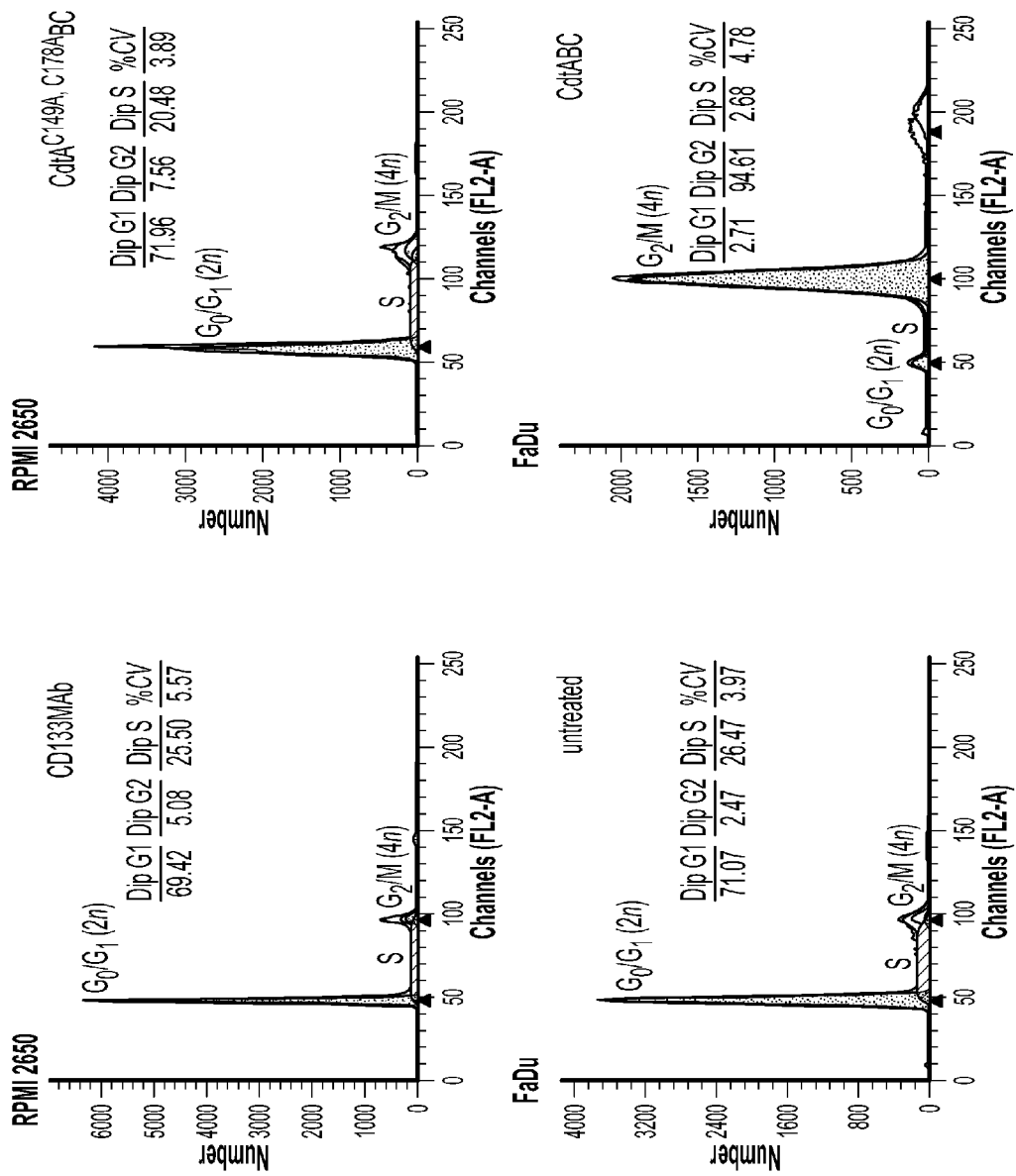
Figure 19D:
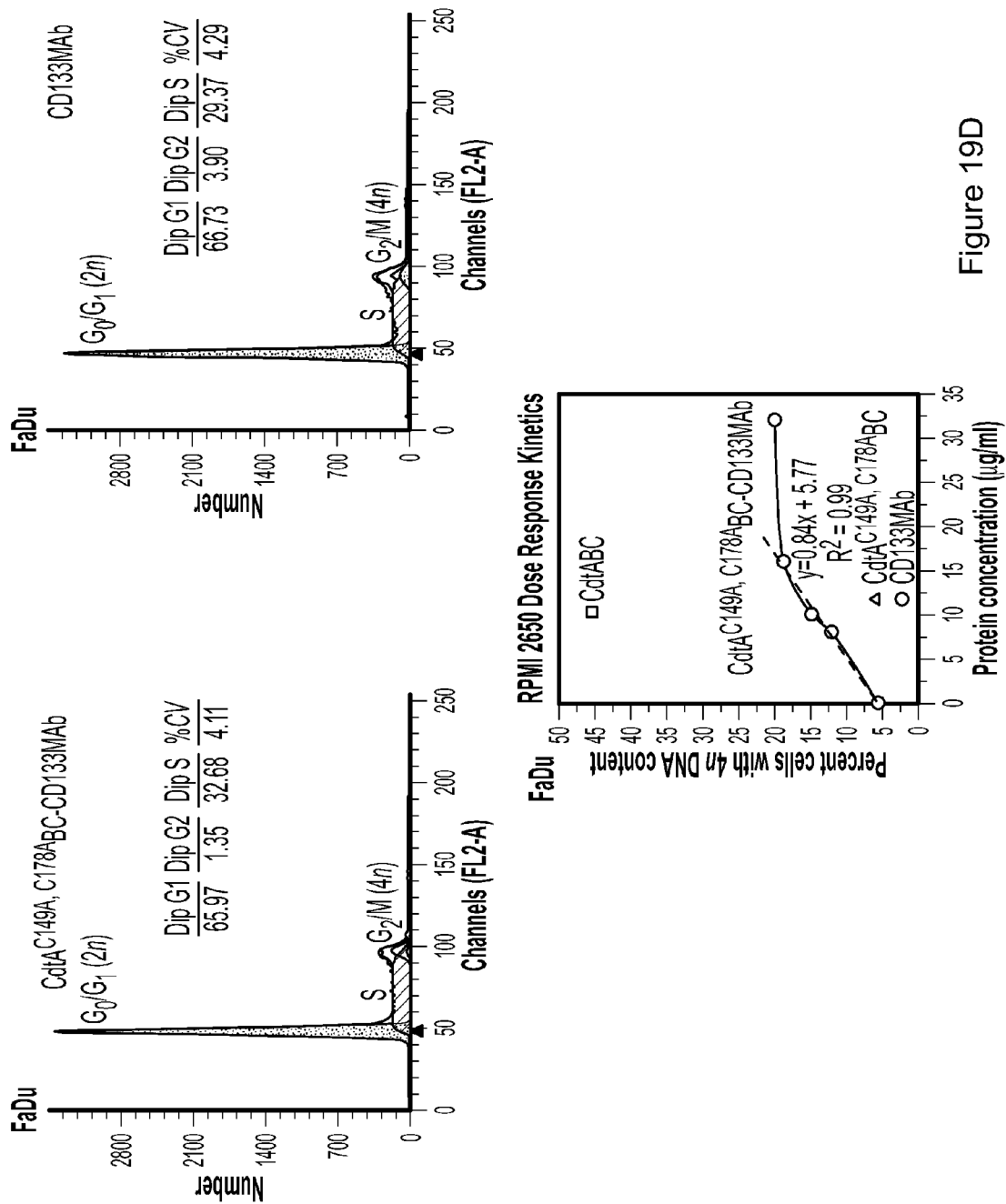

FIG. 17. Heterogeneous distribution of CD133$^+$ cells in SCC cell cultures. (A) CAL-27 and RPMI 2650 cells were stained with CD133/1 (AC133) mouse anti-human MAb (Miltenyi Biotec; 1:200) and goat anti-mouse IgG conjugated to Alexa Fluor (MAb-AF; Invitrogen/Molecular Probes®; 1:400). Nuclei were stained with DAPI (blue fluorescence). Slides were viewed with a Nikon Eclipse 80i fluorescence microscope. Magnification 20× (CAL-27) and 40× (RPMI 2650). Insets 1 and 2 show enlarged images of stained cells. (S) RPMI 2650, FaDu, Caco-2 and primary HGEC (1×10$^6$ cells) examined by flow cytometry after staining with 100 ug of purified AC 133.1 MAb IgG and Alexa Fluor 488 goat anti-mouse IgG (Invitrogen; 1:1000; red peaks) or Alexa Fluor 488 conjugate alone (1:1000; green peaks). Control cells were not stained (blue peaks). RPMI 2650 cells were also stained with mouse anti-human CD133/1 MAb conjugated to PE (Miltenyi Biotec; 1:100; inset; red peak). Gated runs were analyzed using FlowJo modeling software to obtain the plots. The number above each peak is the fluorescence value below which 50% of the events were found (median). The pronounced increase in fluorescence intensity and relatively high median value indicate binding of the AC133.1 MAb IgG and CD133.1 MAb-PE to RPMI 2650 and the positive control (Caco-2).

FIG. 18. Construction and characterization of a mutated CdtA subunit for targeting of prominin-1-expressing epithelial cells. (A) The crystal structure of the *A. actinomycetemcomitans* Cdt modeled with UCSF Chimera and PDB file 2F2F. Essential active site residues H160 and H274 in CdtB are shown in cyan. The four cysteine residues in the CdtA subunit are displayed in magenta. The surface model of CdtA (inset) is rotated 90° counterclockwise, relative to that in the ribbon structure, to show both surface exposed C149 and C197 residues. Two predicted disulfides C136/C149 and C178/C197 are marked by brackets and two site-directed mutations resulted in the substitutions C149A and C178A. AC133.1 MAb IgG was attached to the surface-exposed C197 of $CdtA^{c149A,C178A}$-$His_6$ via SMPT. (B) Binding kinetics of $CdtA^{c149A^{\wedge}C178A}$-HiS6 determined in a CELISA. Increasing concentrations of either wild-type CdtA-His6 or $CdtA^{c149A,C178A}$-$His_6$ were added to immobilized RPMI 2650 and FaDu cells. Bound protein was detected with an anti-His>>Tag monoclonal antibody (Novagen; 1:3000), anti-mouse IgG horseradish peroxidase (Novagen; 1:3000) and horseradish peroxidase substrate ABTS-100 (Rdckland). Plates were read at a wavelength of 405 nm in a Synergy 2 Microplate Reader (BjoTek Instruments, Inc.). Data are represented as mean values±SD; n=3 in each group. Statistically significant differences were found between the binding of the wild-type and mutated CdtA to RPMI 2650 (top asterisks) and FaDu (bottom asterisks). $P<0.05$. (C) Ability of $CdtA^{c149A,C178A}$-$His_6$ (relative to wild-type CdtA) to form a heterotrimer with wild-type CdtB and CdtC determined by differential dialysis. Aliquots of the reconstituted samples were examined on a western blot before (BD) and after (AD) dialysis. The proteins were detected by chemiluminescence after binding of anti-His<<Tag monoclonal antibody and horseradish peroxidase-conjugated anti-mouse IgG (Novagen; 1:3000).

FIG. 19. Effect of CdtA$^{c149A,c178A}$BC-CD133MAb on the cell cycle of SCC cells. Caco-2, RPMI 2650 and FaDu cultures (90% confluent) were treated with wild-type reconstituted recombinant Cdt (CdtABC), AC133.1 MAb IgG-conjugated Cdt (CdtA$^{c149A,C178A}$BC-CD133MAb), AC133.1 MAb IgG alone (CD133MAb) or unconjugated mutated Cdt (CdtA$^{c149A,C178A}$BC) for 36 h. Treated cultures received 10 μg/ml of protein/3.5×10$^6$ cells. No protein was added to untreated control cultures. DNA profiles of propidium iodide stained nuclei were obtained by flow cytometry and ModFit was used to construct the plots as described in the legend to FIG. 1. An increase in the percentage of the total cell population accumulated at the G2/M interphase was observed in RPMI 2650 cultures treated with wild type Cdt and CdtA$^{c149A,c178A}$BC-CD133MAb. Similar results were obtained with Caco-2. In the same experiment, RPMI 2650 cultures were exposed to increasing concentrations of CdtA$^{c149A,c178A}$BC-CD133MAb for 36 h and examined by flow cytometry. The percentage of cells in each treated culture having a 4n DNA concentration (diploid G2) was plotted against the concentration of the Cdt-MAb conjugate to obtain a dose response curve (last panel). The dose response was linear (dashed line) up to 16 ug/ml of protein/1×10$^6$ cells (at time of toxin addition). The linear regression equation and R-squared value (square of the correlation coefficient) are shown.

Figure 20:
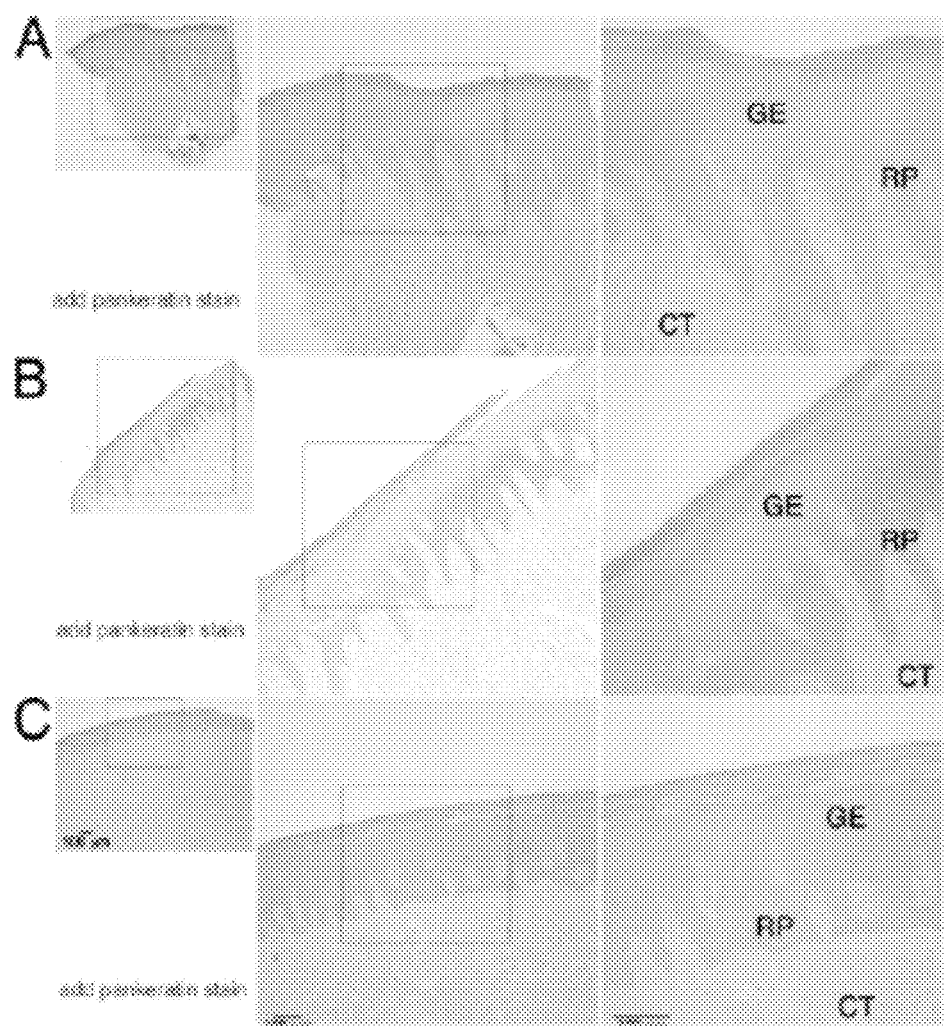

FIG. 20. Stability of untreated gingival tissue in vitro. Explants were incubated in tissue culture medium at 37° C. in an atmosphere containing 10% $CO_2$ for (A) 0 h, (B) 18 h and (C) 24 h. After incubation the tissue was embedded and representative sections were stained with hematoxylin and eosin. Sections are shown at 4, 10 and 20× magnification. The red outline marks the enlarged area. GE, gingival epithelium; RP, rete pegs; CT, connective tissue. Sections were also incubated with pan-keratin Ab3 mouse monoclonal antibody followed by goat anti-mouse Alexa Fluor 488 to detect epithelial cells (green fluorescence).

Figure 21:
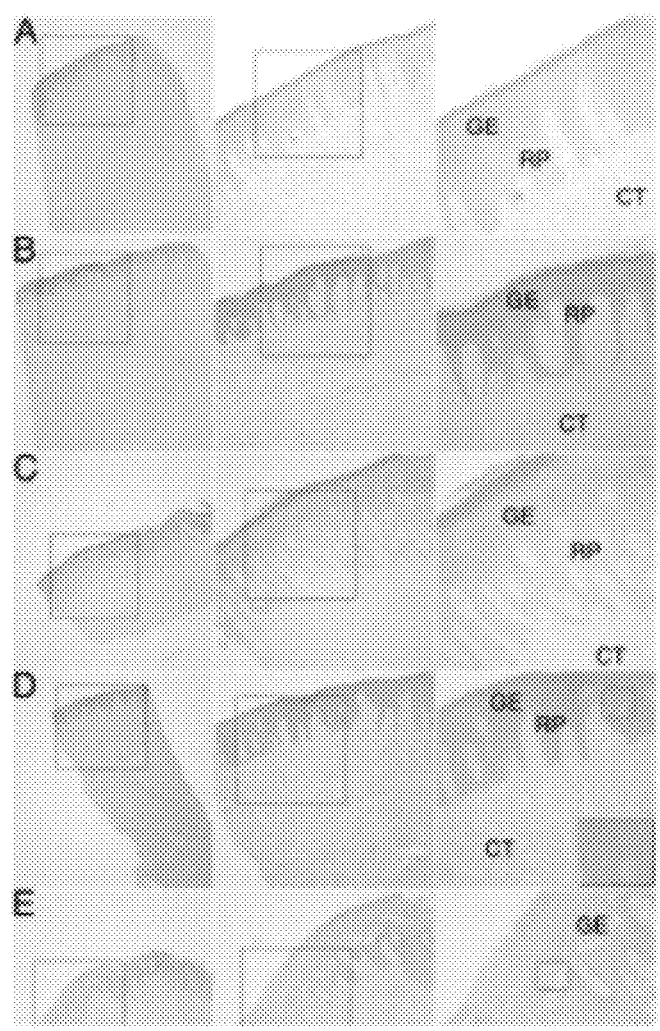

FIG. 21. Effects of Cdt on the integrity of gingival tissue. Explants were treated with 10 μg/ml of CdtAB$^{H160A}$C for (A) 0 h, (B) 18 h and (C) 36 h. Additional explants were treated with CdtABC: (D) 10 μg/ml for 0 h, (E) 10 μg/ml for 18 h and (F) 5 μg/ml for 36 h. Sections were stained with hematoxylin and eosin and depicted as described in the legend for FIG. 20. The insets are enlarged areas bounded by the small red outlines in the same images.

Figure 22:
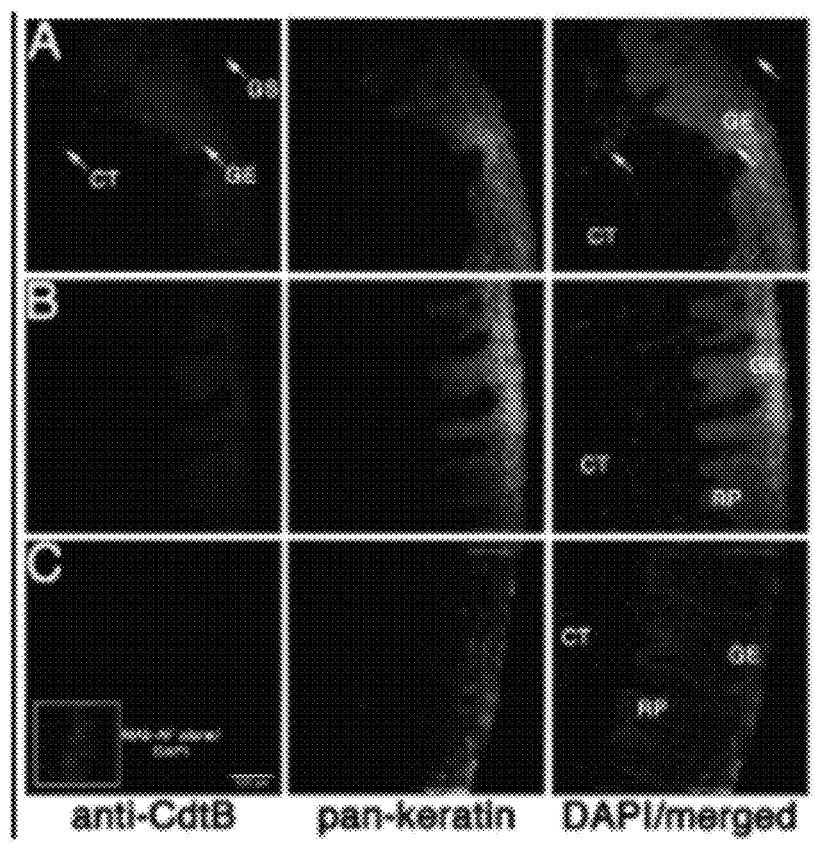

FIG. 22. Localization of CdtB in tissue treated with Cdt. Explants were incubated in tissue culture medium for 19 h. (A) Tissue treated with 10 μg/ml of CdtABC, (B) Tissue treated with 10 μg/ml of CdtAB$^{H160A}$C, (C) Untreated. The same sections were incubated with both pan-keratin Ab3 mouse antibody and rabbit anti-CdtB antibody followed by goat anti-mouse Alexa Fluor 488 (green fluorescence) and goat anti-rabbit IgG Alexa Fluor 594 conjugate (red fluorescence). Cell nuclei were visualized with DAPI (blue fluorescence). GS, gingival surface; GE, gingival epithelium; RP, rete pegs; CT, connective tissue. The arrows in (A) show CdtB in the various tissue layers. The inset in (C) is a tissue section stained only with the goat anti-mouse Alexa Fluor 488 conjugate and DAPI.

Figure 23:
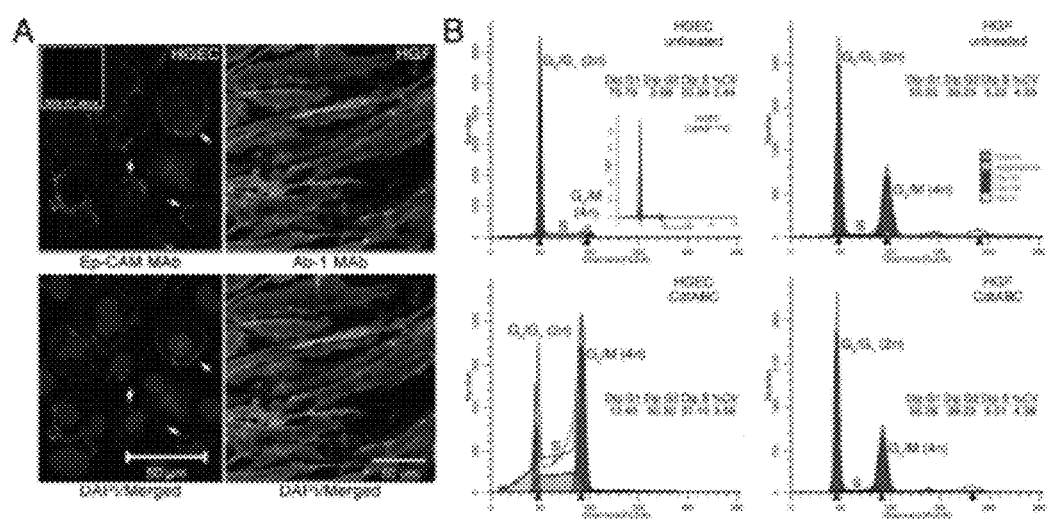

FIG. 23. Effect of Cdt on cultured primary HGEC and HGF. (A) HGEC incubated with mouse anti-human Ep-Cam (EBA-1) antibody and HGF treated with anti-fibroblast CD90/Thy-1 antigen (Ab-1) antibody. Both preparations were then stained with Alexa Fluor 488 goat anti-mouse IgG conjugate (green fluorescence). Nuclei were stained with DAPI. The arrows show the presence of Ep-CAM on the cell surface. The inset shows cells stained only with the goat anti-mouse Alexa Fluor 488 conjugate. (B) Flow cytometry of HGEC untreated and treated with 2.5 μg/ml of CdtABC for 36 h. The inset shows HGEC treated with 10 μg/ml of CdtAB$^{H160A}$C for 36 h. HGF were untreated and treated with 10 μg/ml of CdtABC for 96 h.

DETAILED DESCRIPTION OF THE INVENTION

The invention relates to recombinant polypeptides comprising a chimera that inhibits cell proliferation and a method of using the same.

The invention provides, in one embodiment, a recombinant polypeptide comprising a chimera, wherein said chimera comprises a DNase I fragment and a Cdt fragment. In another embodiment, the chimera comprises a DNase I fragment and a homologue of a Cdt fragment. In another embodiment, the chimera comprises a homologue of a DNase I fragment and a Cdt fragment. In another embodiment, the chimera comprises a homologue of a DNase I fragment and a homologue of a Cdt fragment. In another embodiment, the present invention provides a recombinant polypeptide comprising a chimera, wherein said chimera comprises a DNase I fragment or a homologue thereof and a Cdt fragment or a homologue thereof. In another embodiment, said chimera comprises a Cdt subunit.

In one embodiment, DNase I is an endonuclease that non-specifically cleaves DNA to release di-, tri- and oligonucleotide products with 5'-phosphorylated and 3'-hydroxylated ends. In one embodiment, DNase I acts on single- and double-stranded DNA, chromatin and RNA: DNA hybrids. In one embodiment, DNase I for use in the compositions and methods of the present invention is derived from humans. In one embodiment, DNase I for use in the compositions and methods of the present invention is derived from a murine species, which in one embodiment, is rat or mouse. In one embodiment, DNase I for use in the compositions and methods of the present invention is derived from *Mus musculus, Homo sapiens, Bos taurus, Bacillus subtilis, Rattus norvegicus, Oryctolagus cuniculus, Salmo salar, Gallus gallus, Canis lupus familiaris, Rhodopirellula baltica* SH 1, *Sus scrofa, Equus caballus, Dictyostelium discoideum, Pseudomonas putida* GB-1, *Pseudomonas putida* W619, *Azoarcus* sp. BH72, *Synechococcus* sp., *Bacteroides caccae* ATCC 43185, *Xenopus laevis*, or *Aspergillus niger*.

In one embodiment, a DNase I fragment of the present invention is an N-terminal fragment. In another embodiment, a DNase I fragment of the present invention is a C-terminal fragment.

In one embodiment, the nucleic acid sequence encoding the DNase I fragment is: TTGTACAAAAAAGCAGGCT-TGGAAGGAGTTCGAACCATGAGGGGCAT-GAAGCTGCTG GGGGCGCTGCTGGCACTGGCGGC-CCTACTGCAGGGGGCCGTGTCCCTGAAGATCGCA GCCTTCAACATCCAGACATTTGGG-GAGACCAAGATGTCCAATGCCACCCTCGTCAGCT ACATTGTGCAGATCCTGAGCCGCTATGA-CATCGCCCTGGTCCAGGAGGTCAGAGACAG CCAC-CTGACTGCCGTGGGGAAGCTGCTGGA-CAACCTCAATCAGGATGCACCAGACAC CTATCACTACGTGGTCAGTGAGC-CACTGGGACGGAACAGCTATAAGGAGCGCTACCT GTTCGTGTACAGGCCTGACCAGGTGTCT-GCGGTGGACAGCTACTACTACGATGATGGC TGC-GAGCCCTGCGGGAACGACACCTTCAAC- CGAGAGCCAGCCATTGTCAGGTTCTTCTCCCGGTTCACAGAGGTCAGGGAGTTTGCCATTGTTCCCCTGCATGCGGCCCCGGGGGACGCAGTATCCGAGATCGACGCTCTCTATGACGTCTACCTGGATGTCCAAGAGAAATGG GGCTTGGAGGACGTCATGTTGATGGGCGACTTCAATGCGGGCTGCAGCTATGTGAGACCCTCCCAGTGGTCATCCATCCGCCTGTGGACAAGCCCCACCTTCCAGTGGCTGATCCC CGACAGCGCTGACACCACAGCTACACCCACGCACTGTGCCTATGACAGGATCGTGGTTGCAGGGATGCTGCTCCGAGGCGCCGTTGTTCCCGACTCGGCTCTTCCCTTTAACTTCCAGGCTGCCAATGGCCTGAGTGACCAACTGGCCCAAGCCATCAGTGACCACTATCCAGTG GAGGTGATGCTGAAGTAGCTCGAGTGCGGCCGCAACCCAGCTTTCTTGTAC (SEQ ID NO: 1). In one embodiment, the coding sequence of the nucleic acid sequence is underlined. In another embodiment, the DNase I fragment is a homologue of SEQ ID NO: 1. In another embodiment, the DNase I fragment is a variant of SEQ ID NO: 1. In another embodiment, the DNase I fragment is an isoform of SEQ ID NO: 1. In another embodiment, the DNase I fragment is a fragment of SEQ ID NO: 1. Each possibility represents a separate embodiment of the present invention.

In another embodiment, the nucleic acid sequence encoding the DNase I fragment is: ATGAGGGGCATGAAGCTGCTGGGGGCGCTGCTGGCACTGGCGGCCTACTGCAGGGG
GCCGTGTCCCTGAAGATCGCAGCCTTCAACATCCAGACATTTGGGGAGACCAAGATGT CCAATGCCACCCTCGTCAGCTACATTGTGCAGATCCTGAGCCGCTATGACATCGCCCT GGTCAGGAGGTCAGAGACAGCCACCTGACTGCCGTGGGGAAGCTGCTGGACAACCT CAATCAGGATGCACCAGACACCTATCACTACGTGGTCAGTGAGCCACTGGGACGGAA CAGCTATAAGGAGCGCTACCTGTTCGTGTACAGGCCTGACCAGGTGTCTGCGGTGGAC AGCTACTACTACGATGATGGCTGCGAGCCCTGCGGGAACGACACCTTCAACCGAGAG CCAGCCATTGTCAGGTTCTTCTCCCGGTTCACAGAGGTCAGGGAGTTTGCCATTGTTCC CCTGCATGCGGCCCCGGGGGACGCAGTATCCGAGATCGACGCTCTCTATGACGTCTAC CTGGATGTCCAAGAGAAATGGGGCTTGGAGGACGTCATGTTGATGGGCGACTTCAATG CGGGCTGCAGCTATGTGAGACCCTCCCAGTGGTCATCCATCCGCCTGTGGACAAGCCC CACCTTCCAGTGGCTGATCCCCGACAGCGCTGACACCACAGCTACACCCACGCACTGT GCCTATGACAGGATCGTGGTTGCAGGGATGCTGCTCCGAGGCGCCGTTGTTCCCGACT CGGCTCTTCCCTTTAACTTCCAGGCTGCCAATGGCCTGAGTGACCAACTGGCCCAAGC CAT CAGTGACCACTATCCAGTGGAGGTGATGCTGAAGTAG (SEQ ID NO: 2). In another embodiment, the DNase I fragment is a homologue of SEQ ID NO: 2. In another embodiment, the DNase I fragment is a variant of SEQ ID NO: 2. In another embodiment, the DNase I fragment is an isoform of SEQ ID NO: 2. In another embodiment, the DNase I fragment is a fragment of SEQ ID NO: 2. Each possibility represents a separate embodiment of the present invention.

In another embodiment, the nucleic acid sequence encoding the DNase I fragment is: ATGGTGAGGGGAATGAAGCTGCTGGGGGCGCTGCTGGCACTGGCGGCCCTACTGCAG
GGGGCCGTGTCCCTGAAGATCGCAGCCTTCAACATCCAGACATTTGGGGAGACCAAG ATGTCCAATGCCACCCTCGTCAGCTACATTGTGCAGATCCTGAGCCGCTATGACATCGCCCTGGTCCAGGAGGTCAGAGACAGCCACCTGACTGCCGTGGGGAAGCTGCTGGACAACCTCAATCAGGATGCACCAGACACCTATCACTACGTGGTCAGTGAGCCACTGGGACGGAACAGCTATAAGGAGCGCTACCTGTTCGTGTACAGGCCTGACCAGGTGTCTGCGGTGGACAGCTACTACTACGATGATGGCTGCGAGCCCTGCGGGAACGACACCTTCAACCGA GAGCCAGCCATTGTCAGGTTCTTCTCCCGGTCACAGAGGTCAGGGAGTTTGCCATTGTTCCCCTGCATGCGGCCCCGGGGGACGCAGTAGCCGAGATCGACGCTCTCTATGACGT CTACCTGGATGTCCAAGAGAAATGGGGCTTGGAGGACGTCATGTTGATGGGCGACTTCAATGCGGGCTGCAGCTATGTGAGACCCTCCCAGTGGTCATCCATCCGCCTGTGGACAAGCCCCACCTTCCAGTGGCTGATCCCCGACAGCGCTGACACCACAGCTACACCCACGCA CTGTGCCTATGACAGGATCGTGGTTGCAGGGATGCTGCTCCGAGGCGCCGTTGTTCCCGACTCGGCTCTTCCCTTTAACTTCCAGGCTGCCAATGGCCTGAGTGACCAACTGGCCCAAGCCATCAGTGACCACTATCCAGTGGAGGTGATGCTGAAGCTCGAGCACCACCACCACCACCACCATATGCTCGAGGATCCGGCTGCTAACAAAGCC (SEQ ID NO: 3). In another embodiment, the DNase I fragment is a homologue of SEQ ID NO: 3. In another embodiment, the DNase I fragment is a variant of SEQ ID NO: 3. In another embodiment, the DNase I fragment is an isoform of SEQ ID NO: 3. In another embodiment, the DNase I fragment is a fragment of SEQ ID NO: 3. Each possibility represents a separate embodiment of the present invention.

In another embodiment, the amino acid sequence encoding the DNase I fragment is: MRGMKLLGALLALAALLQGAVSLKIAAFNIQTFGETKMSNATLVSYIVQILSRYDIALVQE VRDSHLTAVGKLLDNLNQDAPDTYHYVVSEPLGRNSYKERYLFVYRPDQVSAVDSYYYDDGCEPCGNDTFNREPAIVRFFSRFTEVREFAIVPLHAAPGDAVSEIDALYDVYLDVQEKWG LEDVMLMGDFNAGCSYVRPSQWSSIRLWTSPTFQWLIPDSADTTATPTHCAYDRIVVAGMLLRGAVVPDSALPFNFQAANGLSDQLAQAISDHYPVEVMLK (SEQ ID NO: 4). In another embodiment, the DNase I fragment is a homologue of SEQ ID NO: 4. In another embodiment, the DNase I fragment is a variant of SEQ ID NO: 4. In another embodiment, the DNase I fragment is an isoform of SEQ ID NO: 4. In another embodiment, the DNase I fragment is a fragment of SEQ ID NO: 4. Each possibility represents a separate embodiment of the present invention.

In another embodiment, the amino acid sequence encoding the DNase I fragment is: MVRGMKLLGALLALAALLQGAVSLKIAAFNIQTFGETKMSNATLVSYIVQILSRYDIALVQ EVRDSHLTAVGKLLDNLNQDAPDTYHYVVSEPLGRNSYKERYLFVYRPDQVSAVDSYYY DDGCEPCGNDTFNREPAIVRFFSRFTEVREFAIVPLHAAPGDAVAEIDALYDVYLDVQEKW GLEDVMLMGDFNAGCSYVRPSQWSSIRLWTSPTFQWLIPDSADTTATPTHCAYDRIVVAG MLLRGAVVPDSALPFNFQAANGLSDQLAQAISDHYPVEVMLKLEHHHHHHHMLEDPAAN KA (SEQ ID NO: 5). In another embodiment, the DNase I fragment is a homologue of SEQ ID NO: 5. In another embodiment, the DNase I fragment is a variant of SEQ ID NO: 5. In another embodiment, the DNase I fragment is an isoform of SEQ ID NO: 5. In another embodiment, the DNase I fragment is a fragment of SEQ ID NO: 5. Each possibility represents a separate embodiment of the present invention.

In another embodiment, the amino acid sequence encoding the DNase I fragment is: MVRGMKLLGALLALAALLQ-GAVSLKIAAFNIQTFGETKMSNATLVSYIVQIM-SRYDIALVQ EVRDSHLTAVGKLLDNLNQDAPDTY-HYVVSEPLGRNSYKERYLFVYRPDQVSAVDSYYY DDGCEPCGNDTFNREPAIVRFFSR-FTEVREFAIVPLHAAPGDAVAEIDALYDVYLDVQEKW GLEDVMLMGDFNAGCSYVRPSQWSSIRL-WTSPTFQWLIPDSADTTATPTHCAYDRIVVAG MLLR-GAVVPDSALPFNFQAANGLSDQLAQAIS-DHYPVEVMLKLEHHHHHHHMLEDPAAN KA (SEQ ID NO: 6). In another embodiment, the DNase I fragment is a homologue of SEQ ID NO: 6. In another embodiment, the DNase I fragment is a variant of SEQ ID NO: 6. In another embodiment, the DNase I fragment is an isoform of SEQ ID NO: 6. In another embodiment, the DNase I fragment is a fragment of SEQ ID NO: 6. Each possibility represents a separate embodiment of the present invention.

In another embodiment, the amino acid sequence encoding the DNase I fragment is: MVRGMKLLGALLALAALLQ-GAVSLKIAAFNIQTFGETKMSNATLVSYIVQIM-SRYDIALVQ EVRDSHLTAVGKLLDNLNQDAPDTY-HYVVSEPLGRNSYKERYLFVYRPDQVSAVDSYYY DDGCEPCGNDTFNREPAIVRFFSR-FTEVREFAIVPLHAAPGDAVAEIDALYDVYLDVQEKW GLEDVMLMGDFNAGCSYVRPSQWSSIRL-WTSPTFQWLIPDSADTTATPTHCAYDRIVVAG MLLR-GAVVPDSALPFNFQAANGLSDQLAQAIS-DHYPVEVMLKLEHHHHHHHMLEDPAAN KA (SEQ ID NO: 7). In another embodiment, the DNase I fragment is a homologue of SEQ ID NO: 7. In another embodiment, the DNase I fragment is a variant of SEQ ID NO: 7. In another embodiment, the DNase I fragment is an isoform of SEQ ID NO: 7. In another embodiment, the DNase I fragment is a fragment of SEQ ID NO: 7. Each possibility represents a separate embodiment of the present invention.

In another embodiment, a DNase I, or its fragment or homologue comprises a mutated form of a DNase I. In another embodiment, a DNase I, or its fragment or homologue comprises a mutated form of a DNase I fragment. In another embodiment, a mutated DNase I, a mutated DNase I fragment comprises a deletion mutation. In another embodiment, a mutated DNase I, a mutated CdtB toxin fragment comprises an insertion mutation. In another embodiment, a mutated DNase I, a mutated DNase I fragment comprises a substitution mutation.

In one embodiment, a chimera of the present invention comprises a DNase fragment. In another embodiment, a chimera of the present invention comprises a nuclease fragment. In another embodiment, a chimera of the present invention comprises an RNase fragment.

In one embodiment, a DNase for use in the compositions and methods of the present invention is an exodeoxyribonuclease, and, in one embodiment, cleaves only residues at the ends of DNA molecules. In another embodiment, a DNase for use in the compositions and methods of the present invention is an endodeoxyribonuclease, and, in one embodiment, cleaves anywhere along the polynucleotide chain. In one embodiment, a DNase for use in the compositions and methods of the present invention is deoxyribonuclease I or, in another embodiment, deoxyribonuclease II.

In another embodiment, the chimera provided herein is a Cdt-DNase I chimera. In another embodiment, the chimera provided herein is a multimeric chimera protein comprising DNase I or its fragment or homologue; and a Cdt toxin, or its fragment or homologue. In another embodiment, the chimera provided herein comprises DNase I or its fragment or homologue; and a Cdt toxin. In another embodiment, the chimera provided herein is a multimeric chimera protein comprising DNase I and a Cdt toxin, or its fragment or homologue. In another embodiment, the chimera provided herein consists DNase I or its fragment or homologue; and a Cdt toxin.

In one embodiment, a Cdt fragment of the present invention is an N-terminal fragment. In another embodiment, a Cdt fragment of the present invention is a C-terminal fragment.

In one embodiment, a CdtA, CdtB, CdtC, Cdt holotoxin, or fragment thereof used in the compositions and methods of the present invention is derived from *Escherichia coli, Campylobacter jejuni, Campylobacter upsaliensis, Campylobacter coli, Shigella dysenteriae, Haemophilus ducreyi, Helicobacter hepaticus, Helicobacter flexispira, Helicobacter bilis, Helicobacter canis, Aggregatibacter actinomycetemcomitans*, or *Actinobacillus actinomycetemcomitans*.

In one embodiment, the Cdts are a family of heat-labile protein cytotoxins produced by several different bacterial species including diarrheal disease-causing enteropathogens such as some *Escherichia coli* isolates, *Campylobacter jejuni, Shigella* species, *Haemophilus ducreyi* and *Actinobacillus actinomycetemcomitans*. Thus, in one embodiment, a Cdt subunit of the present invention is derived from *Actinobacillus actinomycetemcomitans*. In another embodiment, a Cdt subunit of the present invention is derived from *Escherichia coli* isolates, *Campylobacter jejuni, Shigella* species, or *Haemophilus ducreyi*.

Cdts are encoded by three genes, designated cdtA, cdtB, and cdtC which are arranged as an apparent operon. These three genes specify three polypeptides designated CdtA, CdtB and CdtC with apparent molecular masses of 28, 32 and 20 kDa, respectively, that form a heterotrimeric holotoxin. Several cell lines and cell types have been shown to be sensitive to Cdt including human lymphoid cells, fibroblasts, human embryonic intestinal epithelial cells, a human colon carcinoma cell line, and human keratinocytes, among others. In one embodiment, lymphocytes are the most sensitive (4-5 fold) to Cdt, suggesting that Cdt most likely functions as an immunotoxin. In response to Cdt, proliferating cells exhibit G2 arrest and eventually cell death resulting from activation of the apoptotic cascade. In another embodiment, the cell cycle arrest results in a cessation of cell division. In one embodiment, the Cdts produce other effects, including, in another embodiment, progressive cellular distention.

The heterotrimeric Cdt holotoxin functions as an AB2 toxin where CdtB is the active (A) unit, and the complex of CdtA and CdtC comprise the binding (B) unit. In one embodiment, the CdtA and CdtC subunits are involved in the adhesion to target cells. In one embodiment, CdtA and CdtC are required for the toxin to associate with lipid microdomains within lymphocyte membranes. In one embodiment, the CdtC subunit interacts specifically with cholesterol. In one embodiment, the CdtB must be internalized and associate with cellugyrin, a microvessicle associated protein, in order to induce cell cycle arrest. In one embodiment, CdtB acts as a PIP3 phosphatase depleting cells of PIP3 and thereby blocking the Akt survival/proliferation pathway. In one embodiment, CdtB does not act on phosphatides or proteins. In one embodiment, the Cdt holotoxin has structural homology with inositol polyphosphate 5-phosphatase. In another embodiment, the CdtB subunit has type I deoxyribonuclease-like activity. In another embodiment, the B subunit has endonuclease activity that results in double strand breaks and blunt ends. In one embodiment, the Cdt holotoxin has structural homology with DNAse I.

In another embodiment, cdtA is encoded by the following nucleic acid sequence: ATGGCTCCGAGGAGAGGTACAATGAAAAAGTTTTTACCTGGTCTTTTATTGATGGGTT TAGTGGCTTGTTCGTCAAATCAACGAATGAGTGACTATTCTCAGCCTGAATCTCAATCT GATTTAGCACCTAAATCTTCAACAACACAATTCCAACCCCAACCCCTATTATCAAAAG CATCTTCAATGCCATTGAATTTGCTCTCTTCATCCAAGAATGGACAGGTATCGCCGTCT GAACCATCAAACTTTATGACTTTGATGGGACAAAATGGGGCACTGTTGACTGTCTGGG CGCTAGCAAAACGCAATTGGTTATGGGCTTATCCCAATATATATTCGCAGGACTTTGGAAATATTCGTAATTGGAAGATAGAACCTGGTAAACACCGTGAATATTTTCGTTTTGTT AATCAATCTTTAGGTACATGTATTGAAGCTTACGGTAATGGTTTAATTCATGATACTTG TAGTCTGGACAAATTAGCACAAGAGTTTGAGTTATTACCTACTGATAGTGGTGCGGTT GTCATTAAAAGTGTGTCACAAGGACGTTGTGTCACTTATAATCCTGTAAGTCCAACAT ATTATTCAACAGTTACATTATCAACTTGTGATGGCGCAACAGAACCATTACGTGATCA AACATGGTATCTCGCTCCTCCTGTATTAGAAGCAACAGCGGTTAATCACCACCACCAC CACCACGGATCCGGGCTGCTAACAAAGCCCCGAAAGGAAGC (SEQ ID NO: 8). In another embodiment, the CdtA subunit is a homologue of SEQ ID NO: 8. In another embodiment, the CdtA subunit is a variant of SEQ ID NO: 8. In another embodiment, the CdtA subunit is an isoform of SEQ ID NO: 8. In another embodiment, the CdtA subunit is a fragment of SEQ ID NO: 8. Each possibility represents a separate embodiment of the present invention.

In another embodiment, CdtA is encoded by the following amino acid sequence: MKKFLPGLLLMGLVACSSNQRMSDYSQPESQSDLAPKSSTTQFQPQPLLSKASSMPLNLLS SSKNGQVSPSEPSNFMTLMGQNGALLTVWALAKRNWLWAYPNIYSQDFGNIRNWKIEPG KHREYFRFVNQSLGTCIEAYGNGLIHDTCSLDKLAQEFELLPTDSGAVVIKSVSQGRCVTY NPVSPTYYSTVTLSTCDGATEPLRDQTWYLAPPVLEATAVNHHHHHHGSGLLTKPRKE (SEQ ID NO: 9). In another embodiment, the CdtA subunit is a homologue of SEQ ID NO: 9. In another embodiment, the CdtA subunit is a variant of SEQ ID NO: 9. In another embodiment, the CdtA subunit is an isoform of SEQ ID NO: 9. In another embodiment, the CdtA subunit is a fragment of SEQ ID NO: 9. Each possibility represents a separate embodiment of the present invention.

In one embodiment, the amino acid sequence of a CdtA subunit of the present invention is: LLSSSKNGQVSPSEPSNFMTLMGQNGALLTVWALAKRNWLWAYPNIYSQDFGNIRNWKI EPGKHREYFRFVNQSLGTCIEAYGNGLIHDTCSLDKLAQEFELLPTDSGAVVIKSVSQGRC VTYNPVSPTYYSTVTLSTCDGATEPLRDQTWYLAPPVLEATAV (SEQ ID NO: 10). In another embodiment, the CdtA subunit is a homologue of SEQ ID NO: 10. In another embodiment, the CdtA subunit is a variant of SEQ ID NO: 10. In another embodiment, the CdtA subunit is an isoform of SEQ ID NO: 10. In another embodiment, the CdtA subunit is a fragment of SEQ ID NO: 10. Each possibility represents a separate embodiment of the present invention.

In another embodiment, the CdtA subunit has an amino acid sequence set forth in one of the following GenBank entries: AAF81760; AAF19157; AAD10621; AAB06707; AAA18785; NP_860977; AAP78043; YP_002343541; CAL34252; Q46668; AAT92047; AAC70897; AAZ16246; ABV51672.1; YP_001272540.1; BAF63360.1; YP_999805.1; ZP_02270538.1; AAB06707.1; EAQ71960.1; ABJ00842.1; YP_178099.1; AAW34670.1; NP_873397.1; or AAP95786.1. In another embodiment, the CdtA subunit has any CdtA subunit amino acid sequence known in the art. In another embodiment, the CdtA subunit is a homologue of a sequence from one of the above GenBank entries. In another embodiment, the CdtA subunit is a variant of a sequence from one of the above GenBank entries. In another embodiment, the CdtA subunit is an isoform of a sequence from one of the above GenBank entries. In another embodiment, the CdtA subunit is a fragment of a sequence from one of the above GenBank entries. Each possibility represents a separate embodiment of the present invention.

In one embodiment, the nucleotide sequence of a CdtA subunit of the present invention is: ttgctctatcatccaagaatggacaggtatcgccgtctgaaccatcaaactttatgactttgatgggacaaaatggggcactgttgactgtctggg cgctagcaaaacgcaattggttatgggcttatcccaatatatattcgcaggactttggaaatattcgtaattggaagatagaacctggtaaacaccg tgaatattttcgttttgttaatcaatctttaggtacatgtattgaagcttacggtaatggtttaattcatgatacttgtagtctggacaaattagcacaaga gtttgagttattacctactgatagtggtgcggttgtcattaaaagtgtgtcacaaggacgttgtgtcacttataatcctgtaagtccaacatattattcaa cagttacattatcaacttgtgatggcgcaacagaaccattacgtgatcaaacatggtatctcgctcctcctgtattagaagcaacagcggtt (SEQ ID NO: 11). In another embodiment, the nucleotide sequence of the CdtA subunit is a homologue of SEQ ID NO: 11. In another embodiment, the nucleotide sequence of the CdtA subunit is a variant of SEQ ID NO: 11. In another embodiment, the nucleotide sequence of the CdtA subunit is an isoform of SEQ ID NO: 11. In another embodiment, the nucleotide sequence of the CdtA subunit is a fragment of SEQ ID NO: 11. Each possibility represents a separate embodiment of the present invention.

In another embodiment, the CdtA subunit has a nucleic acid sequence set forth in one of the following GenBank entries: AL111168.1; AE017125.1; CP000814.1; AB285204.1; NZ_AASL01000001.1; U51121.1; CP000538.1; CP000468.1; CP000025.1; or AE017143.1. In another embodiment, the CdtA subunit has any CdtA subunit nucleic acid sequence known in the art. In another embodiment, the CdtA subunit is a homologue of a sequence from one of the above GenBank entries. In another embodiment, the CdtA subunit is a variant of a sequence from one of the above GenBank entries. In another embodiment, the CdtA subunit is an isoform of a sequence from one of the above GenBank entries. In another embodiment, the CdtA subunit is a fragment of a sequence from one of the above GenBank entries. Each possibility represents a separate embodiment of the present invention.

In one embodiment, CdtA binds to a specific cell receptor, while in another embodiment, CdtA stabilizes the holotoxin. In one embodiment, analysis of the crystal structure of the toxin suggest that CdtA contains ricin-like domains, leading investigators to propose that it associates with carbohydrate.

In a particular embodiment, the invention provides a recombinant CdtA polypeptide comprising at least one of the mutations C149A and C178A. In another embodiment, the invention provides a recombinant CdtA polypeptide comprising the mutations C149A and C178A. In yet another embodiment, the invention provides a nucleic acid sequence encoding (i) a CdtA polypeptide comprising at least one of the mutations C149A and C178A or (ii) a nucleic acid sequence that is at least 85% identical to the sequence of (i).

In another embodiment, the invention provides at least one of the mutations C149A and C178A in SEQ ID NO: 9. In another embodiment, the invention provides the mutations C149A and C178A in SEQ ID NO: 9. In yet another embodiment, the invention provides a nucleic acid sequence encoding (i) a CdtA polypeptide comprising at least one of the mutations C149A and C178A (e.g., mutations in SEQ ID NO: 9) or (ii) a nucleic acid sequence that is at least 85% identical to the sequence of (i).

In another embodiment, the invention provides a composition comprising: a recombinant CdtA polypeptide comprising at least one of the mutations C149A and C178A, said polypeptide operably linked to a ligand that binds specifically to an antigen expressed on the surface of a cancerous epithelial cell type.

In another embodiment, the invention provides a recombinant CdtA polypeptide operably linked to a ligand that binds specifically to an antigen expressed on the surface of a cancerous epithelial cell type, wherein said recombinant CdtA polypeptide comprises at least one of the mutations C149A and C178A.

In another embodiment, the invention provides a chimeric CdtA polypeptide comprising at least one of the mutations C149A and C178A.

In another embodiment, the invention provides an isolated nucleic acid sequence encoding (i) a CdtA polypeptide comprising at least one of the mutations C149A and C178A or (ii) a nucleic acid sequence that is at least 85% identical to the sequence of (i).

In one embodiment, the amino acid sequence of a CdtB subunit of the present invention is: NLSDFKVATWNLQGSSAVNESKWNINVRQLLSGEQGADILMVQEAGSLPSSAVRTSRVIQ HGGTPIEEYTWNLGTRSRPNMVYIYYSRLDVGANRVNLAIVSRRQADEAFIVHSDSSVLQS RPAVGIRIGTDVFFTVHALATGGSDAVSLIRNIFTTFTSSPSSPERRGYSWMVVGDFNRAPV NLEAALRQEPAVSENTMAPTEPTHRSG-NILDYAILHDAHLPRREQARERIGASLMLNQLRS QITSDHFPVSFVRDR (SEQ ID NO: 12). In another embodiment, the CdtB subunit is a homologue of SEQ ID NO: 12. In another embodiment, the CdtB subunit is a variant of SEQ ID NO: 12. In another embodiment, the CdtB subunit is an isoform of SEQ ID NO: 12. In another embodiment, the CdtB subunit is a fragment of SEQ ID NO: 12. Each possibility represents a separate embodiment of the present invention.

In another embodiment, the CdtB subunit has an amino acid sequence set forth in one of the following GenBank entries: ZP_01072217; NP_860978; YP_002343540; YP_002308521; ZP_03223221; NP_873398; YP_001481648; YP_852557; YP_999804; YP_434821; YP_178098; YP_001272541; ZP_01100899; ZP_01067880; ZP_00370497; or ZP_00369375. In another embodiment, the CdtB subunit has any CdtB subunit amino acid sequence known in the art. In another embodiment, the CdtB subunit is a homologue of a sequence from one of the above GenBank entries. In another embodiment, the CdtB subunit is a variant of a sequence from one of the above GenBank entries. In another embodiment, the CdtB subunit is an isoform of a sequence from one of the above GenBank entries. In another embodiment, the CdtB subunit is a fragment of a sequence from one of the above GenBank entries. Each possibility represents a separate embodiment of the present invention.

In one embodiment, the nucleotide sequence of a CdtB subunit of the present invention is: aacttgagtgatttcaaagtagcaacttggaatctgcaaggttcttcagctgtaaatgaaagtaaatgaa-atattaatgtgcgccaattattatcggg agaacaaggtgcagatattttgatggta-caagaagcgggttcattaccaagttcggcagtaagaacctcacgagtaattcaac-atgggggaacg ccaattgaggaatatacctggaatttag-gtactcgctcccgtccaaatatggtctatatttattattcccgtttagatgttgg-ggcaaaccgagtgaac ttagctatcgtgtcacgtcgtcaagc-cgatgaagctttatcgtacattctgattcttctgtgcttcaatctcgcccggc-agtaggtatccgcattggta ctgatgtattattacagtgcatgctttg-gccacaggtggttctgatgcggtaagtttaattcgtaatatcttcactactt-nacctcatcaccatcatcac cggaaagacgaggatatagctggatggt-tgttggtgatttcaatcgtgcgccggttaatctggaagctgcattaagaca-ggaacccgccgtgagt gaaaatacaattattattgcgccaaca-gaaccgactcatcggtccggtaatattttagattatgcgattttacatgacgc-acatttaccacgtcgaga gcaagcacgtgaacgtatcggcg-caagtttaatgttaaatcagttacgctcacaaattacatccgatcattttc-ctgttagttttgttcgtgatc (SEQ ID NO: 13). In another embodiment, the nucleotide sequence of the CdtB subunit is a homologue of SEQ ID NO: 13. In another embodiment, the nucleotide sequence of the CdtB subunit is a variant of SEQ ID NO: 13. In another embodiment, the nucleotide sequence of the CdtB subunit is an isoform of SEQ ID NO: 13. In another embodiment, the nucleotide sequence of the CdtB subunit is a fragment of SEQ ID NO: 13. Each possibility represents a separate embodiment of the present invention.

In another embodiment, the CdtB subunit has a nucleic acid sequence set forth in one of the following GenBank entries: AL111168.1; AL627271.1; AE017125.1; CP000814.1; AB285204.1; EU794049.1; DQ092613.1; CP000468.1; CP000026.1; CP000155.1; CP000025.1; AE017143.1; CP000538.1; U51121.1; NZ_AASL01000001.1; or AE014613.1. In another embodiment, the CdtB subunit has any CdtB subunit nucleic acid sequence known in the art. In another embodiment, the CdtB subunit is a homologue of a sequence from one of the above GenBank entries. In another embodiment, the CdtB subunit is a variant of a sequence from one of the above GenBank entries. In another embodiment, the CdtB subunit is an isoform of a sequence from one of the above GenBank entries. In another embodiment, the CdtB subunit is a fragment of a sequence from one of the above GenBank entries. Each possibility represents a separate embodiment of the present invention.

In one embodiment, compositions and methods of the present invention comprise or use a Cdt fragment. In one embodiment, the Cdt fragment is a CdtB fragment or a homologue thereof.

In another embodiment, the amino acid sequence encoding the CdtB fragment is: MQWVKQLNVVFCTMLFSFSSY-ANLSDFKVATWNLQGSSAVNESKWNIN-VRQLLSGEQG ADILMVQEAGSLPSSAVRTSRVIQHG-GTPIEEYTWNLGTRSRPNMVYIYYSRLDVGANRV NLAIVSRRQADEAFIVHSDSSVLQSR-PAVGIRIGTDVFFTVHALATGGSDAVSLIRNIFTTFTS SPSSPERRGYSWMVVGDFNRAPVN-LEAALRQEPAVSENTIIIAPTEPTHQSGNILDYAILHD AHLPRREQVRERIGASLMLNQLRSQITSDHFP (SEQ ID NO: 14). In another embodiment, the CdtB fragment is a homologue of SEQ ID NO: 14. In another embodiment, the CdtB fragment is a variant of SEQ ID NO: 14. In another embodiment, the CdtB fragment is an isoform of SEQ ID NO: 14. In another embodiment, the CdtB fragment is a fragment of SEQ ID NO: 14. Each possibility represents a separate embodiment of the present invention.

In another embodiment, the nucleic acid sequence encoding the CdtB fragment is: ATGCAATGGGTAAAGCAAT-TAAATGTGGTTTTCTGTACGATGTTATT-TAGCTTTTCAAG TTATGCTAACTTGAGTGATTTCAAAG-TAGCAACTTGGAATCTGCAAGGTTCTTCAGCTG TAAATGAAAGTAAATGGAATATTAATGT-GCGCCAATTATTATCGGGAGAACAAGGTG CAGATATTTTGATGGTACAA-GAAGCGGGTTCATTACCAAGTTCGGCAG-TAAGAACCTC ACGAGTAATTCAACATGGGG-GAACGCCAATTGAGGAATATACCTGGAATTTAGGT-ACT CGCTCCCGTCCAAATATGGTCTATATT-TATTATTCCCGTTTAGATGTTGGGGCAAACCG AGT-GAACTTAGCTATCGTGTCACGTCGT-CAAGCCGATGAAGCTTTTATCGTACATTCTG ATTCTTCTGTGCTTCAATCTCGCCCG-GCAGTAGGTATCCGCATTGGTACTGATGTATTT TTTACAGTGCATGCTTTGGCCACAGGTG-GTTCTGATGCGGTAAGTTTAATTCGTAAATAT CTTCACTACTTTTACCTCATCACCAT-CATCACCGGAAAGACGAGGATATAGCTGGATG GTTGTTGGTGATTTCAATCGTGCGCCG-GTTAATCTGGAAGCTGCATTAAGACAGGAAC CCGC-CGTGAGTGAAAATACAATTATTAT-TGCGCCAACAGAACCGACTCATCAGTCCGG TAATATTTTAGATTATGCGATTTTACAT-GACGCACATTTACCACGTCGAGAGCAAGTA CGT-GAACGTATCGGCGCAAGTTTAATGT-TAAATCAGTTACGCTCACAAATTACATCCG ATCATTTTCCT (SEQ ID NO: 15). In another embodiment, the CdtB fragment is encoded by a homologue of SEQ ID NO: 15. In another embodiment, the CdtB fragment is encoded by a variant of SEQ ID NO: 15. In another embodiment, the CdtB fragment is encoded by an isoform of SEQ ID NO: 15. In another embodiment, the CdtB fragment is encoded by a fragment of SEQ ID NO: 15. Each possibility represents a separate embodiment of the present invention.

In another embodiment, the amino acid sequence encoding the CdtB fragment is: MQWVKQLNVVFCTMLFSFSSY-ANLSDFKVATWNLQGSSAVNESKWNIN-VRQLLSGEQG ADILMVQEAGSLPSSAVRTSRVIQHG-GTPIEEYTWNLGTRSRPNMVYIYYSRLDVGANRV NLAIVSRRQADEAFIVHSDSSVLQSR-PAVGIRIGTDVFFTVHALATGGSDAVSLIRNIFTTFTS SPSSPERRGYSWMVVGDFNRAPVN-LEAALRQEPAVSENTIIIAPTEPTHQSGNILDYAILHD AHLPRREQVRERIGASLMLNQLRSQITS-DHFPVSFVHDRHHHHHHGSGC (SEQ ID NO: 16). In another embodiment, the CdtB fragment is a homologue of SEQ ID NO: 16. In another embodiment, the CdtB fragment is a variant of SEQ ID NO: 16. In another embodiment, the CdtB fragment is an isoform of SEQ ID NO: 16. In another embodiment, the CdtB fragment is a fragment of SEQ ID NO: 16. Each possibility represents a separate embodiment of the present invention.

In another embodiment, a CdtB toxin, or its fragment or homologue comprises a mutated form of a CdtB toxin. In another embodiment, a CdtB toxin, or its fragment or homologue comprises a mutated form of a CdtB toxin fragment. In another embodiment, a mutated CdtB toxin or a mutated CdtB toxin fragment comprises a deletion mutation. In another embodiment, a mutated CdtB toxin or a mutated CdtB toxin fragment comprises an insertion mutation. In another embodiment, a mutated CdtB toxin or a mutated CdtB toxin fragment comprises a substitution mutation.

In one embodiment, a CdtB fragment of the present invention comprises a mutation. In one embodiment, the mutation comprises a mutation. In one embodiment, the mutation adds a DNA contact residue. In one embodiment, the mutation is G55R, S99Y, V134R, or a combination thereof. In another embodiment, the mutation adds a metal ion binding residue. In one embodiment, the mutation is L62E. In another embodiment, the mutation adds a residue that hydrogen bonds to a catalytic histidine, which in one embodiment, is H160. In one embodiment, the mutation is R100E. In another embodiment, the mutation is Y174P. In one embodiment, the mutation is a combination of two or more of the mutations described hereinabove.

In another embodiment, cdtC is encoded by the following nucleic acid sequence: ATGGTCGCTAAGGAGAATAC-TATGAAAAAATATTTATTGAGCTTCT-TATTAAGCATGA TATTGACTTTGACGAGTCATGCA-GAATCAAATCCTGATCCGACTACTTATCCTGATGTA GAGTTATCGCCTCCTCCACGTATTAGCT-TGCGTAGTTTGCTTACGGCTCAACCAATTAA AAAT-GACCATTATGATTCACATAATTATT-TAAGTACACATTGGGAATTAATTGATTAC AAGGGAAAAGAATATGAAAAATTACGT-GACGGTGGTACGTTGGTTCAATTTAAAGTG GTCG-GTGCAGCAAAATGTTTTGCTTTCCCAG-GCGAAGGCACAACTGATTGTAAAGATA TTGATCATACTGTGTTTAACCTTATTC-CAACTAATACAGGTGCGTTTTTAATCAAAGAT GCCCTATTAGGATTTTGTATGACAAGC-CATGACTTTGATGATTTGAGGCTTGAACCTTG TGGAATTTCAGTGAGTGGTCGAAC-CTTTTCGTTGGCGTATCAATGGGGAATATTACCTC CTTTTGGGCCAAGTAAAATTTTAAGAC-CACCGGTGGGGAGAAATCAGGGTAGCCACC ACCACCACCACCACGGATCCGGCTGCTAA (SEQ ID NO: 17). In another embodiment, the nucleic acid encoding the CdtC subunit is a homologue of SEQ ID NO: 17. In another embodiment, the nucleic acid encoding the CdtC subunit is a variant of SEQ ID NO: 17. In another embodiment, the nucleic acid encoding the CdtC subunit is an isoform of SEQ ID NO: 17. In another embodiment, the nucleic acid encoding the CdtC subunit is a fragment of SEQ ID NO: 17. Each possibility represents a separate embodiment of the present invention.

In another embodiment, CdtC is encoded by the following amino acid sequence: MVAKENTMKKYLLS-FLLSMILTLTSHAESNPDPTTYPDVELSPPPRISL-RSLLTAQPIKNDH YDSHNYLSTHWELIDYKGKEYEK-LRDGGTLVQFKVVGAAKCFAFPGEGTTD-CKDIDHTVF NLIPTNTGAFLIKDALLGFCMTSHDFD-DLRLEPCGISVSGRTFSLAYQWGILPPFGPSKILRPP VGRNQGSHHHHHHGSGC (SEQ ID NO: 18). In another embodiment, the CdtC subunit is a homologue of SEQ ID NO: 18. In another embodiment, the CdtC subunit is a variant of SEQ ID NO: 18. In another embodiment, the CdtC subunit is an isoform of SEQ ID NO: 18. In another embodiment, the CdtC subunit is a fragment of SEQ ID NO: 18. Each possibility represents a separate embodiment of the present invention.

In another embodiment, CdtC is encoded by the following amino acid sequence: MKKYLLSFLLSMILTLTSHAESN-PDPTTYPDVELSPPPRISLRSLLTAQPIKNDHYD-SHNYLS THWELIDYKGKEYEKLRDGGTLVQFKV-VGAAKCFAFPGEGTTDCKDIDHTVFNLIPTNTG AFLIKDALLGFCMTSHDFDDLRLEPCGISVSGRT-FSLAYQWGILPPFGPSKILRPPVGRNQGS HHHHH- HGSGC (SEQ ID NO: 19). In another embodiment, the CdtC subunit is a homologue of SEQ ID NO: 19. In another embodiment, the CdtC subunit is a variant of SEQ ID NO: 19. In another embodiment, the CdtC subunit is an isoform of SEQ ID NO: 19. In another embodiment, the CdtC subunit is a fragment of SEQ ID NO: 19. Each possibility represents a separate embodiment of the present invention.

In one embodiment, the amino acid sequence of a CdtC subunit of the present invention is: ESNPDPTTYPDVELSP-PPRISLRSLLTAQPIKNDHYDSHNYLSTHWELID-YKGKEYEKLRDG GTLVQFKVVGAAKCFAF-PGEGTTDCKDIDHTVFNLIPTNTGAFLIKDALLGFCM-TSHDFDD LRLEPCGISVSGRTFSLAYQWGILPPF-GPSKILRPPVGRNQGS (SEQ ID NO: 20). In another embodiment, the CdtC subunit is a homologue of SEQ ID NO: 20. In another embodiment, the CdtC subunit is a variant of SEQ ID NO: 20. In another embodiment, the CdtC subunit is an isoform of SEQ ID NO: 20. In another embodiment, the CdtC subunit is a fragment of SEQ ID NO: 20. Each possibility represents a separate embodiment of the present invention.

In another embodiment, the CdtC subunit has an amino acid sequence set forth in one of the following GenBank entries: YP_002343539.1; NP_860979.1; YP_001481647.1; YP_001272542.1; YP_852558.1; YP_999803.1; YP_178097.1; NP_873399.1; CAL34250.1; AAP78045.1; ABV51670.1; BAF63362.1; ABJ00844.1; EAQ72030.1; AAB06709.1; ZP_02270536.1; or AAW34668.1. In another embodiment, the CdtC subunit has any CdtC subunit amino acid sequence known in the art. In another embodiment, the CdtC subunit is a homologue of a sequence from one of the above GenBank entries. In another embodiment, the CdtC subunit is a variant of a sequence from one of the above GenBank entries. In another embodiment, the CdtC subunit is an isoform of a sequence from one of the above GenBank entries. In another embodiment, the CdtC subunit is a fragment of a sequence from one of the above GenBank entries. Each possibility represents a separate embodiment of the present invention.

In one embodiment, the nucleotide sequence of a CdtC subunit of the present invention is: gaatcaaatcctgatccgactact-tatcctgatgtagagttatcgcctcctccacgtattagcttgcgtagtttgctt-acggctcaaccaattaaaaat gaccattatgattcacataattatt-taagtacacattgggaattaattgattacaagggaaaagaatatgaaaattac-gtgacggtggtacgttggtt caatttaaagtggtcggtgcagcaaaat-gttttgctttcccaggcgaaggcacaactgattgtaaagatattgatcatactgt-gtttaaccttattcca actaatacaggtgcgttttttaatcaaagatgccctattag-gattttgtatgacaagccatgactttgatgatttgaggcttgaaccttgtggaatt-tcagt gagtggtcgaacctttcgttggcgtatcaatggggaatatta-cctcctttgggccaagtaaaattttaagaccaccggtggggagaaatcagggt agc (SEQ ID NO: 21). In another embodiment, the nucleotide sequence of the CdtC subunit is a homologue of SEQ ID NO: 21. In another embodiment, the nucleotide sequence of the CdtC subunit is a variant of SEQ ID NO: 21. In another embodiment, the nucleotide sequence of the CdtC subunit is an isoform of SEQ ID NO: 21. In another embodiment, the nucleotide sequence of the CdtC subunit is a fragment of SEQ ID NO: 21. Each possibility represents a separate embodiment of the present invention.

In another embodiment, the CdtC subunit has a nucleic acid sequence set forth in one of the following GenBank entries: AL111168.1; AE017125.1; CP000814.1; AB285204.1; CP000468.1; CP000538.1; U51121.1; NZ_AASL01000001.1; or CP000025.1. In another embodiment, the CdtC subunit has any CdtC subunit nucleic acid sequence known in the art. In another embodiment, the CdtC subunit is a homologue of a sequence from one of the above GenBank entries. In another embodiment, the CdtC subunit is a variant of a sequence from one of the above GenBank entries. In another embodiment, the CdtC subunit is an isoform of a sequence from one of the above GenBank entries. In another embodiment, the CdtC subunit is a fragment of a sequence from one of the above GenBank entries. Each possibility represents a separate embodiment of the present invention.

In one embodiment, CdtC comprises a cholesterol recognition site and, in one embodiment, CdtC binds to both cell and model membranes in a cholesterol dependent manner.

In another embodiment, the chimera provided herein is a CdtB-DNase I chimera. In another embodiment, the chimera provided herein is a multimeric chimera protein comprising DNase I or its fragment or homologue; and a CdtB toxin, or its fragment or homologue. In another embodiment, the chimera provided herein comprises DNase I or its fragment or homologue; and a CdtB toxin. In another embodiment, the chimera provided herein is a multimeric chimera protein comprising DNase I and a CdtB toxin, or its fragment or homologue. In another embodiment, the chimera provided herein consists of DNase I or its fragment or homologue; and a CdtB toxin.

In one embodiment, a chimera of the present invention comprises (a) said CdtB fragment in the amino terminus of said chimera and said DNase I fragment in the carboxy terminus of said chimera or (b) a homologue of a DNase I fragment in the carboxy terminus of said chimera and a Cdt fragment in the amino terminus of said chimera or (c) a DNase I in the carboxy terminus of said chimera and a homologue of a Cdt fragment in the amino terminus of said chimera or (d) a homologue of a DNase I fragment in the carboxy terminus of said chimera and a homologue of a Cdt fragment in the amino terminus of said chimera.

In another embodiment, the DNase I is a clone of the DNase I gene from *Homo sapiens* chromosome 16 (GenBank accession number AC005203). In another embodiment, the cdtB gene is from the human periodontal bacterium *Actinobacillus actinomycetemcomitans* Y4 (GenBank accession number AF006830), which in another embodiment is called *Aggregatibacter actinomycetemcomitans*. In another embodiment, a unique SphI restriction endonuclease cleavage site at about the midpoint of each sequence is used to construct two chimeric genes each containing opposite halves of the cdtB and DNase I genes.

In another embodiment, the nucleic acid sequence encoding the chimera is: TGCTAAATTCCCCTCTA-GAATAATTTTGTTTAACTTTAAGAAG-GAGATATACCATGGTG AGGGGAATGAAGCTGCTGGGGGCGCT-GCTGGCACTGGCGGCCCTACTGCAGGGGGCC GTGTCCCTGAAGATCGCAGCCTTCAA-CATCCAGACATTTGGGGAGACCAAGATGTCCA ATGCCACCCTCGTCAGCTACATTGTGCA-GATCCTGAGCCGCTATGACATCGCCCTGGT CCAG-GAGGTCAGAGACAGCCACCTGACTGC-CGTGGGGAAGCTGCTGGACAACCTCAA TCAGGATGCACCAGACACCTATCAC-TACGTGGTCAGTGAGCCACTGGGACGGAACAG CTATAAGGAGCGCTACCTGTTCGTGTA-CAGGCCTGACCAGGTGTCTGCGGTGGACAGC TAC-TACTACGATGATGGCTGCGAGCCCT-GCGGGAACGACACCTTCAACCGAGAGCCA GCCATTGTCAGGTTCTTCTCCCGGTTCA-CAGAGGTCAGGGAGTTTGCCATTGTTCCCCT GCAT-GCTTTGGCCACAGGTGGTTCTGATGCGG-TAAGTTTAATTCGTAATATCTTCACTA CTTTTACCTCGTCACCATCATCACCG- GAAAGACGAGGATATAGCTGGATGGTTGTTGGTGATTTCAATCGTGCGCCGGTTAATCTGGAAGCTGCATTAAGACAGGAACCCGCCGTG AGTGAAAATACAATTATTATTGCGCCAACAGAACCGACTCATCAGTCCGGTAATATTTTAGATTATGCGATTTTACATGACGCACATTTACCACGTCGAGAGCAAGTACGTGAACGTATCGGCGCAAGTTTAATGTTAAATCAGTTACGCTCACAAATTACATCCGATCATTTTCCTGTTAGTTTTGTTCATGATCGCCACCACCACCACCACCACGGATCCGGCTGCTAA (SEQ ID NO: 22). In one embodiment, the coding sequence of the nucleic acid sequence is underlined. In another embodiment, the nucleic acid encoding the chimera is a homologue of SEQ ID NO: 22. In another embodiment, the nucleic acid encoding the chimera is a variant of SEQ ID NO: 22. In another embodiment, the nucleic acid encoding the chimera is an isoform of SEQ ID NO: 22. In another embodiment, the nucleic acid encoding the chimera is a fragment of SEQ ID NO: 22. Each possibility represents a separate embodiment of the present invention.

In another embodiment, the nucleic acid sequence encoding the chimera is: ATGCAATGGGTAAAGCAATTAAATGTGGTTTTCTGTACGATGTTATTTAGCTTTTCAAGTTATGCTAACTTGAGTGATTTCAAAGTAGCAACTTGGAATCTGCAAGGTTCTTCAGCTGTAAATGAAAGTAAATGGAATATTAATGTGCGCCAATTATTATCGGGAGAACAAGGTGCAGATATTTTGATGGTACAAGAAGCGGGTTCATTACCAAGTTCGGCAGTAAGAACCTC ACGAGTAATTCAACATGGGGAACGCCAATTGAGGAATATACCTGGAATTTAGGTACT CGCTCCCGTCCAAATATGGTCTATATTTATTATTCCCGTTTAGATGTTGGGGCAAACCG AGTGAACTTAGCTATCGTGTCACGTCGTCAAGCCGATGAAGCTTTTATCGTACATTCTGATTCTTCTGTGCTTCAATCTCGCCCGGCAGTAGGTATCCGCATTGGTACTGATGTATTTTTTACAGTGCATGCGGCCCCGGGGGACGCAGTAGCCGAGATCGACGCTCTCTATGACG TCTACCTGGATGTCCAAGAGAAATGGGGCTTGGAGGACGTCATGTTGATGGGCGACTTCAATGCGGGCTGCAGCTATGTGAGACCCTCCCAGTGGTCATCCATCCGCCTGTGGACA AGCCCCACCTTCCAGTGGCTGATCCCCGACAGCGCTGACACCACAGCTACACCCACGCACTGTGCCTATGACAGGATCGTGGTTGCAGGGATGCTGCTCCGAGGCGCCGTTGTTCCCGACTCGGCTCTTCCCTTTAACTTCCAGGCTGCCAATGGCCTGAGTGACCAACTGGCCCAAGCCATCAGTGACCACTATCCAGTGGAGGTGATGCTGAAGGGATCCCGGGAGCTC GTGGATCCGAATTCTGTACAGGCGCGCCTGCAGGACGTCGACGGTACCATCGATACGCGTTCGAAGCTTGCGGCCGCACAGCTGTATACACGTGCAAGCCAGCCAGAACTCGCTCCTGAAGACCCAGAGGATCTCGAGCACCACCACCACCACCACCATATGCTCGAGGATCC GGCTGCTAACAAAGCCCGAAAAGAAGG (SEQ ID NO: 23). In another embodiment, the nucleic acid encoding the chimera is a homologue of SEQ ID NO: 23. In another embodiment, the nucleic acid encoding the chimera is a variant of SEQ ID NO: 23. In another embodiment, the nucleic acid encoding the chimera is an isoform of SEQ ID NO: 23. In another embodiment, the nucleic acid encoding the chimera is a fragment of SEQ ID NO: 23. Each possibility represents a separate embodiment of the present invention.

In another embodiment, the amino acid sequence encoding the chimera is: MVRGMKLLGALLALAALLQGAVSLKIAAFNIQTFGETKMSNATLVSYIVQILSRYDIALVQEVRDSHLTAVGKLLDNLNQDAPDTYHYVVSEPLGRNSYKERYLFVYRPDQVSAVDSYYY DDGCEPCGNDTFNREPAIVRFFSRFTEVREFAIVPLHALATGGSDAVSLIRNIFTTFTSSPSSPERRGYSWMVVGDFNRAPVNLEAALRQEPAVSENTIIAPTEPTHQSGNILDYAILHDAHLPRREQVRERIGASLMLNQLRSQITSDHFPVSFVHDRHHHHHHGSGC (SEQ ID NO: 24). In another embodiment, the chimera is a homologue of SEQ ID NO: 24. In another embodiment, the chimera is a variant of SEQ ID NO: 24. In another embodiment, the chimera is an isoform of SEQ ID NO: 24. In another embodiment, the chimera is a fragment of SEQ ID NO: 24. Each possibility represents a separate embodiment of the present invention.

In another embodiment, the amino acid sequence encoding the chimera is: MQWVKQLNVVFCTMLFSFSSYANLSDFKVATWNLQGSSAVNESKWNINVRQLLSGEQGADILMVQEAGSLPSSAVRTSRVIQHGGTPIEEYTWNLGTRSRPNMVYIYYSRLDVGANRVNLAIVSRRQADEAFIVHSDSSVLQSRPAVGIRIGTDVFFTVHAAPGDAVAEIDALYDVYLD VQEKWGLEDVMLMGDFNAGCSYVRPSQWSSIRLWTSPTFQWLIPDSADTTATPTHCAYD RIVVAGMLLRGAVVPDSALPFNFQAANGLSDQLAQAISDHYPVEVMLKGSRELVDPNSVQ ARLQDVDGTIDTRSKLAAAQLYTRASQPELAPEDPEDLEHHHHHHHMLEDPAANKARKE G (SEQ ID NO: 25). In another embodiment, the chimera is a homologue of SEQ ID NO: 25. In another embodiment, the chimera is a variant of SEQ ID NO: 25. In another embodiment, the chimera is an isoform of SEQ ID NO: 25. In another embodiment, the chimera is a fragment of SEQ ID NO: 25. Each possibility represents a separate embodiment of the present invention.

In another embodiment, the amino acid sequence encoding the chimera is: MQWVKQLNVVFCTMLFSFSSYANLSDFKVATWNLQGSSAVNESKWNINVRQLLSGEQGADILMVQEAGSLPSSAVRTSRVIQHGGTPIEEYTWNLGTRSRPNMVYIYYSRLDVGANRVNLAIVSRRQADEAFIVHSDSSVLQSRPAVGIRIGTDVFFTVHAAPGDAVAEIDALYDVYLD VQEKWGLEDVMLMGDFNAGCSYVRPSQWSSIRLWTSPTFQWLIPDSADTTATPTHCAYD RIVVAGMLLRGAVVPDSALPFNFQAANGLSDQLAQAISDHYPVEVMLKHHHHHHHMLED PAANKAQKK (SEQ ID NO: 26). In another embodiment, the chimera is a homologue of SEQ ID NO: 26. In another embodiment, the chimera is a variant of SEQ ID NO: 26. In another embodiment, the chimera is an isoform of SEQ ID NO: 26. In another embodiment, the chimera is a fragment of SEQ ID NO: 26. Each possibility represents a separate embodiment of the present invention.

In another embodiment, the amino acid sequence encoding the chimera is: MVRGMKLLGALLALAALLQGAVSLKIAAFNIQTFGETKMSNATLVSYIVQILSRYDIALVQEVRDSHLTAVGKLLDNLNQDAPDTYHYVVSEPLGRNSYKERYLFVYRPDQVSAVDSYYY DDGCEPCGNDTFNREPAIVRFFSRFTEVREFAIVPLHALATGGSDAVSLIRNIFTTFTSSPSSPERRGYSWMVVGDFNRAPVNLEAALRQEPAVSENTIIAPTEPTHQSGNILDYAILHDAHLPRREQVRERIGASLMLNQLRSQITSDHFPVSFVHDRHHHHHHGSGC (SEQ ID NO: 27). In another embodiment, the chimera is a homologue of SEQ ID NO: 27. In another embodiment, the chimera is a variant of SEQ ID NO: 27. In another embodiment, the chimera is an isoform of SEQ ID NO: 27. In another embodiment, the chimera is a fragment of SEQ ID NO: 27. Each possibility represents a separate embodiment of the present invention.

In one embodiment a chimera of the present invention binds to both CdtA and CdtC. In another embodiment, a chimera of the present invention binds to CdtC only.

In another embodiment, the chimera is encoded by the following nucleic acid sequence: ATGGAATGGGTAaag-CAATTAAATGTGGTTTTCTGTACGATGTTATTTAG-CTTTTCAA GTTATGCTAACTTGAGTGATTTCAAAG-TAGCAACTTGGAATCTGCAAGGTTCTTCA GCTG-TAAATGAAAGTAAATGGAATATTAATGT-GCGCCAATTATTATCGAGGGAAC AAGGTGCAGATATTGAGATGGTACAA-GAAGCGGGTTCATTACCAAGTTCGGCAGT AAGAACCTCACGAGTAATTCAA-CATGGGGGAACGCCAATTGAGGAATATACCTGG AATTTAGGTACTCGCTATGAGC-CAAATATGGTCTATATTTATTATTCCCGTTTAGAT GTTGGGGCAAACCGAGTGAACTTAGC-TATCGTGTCACGTCGTCAAGCCGATGAAG CTTT-TATCCGACATTCTGATTCTTCTGTGCT-TCAATCTCGCCCGGCAGTAGGTATCC GCATTGGTACTGATGTATTTTTTACAGT-GCATGCGGCCCCGGGGGACGCAGTAGCC GAGATC-GACGCTCTCCCTGACGTCTACCTGGAT-GTCCAAGAGAAATGGGGCTTGGA GGACGTCATGTTGATGGGCGACTTCAAT-GCGGGCTGCAGCTATGTGAGACCCTCCC AGTGGT-CATCCATCCGCCTGTGGACAAGCCCCAC-CTTCCAGTGGCTGATCCCCGAC AGCGCTGACACCACAGCTACACCCACG-CACTGTGCCTATGACAGGATCGTGGTTGC AGGGAT-GCTGCTCCGAGGCGCCGTTGTTC-CCGACTCGGCTCTTCCCTTTAACTTCCA GGCTGCCTTAATGTTAAATCAGT-TACGCTCACAAATTACAAGTGACCACTATCCAG TGGAGGTGATGCTGAAGCACCACCAC-CACCACCACCATATGCTCGAGGATCCGGC TGCTAA-CAAGCTGAAAGAAGC (SEQ ID NO: 28; CdtB/DNa-se$^{Y174}$). In another embodiment, the nucleic acid encoding the chimera is a homologue of SEQ ID NO: 28. In another embodiment, the nucleic acid encoding the chimera is a variant of SEQ ID NO: 28. In another embodiment, the nucleic acid encoding the chimera is an isoform of SEQ ID NO: 28. In another embodiment, the nucleic acid encoding the chimera is a fragment of SEQ ID NO: 28. Each possibility represents a separate embodiment of the present invention.

In another embodiment, the chimera is encoded by the following amino acid sequence: MEWVKQLNVVFCTM-LFSFSSYANLSDFKVATWNLQGSSAVNESKWNI-NVRQLLSREQGA DIEMVQEAGSLPSSAVRTS-RVIQHGGTPIEEYTWNLGTRYEPNMVY-IYYSRLDVGANRVN LAIVSRRQADEAFIRHSDSSV-LQSRPAVGIRIGTDVFFTVHAAPGDAVAEIDALPDVY-LDVQ EKWGLEDVMLMGDFNAGCSYVRPSQWS-SIRLWTSPTFQWLIPDSADTTATPTHCAYDRIV VAGM-LLRGAVVPDSALPFNFQAALMLNQLRS-QITSDHYPVEVMLKHHHHHHHMLEDPA ANKLKEA (SEQ ID NO: 29; CdtB/DNase$^{Y174}$). In another embodiment, the chimera is a homologue of SEQ ID NO: 29. In another embodiment, the chimera is a variant of SEQ ID NO: 29. In another embodiment, the chimera is an isoform of SEQ ID NO: 29. In another embodiment, the chimera is a fragment of SEQ ID NO: 29. Each possibility represents a separate embodiment of the present invention. Each possibility represents a separate embodiment of the present invention.

In another embodiment, the chimera is encoded by the following nucleic acid sequence: ATGGAATGGGTAaag-CAATTAAATGTGGTTTTCTGTACGATGTTATTTAG-CTTTTCAAGT TATGCTAACTTGAGTGATTTCAAAG-TAGCAACTTGGAATCTGCAAGGTTCTTCAGCTGT AAATGAAAGTAAATGGAATATTAATGT-GCGCCAATTATTATCGAGGGAACAAGGTGC AGATATTGAGATGGTACAAGAAGCGGGT-TCATTACCAAGTTCGGCAGTAAGAACCTC ACGAG-TAATTCAACATGGGGGAACGCCAAT-TGAGGAATATACCTGGAATTTAGGTACT CGCTATGAGCCAAATATGGTCTATATT-TATTATTCCCGTTTAGATGTTGGGGCAAACCG AGT-GAACTTAGCTATCGTGTCACGTCGT-CAAGCCGATGAAGCTTTTATCCGACATTCT GATTCTTCTGTGCTTCAATCTCGCCCG-GCAGTAGGTATCCGCATTGGTACTGATGTATT TTT-TACAGTGCATGCGGCCCCGGGGGACG-CAGTAGCCGAGATCGACGCTCTCTATGAC GTCTACCTGGATGTCCAA-GAGAAATGGGGCTTGGAGGACGTCATGT-TGATGGGCGACT TCAATGCGGGCTGCAGCTATGT-GAGACCCTCCCAGTGGTCATCCATCCGCCTGTGGAC AAGCCCCACCTTCCAGTGGCTGATC-CCCGACAGCGCTGACACCACAGCTACACCCACG CACTGTGCCTATGACAGGATCGTGGTTG-CAGGGATGCTGCTCCGAGGCGCCGTTGTTC CCGACTCGGCTCTTCCCTTTAACTTC-CAGGCTGCCAATGGCCTGAGTGACCAACTGGC CCAAGCCATCAGTGACCACTATCCAGTG-GAGGTGATGCTGAAGCACCACCACCACCA CCAC-CATATGCTCGAGGATCCGGCTGCTAA-CAAGCTGAAAGAAGC (SEQ ID NO: 30). In another embodiment, the nucleic acid encoding the chimera is a homologue of SEQ ID NO: 30. In another embodiment, the nucleic acid encoding the chimera is a variant of SEQ ID NO: 30. In another embodiment, the nucleic acid encoding the chimera is an isoform of SEQ ID NO: 30. In another embodiment, the nucleic acid encoding the chimera is a fragment of SEQ ID NO: 30. Each possibility represents a separate embodiment of the present invention.

In another embodiment, the chimera is encoded by the following amino acid sequence: MEWVKQLNVVFCTM-LFSFSSYANLSDFKVATWNLQGSSAVNESK-WNINVRQLLSREQGA DIEMVQEAGSLPSSAVR-TSRVIQHGGTPIEEYTWNLGTRYEPNM-VYIYYSRLDVGANRVN LAIVSRRQADEAFIRHSDSS-VLQSRPAVGIRIGTDVFFTVHAAPGDAVAEIDA-LYDVYLDVQ EKWGLEDVMLMGDFNAGC-SYVRPSQWSSIRLWTSPTFQWLIPDSADTTATPT-HCAYDRIV VAGMLLRGAVVPDSALPFNFQAANGLS-DQLAQAISDHYPVEVMLKHHHHHHHMLEDPA ANKLKEA (SEQ ID NO: 31). In another embodiment, the chimera is a homologue of SEQ ID NO: 31. In another embodiment, the chimera is a variant of SEQ ID NO: 31. In another embodiment, the chimera is an isoform of SEQ ID NO: 31. In another embodiment, the chimera is a fragment of SEQ ID NO: 31. Each possibility represents a separate embodiment of the present invention. Each possibility represents a separate embodiment of the present invention.

In another embodiment, the chimera is encoded by the following nucleic acid sequence: ATGGAATGGGTAAAG-CAATTAAATGTGGTTTTCTGTACGATGT-TATTTAGCTTTTCAAG TTATGCTAACTTGAGT-GATTTCAAAGTAGCAACTTGGAATCTGCAAGGTT-CTTCAGCTG TAAATGAAAGTAAATGGAATATTAAT-GTGCGCCAATTATTATCGGGAGAACAAGGTG CAGATATTTTGATGGTACAA-GAAGCGGGTTCATTACCAAGTTCGGCAG-TAAGAACCTC ACGAGTAATTCAACATGGGG-GAACGCCAATTGAGGAATATACCTGGAATTTAGGTA-CT CGCTATGAGCCAAATATGGTCTATATT-TATTATTCCCGTTTAGATGTTGGGGCAAACCG AGT-GAACTTAGCTATCGTGTCACGTCGT-CAAGCCGATGAAGCTTTTATCGTACATTCTG ATTCTTCTGTGCTTCAATCTCGCCCG-GCAGTAGGTATCCGCATTGGTACTGATGTATTT TTTACAGTGCATGCGGCCCCGGGGGACG-CAGTAGCCGAGATCGACGCTCTCTATGACG TCTAC-CTGGATGTCCAAGAGAAATGGGGCTTG-GAGGACGTCATGTTGATGGGCGACTT CAATGCGGCTGCAGCTATGTGAGAC-CCTCCCAGTGGTCATCCATCCGCCTGTGGACA AGC-CCCACCTTCCAGTGGCTGATCCCCGA-CAGCGCTGACACCACAGCTACACCCACGC ACTGTGCCTATGACAGGATCGTGGTTG-CAGGGATGCTGCTCCGAGGCGCCGTTGTTCC CGACTCGGCTCTTCCCTTTAACTTCCAG-GCTGCCAATGGCCTGAGTGACCAACTGGCC CAAGCCATCAGTGACCACTATCCAGTG-GAGGTGATGCTGAAGCACCACCACCACCAC CAC-CATATGCTCGAGGATCCGGCTGCTAA-CAAGCTGAAAGAAGC (SEQ ID NO: 32). In another embodiment, the nucleic acid encoding the chimera is a homologue of SEQ ID NO: 32. In another embodiment, the nucleic acid encoding the chimera is a variant of SEQ ID NO: 32. In another embodiment, the nucleic acid encoding the chimera is an isoform of SEQ ID NO: 32. In another embodiment, the nucleic acid encoding the chimera is a fragment of SEQ ID NO: 32. Each possibility represents a separate embodiment of the present invention.

In another embodiment, the chimera is encoded by the following amino acid sequence: MEWVKQLNVVFCTM-LFSFSSYANLSDFKVATWNLQGSSAVNESKWNI-NVRQLLSGEQGA DILMVQEAGSLPSSAVR-TSRVIQHGGTPIEEYTWNLGTRYEPNM-VYIYYSRLDVGANRVNL AIVSRRQADEAFIVHSDSS-VLQSRPAVGIRIGTDVFFTVHAAPGDA-VAEIDALYDVYLDVQ EKWGLEDVMLMGDFNAGCSYVRPSQWS-SIRLWTSPTFQWLIPDSADTTATPTHCAYDRIV VAGM-LLRGAVVPDSALPFNFQAANGLS-DQLAQAISDHYPVEVMLKHHHHHHMLEDPA ANKLKEA (SEQ ID NO: 33). In another embodiment, the chimera is a homologue of SEQ ID NO: 33. In another embodiment, the chimera is a variant of SEQ ID NO: 33. In another embodiment, the chimera is an isoform of SEQ ID NO: 33. In another embodiment, the chimera is a fragment of SEQ ID NO: 33. Each possibility represents a separate embodiment of the present invention. Each possibility represents a separate embodiment of the present invention.

In another embodiment, the chimera is encoded by the following nucleic acid sequence: ATGGAATGGGTAaag-CAATTAAATGTGGTTTTCTGTACGATGT-TATTTAGCTTTTCAAGT TATGCTAACTTGAGT-GATTTCAAAGTAGCAACTTGGAATCTGCAAGGTT-CTTCAGCTGT AAATGAAAGTAAATGGAATATTAAT-GTGCGCCAATTATTATCGAGGGAACAAGGTGC AGATATTGAGATGGTACAAGAAGCGGGT-TCATTACCAAGTTCGGCAGTAAGAACCTC ACGAG-TAATTCAACATGGGGAACGCCAAT-TGAGGAATATACCTGGAATTTAGGTACT CGCTATGAGCCAAATATGGTCTATATT-TATTATTCCCGTTTAGATGTTGGGGCAAACCG AGT-GAACTTAGCTATCGTGTCACGTCGT-CAAGCCGATGAAGCTTTTATCGACATTCT GATTCTTCTGTGCTTCAATCTCGCCCG-GCAGTAGGTATCCGCATTGGTACTGATGTATT TTT-TACAGTGCATGCGGCCCCGGGGGACG-CAGTAGCCGAGATCGACGCTCTCTATGAC GTCTACCTGGATGTCCAA-GAGAAATGGGGCTTGGAGGACGTCATGT-TGATGGGCGACT TCAATGCGGGCTGCAGCTATGT-GAGACCCTCCCAGTGGTCATCCATCCGCCTGTGGAC AAGCCCCACCTTCCAGTGGCTGATC-CCCGACAGCGCTGACACCACAGCTACACCCACG CACTGTGCCTATGACAGGATCGTGGTTG-CAGGGATGCTGCTCCGAGGCGCCGTTGTTC CCGACTCGGCTCTTCCCTTTAACTTC-CAGGCTGCCTTAATGTTAAATCAGTTACGCTCA CAAATTACAAGTGACCACTATCCAGTG-GAGGTGATGCTGAAGCACCACCACCACCAC CAC-CATATGCTCGAGGATCCGGCTGCTAA-CAAGCTGAAAGAAGC (SEQ ID NO: 34). In another embodiment, the nucleic acid encoding the chimera is a homologue of SEQ ID NO: 34. In another embodiment, the nucleic acid encoding the chimera is a variant of SEQ ID NO: 34. In another embodiment, the nucleic acid encoding the chimera is an isoform of SEQ ID NO: 34. In another embodiment, the nucleic acid encoding the chimera is a fragment of SEQ ID NO: 34. Each possibility represents a separate embodiment of the present invention.

In another embodiment, the chimera is encoded by the following amino acid sequence: MEWVKQLNVVFCTM-LFSFSSYANLSDFKVATWNLQGSSAVNESKWNIN-VRQLLSREQGA DIEMVQEAGSLPSSAVRTSRVIQHG-GTPIEEYTWNLGTRYEPNMVYIYYSRLDVGANRVN LAIVSRRQADEAFIRHSDSSVLQSRPAV-GIRIGTDVFFTVHAAPGDAVAEIDALYDVYLDVQ EKWGLEDVMLMGDFNAGCSYVRPSQWS-SIRLWTSPTFQWLIPDSADTTATPTHCAYDRIV VAGM-LLRGAVVPDSALPFNFQAALMLNQLRS-QITSDHYPVEVMLKHHHHHHHMLEDPA ANKLKEA (SEQ ID NO: 35). In another embodiment, the chimera is a homologue of SEQ ID NO: 35. In another embodiment, the chimera is a variant of SEQ ID NO: 35. In another embodiment, the chimera is an isoform of SEQ ID NO: 35. In another embodiment, the chimera is a fragment of SEQ ID NO: 35. Each possibility represents a separate embodiment of the present invention. Each possibility represents a separate embodiment of the present invention.

In another embodiment, the chimera is encoded by the following nucleic acid sequence: ATGGAATGGGTAaag-CAATTAAATGTGGTTTTCTGTACGATGT-TATTTAGCTTTTCAAGT TATGCTAACTTGAGT-GATTTCAAAGTAGCAACTTGGAATCTGCAAGGTTC-TTCAGCTGT AAATGAAAGTAAATGGAATATTAATGT-GCGCCAATTATTATCGGGAGAACAAGGTGC AGATATTGAGATGGTACAAGAAGCGGGT-TCATTACCAAGTTCGGCAGTAAGAACCTC ACGAG-TAATTCAACATGGGGAACGCCAAT-TGAGGAATATACCTGGAATTTAGGTACT CGCTATGAGCCAAATATGGTCTATATT-TATTATTCCCGTTTAGATGTTGGGGCAAACCG AGT-GAACTTAGCTATCGTGTCACGTCGT-CAAGCCGATGAAGCTTTTATCGTACATTCTG ATTCTTCTGTGCTTCAATCTCGCCCG-GCAGTAGGTATCCGCATTGGTACTGATGTATTT TTTACAGTGCATGCGGCCCCGGGGGACG-CAGTAGCCGAGATCGACGCTCTCTATGACG TCTAC-CTGGATGTCCAAGAGAAATGGGGCTTG- GAGGACGTCATGTTGATGGGCGACTT
CAATGCGGGCTGCAGCTATGTGAGAC-
CCTCCCAGTGGTCATCCATCCGCCTGTGGACA AGC-
CCCACCTTCCAGTGGCTGATCCCCGA-
CAGCGCTGACACCACAGCTACACCCACGC
ACTGTGCCTATGACAGGATCGTGGTTG-
CAGGGATGCTGCTCCGAGGCGCCGTTGTTCC
CGACTCGGCTCTTCCCTTTAACTTCCAG-
GCTGCCAATGGCCTGAGTGACCAACTGGCC
CAAGCCATCAGTGACCACTATCCAGTG-
GAGGTGATGCTGAAGCACCACCACCACCAC CAC-
CATATGCTCGAGGATCCGGCTGCTAA-
CAAGCTGAAAGAAGC (SEQ ID NO: 36). In another
embodiment, the nucleic acid encoding the chimera is a
homologue of SEQ ID NO: 36. In another embodiment, the
nucleic acid encoding the chimera is a variant of SEQ ID NO:
36. In another embodiment, the nucleic acid encoding the
chimera is an isoform of SEQ ID NO: 36. In another embodiment, the nucleic acid encoding the chimera is a fragment of
SEQ ID NO: 36. Each possibility represents a separate
embodiment of the present invention.

In another embodiment, the chimera is encoded by the
following amino acid sequence: MEWVKQLNVVFCTM-
LFSFSSYANLSDFKVATWNLQGSSAVNESKWN-
INVRQLLSGEQGA DIEM-
VQEAGSLPSSAVRTSRVIQHGGT-
PIEEYTWNLGTRYEPNMVYIYYSRLDVGANRVN
LAIVSRRQADEAFIVHSDSSVLQSRPAV-
GIRIGTDVFFTVHAAPGDAVAEIDALYDVYLDV QEK-
WGLEDVMLMGDFNAGCSYVRPSQWS-
SIRLWTSPTFQWLIPDSADTTATPTHCAYDRI
VVAGMLLRGAVVPDSALPFNFQAANGLS-
DQLAQAISDHYPVEVMLKHHHHHHMLEDP
AANKLKEA (SEQ ID NO: 37). In another embodiment, the
chimera is a homologue of SEQ ID NO: 37. In another
embodiment, the chimera is a variant of SEQ ID NO: 37. In
another embodiment, the chimera is an isoform of SEQ ID
NO: 37. In another embodiment, the chimera is a fragment of
SEQ ID NO: 37. Each possibility represents a separate
embodiment of the present invention. Each possibility represents a separate embodiment of the present invention.

In another embodiment, the chimera is encoded by the
following nucleic acid sequence: ATGGAATGGGTAaag-
CAATTAAATGTGGTTTTCTGTACGATGT-
TATTTAGCTTTTCAAGT TATGCTAACTTGAGT-
GATTTCAAAGTAGCAACTTGGAATCTGCAAGGTTC-
TTCAGCTGT AAATGAAAGTAAATGGAATATTAATGT-
GCGCCAATTATTATCGAGGGAACAAGGTGC
AGATATTGAGATGGTACAAGAAGCGGGT-
TCATTACCAAGTTCGGCAGTAAGAACCTC ACGAG-
TAATTCAACATGGGGAACGCCAAT-
TGAGGAATATACCTGGAATTTAGGTACT
CGCTATGAGCCAAATATGGTCTATATT-
TATTATTCCCGTTTAGATGTTGGGGCAAACCG AGT-
GAACTTAGCTATCGTGTCACGTCGT-
CAAGCCGATGAAGCTTTTATCGTACATTCTG
ATTCTTCTGTGCTTCAATCTCGCCCG-
GCAGTAGGTATCCGCATTGGTACTGATGTATTT
TTTACAGTGCATGCGGCCCCGGGGGACG-
CAGTAGCCGAGATCGACGCTCTCTATGACG TCTAC-
CTGGATGTCCAAGAGAAATGGGGCTTG-
GAGGACGTCATGTTGATGGGCGACTT
CAATGCGGGCTGCAGCTATGTGAGAC-
CCTCCCAGTGGTCATCCATCCGCCTGTGGACA AGC-
CCCACCTTCCAGTGGCTGATCCCCGA-
CAGCGCTGACACCACAGCTACACCCACGC
ACTGTGCCTATGACAGGATCGTGGTTG-
CAGGGATGCTGCTCCGAGGCGCCGTTGTTCC
CGACTCGGCTCTTCCCTTTAACTTCCAG-
GCTGCCAATGGCCTGAGTGACCAACTGGCC
CAAGCCATCAGTGACCACTATCCAGTG-
GAGGTGATGCTGAAGCACCACCACCACCAC CAC-
CATATGCTCGAGGATCCGGCTGCTAA-
CAAGCTGAAAGAAGC (SEQ ID NO: 38). In another
embodiment, the nucleic acid encoding the chimera is a
homologue of SEQ ID NO: 38. In another embodiment, the
nucleic acid encoding the chimera is a variant of SEQ ID NO:
38. In another embodiment, the nucleic acid encoding the
chimera is an isoform of SEQ ID NO: 38. In another embodiment, the nucleic acid encoding the chimera is a fragment of
SEQ ID NO: 38. Each possibility represents a separate
embodiment of the present invention.

In another embodiment, the chimera is encoded by the
following amino acid sequence: MEWVKQLNVVFCTM-
LFSFSSYANLSDFKVATWNLQGSSAVNESKWNI-
NVRQLLSREQGA DIEMVQEAGSLPSSAVR-
TSRVIQHGGTPIEEYTWNLGTRYEPNM-
VYIYYSRLDVGANRVN LAIVSRRQADEAFIVHSDSS-
VLQSRPAVGIRIGTDVFFTVHAAPGDA-
VAEIDALYDVYLDV
QEKWGLEDVMLMGDFNAGCSYVRPSQWS-
SIRLWTSPTFQWLIPDSADTTATPTHCAYDRI VVAGM-
LLRGAVVPDSALPFNFQAANGLS-
DQLAQAISDHYPVEVMLKHHHHHHMLEDP
AANKLKEA (SEQ ID NO: 39). In another embodiment, the
chimera is a homologue of SEQ ID NO: 39. In another
embodiment, the chimera is a variant of SEQ ID NO: 39. In
another embodiment, the chimera is an isoform of SEQ ID
NO: 39. In another embodiment, the chimera is a fragment of
SEQ ID NO: 39. Each possibility represents a separate
embodiment of the present invention. Each possibility represents a separate embodiment of the present invention.

In another embodiment, a deletion mutant comprises a
single deletion. In another embodiment, a deletion mutant
comprises a deletion of at least a single nucleotide. In another
embodiment, a deletion mutant comprises a deletion of at
least a single amino acid. In another embodiment, a deletion
mutant comprises a deletion of at least 2 amino acids. In
another embodiment, a deletion mutant comprises a deletion
of at least 3 amino acids. In another embodiment, a deletion
mutant comprises a deletion of at least 4 amino acids. In
another embodiment, a deletion mutant comprises a deletion
of at least 5 amino acids. In another embodiment, a deletion
mutant comprises a deletion of at least 6 amino acids. In
another embodiment, a deletion mutant comprises a deletion
of at least 8 amino acids. In another embodiment, a deletion
mutant comprises a deletion of at least 10 amino acids.

In another embodiment, an insertion mutant comprises a
single insertion. In another embodiment, an insertion mutant
comprises an insertion of at least a single nucleotide. In
another embodiment, an insertion mutant comprises an insertion of at least a single amino acid. In another embodiment, an
insertion mutant comprises an insertion of at least 2 amino
acids. In another embodiment, an insertion mutant comprises
an insertion of at least 3 amino acids. In another embodiment,
an insertion mutant comprises an insertion of at least 4 amino
acids. In another embodiment, an insertion mutant comprises
an insertion of at least 5 amino acids. In another embodiment,
an insertion mutant comprises an insertion of at least 6 amino
acids. In another embodiment, an insertion mutant comprises
an insertion of at least 8 amino acids. In another embodiment,
an insertion mutant comprises an insertion of at least 10
amino acids.

In another embodiment, a substitution mutant comprises a single substitution. In another embodiment, a substitution mutant comprises a substitution of at least a single amino acid. In another embodiment, a substitution mutant comprises a substitution of at least 2 amino acids. In another embodiment, a substitution mutant comprises a substitution of at least 3 amino acids. In another embodiment, a substitution mutant comprises a substitution of at least 4 amino acids. In another embodiment, a substitution mutant comprises a substitution of at least 5 amino acids. In another embodiment, a substitution mutant comprises a substitution of at least 6 amino acids. In another embodiment, a substitution mutant comprises a substitution of at least 8 amino acids. In another embodiment, a substitution mutant comprises a substitution of at least 10 amino acids.

In one embodiment, a mutation of the present invention comprises a substitution of a sequence of DNase I with the large loop in the CdtB sequence, which in one embodiment, is present in residues L261-S272, which is predicted to bind to CdtA, in one embodiment. In one embodiment, the DNase I fragment comprises a substitution of SEQ ID NO: 58 for SEQ ID NO: 59.

In another embodiment, a mutated Cdt toxin or a mutated Cdt toxin fragment comprises an insertion mutation, a deletion mutation, a substitution mutation, or any combination thereof. In another embodiment, a mutated CdtB toxin or a mutated CdtB toxin fragment comprises an insertion mutation, a deletion mutation, a substitution mutation, or any combination thereof. In another embodiment, a mutated DNase I or a mutated DNase I fragment comprises an insertion mutation, a deletion mutation, a substitution mutation, or any combination thereof.

In another embodiment, the sequence of a mutated chimera as provided herein may comprise the DNA sequence as set fourth in SEQ ID NOs: 28, 30, 32, 34, 36, or 38. In another embodiment, the sequence of a mutated chimera as provided herein may comprise the amino acid sequence as set fourth in SEQ ID NOs: 29, 31, 33, 35, 37, or 39.

In another embodiment, the chimera as provided herein is His-tagged. In another embodiment, the chimera as provided herein is $His_6$-tagged. In another embodiment, methods and compositions of the present invention utilize a chimeric molecule, comprising a fusion of a recombinant chimeric polypeptide with a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of the chimeric polypeptide is detected, in another embodiment, using an antibody against the tag polypeptide. In another embodiment, inclusion of the epitope tag enables the recombinant chimeric polypeptide to be readily purified by affinity purification using an anti-tag antibody or another type of affinity matrix that binds to the epitope tag. Various tag polypeptides and their respective antibodies are known in the art. Examples include poly-histidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide (Martin et al., Science, 255: 192-194 (1992)); a tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87: 6393-6397 (1990)). Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

In another embodiment, provided herein is a chimera comprising a Cdt fragment in the amino terminus of the chimera and a DNase I fragment in the carboxy terminus of the chimera. In another embodiment, provided herein is a chimera comprising a Cdt fragment in the amino terminus of the chimera and a homologue of a DNase I fragment in the carboxy terminus of the chimera. In another embodiment, provided herein is a chimera comprising a homologue of a Cdt fragment in the amino terminus of the chimera and a DNase I in the carboxy terminus of the chimera. In another embodiment, provided herein is a chimera comprising a homologue of a Cdt fragment in the amino terminus of the chimera and a homologue of a DNase I fragment in the carboxy terminus of the chimera.

In another embodiment, provided herein is a chimera comprising a CdtB fragment in the amino terminus of the chimera and a DNase I fragment in the carboxy terminus of the chimera. In another embodiment, provided herein is a chimera comprising a CdtB fragment in the amino terminus of the chimera and a homologue of a DNase I fragment in the carboxy terminus of the chimera. In another embodiment, provided herein is a chimera comprising a homologue of a CdtB fragment in the amino terminus of the chimera and a DNase I in the carboxy terminus of the chimera. In another embodiment, provided herein is a chimera comprising a homologue of a CdtB fragment in the amino terminus of the chimera and a homologue of a DNase I fragment in the carboxy terminus of the chimera.

In another embodiment, provided herein is a recombinant polypeptide comprising a chimera, wherein the recombinant polypeptide binds CdtC. In another embodiment, provided herein is a recombinant polypeptide comprising a chimera, wherein the recombinant polypeptide binds CdtA. In another embodiment, provided herein is a recombinant polypeptide comprising a chimera, wherein the recombinant polypeptide binds both CdtA and CdtC. In another embodiment, provided herein is a recombinant polypeptide consisting of a chimera, wherein the recombinant polypeptide binds both CdtA and CdtC. In another embodiment, provided herein is a recombinant polypeptide consisting of a chimera and a leader peptide, wherein the recombinant polypeptide binds both CdtA and CdtC. In another embodiment, provided herein is a recombinant polypeptide consisting a chimera and a signal peptide, wherein the recombinant polypeptide binds both CdtA and CdtC.

In another embodiment, provided herein is a recombinant polypeptide that inhibits proliferation of a cell. In another embodiment, provided herein is a recombinant polypeptide that inhibits proliferation of a eukaryotic cell. In another embodiment, provided herein is a recombinant polypeptide that inhibits proliferation of a neoplastic cell. In another embodiment, provided herein is a recombinant polypeptide that induces cell cycle arrest. In another embodiment, provided herein is a recombinant polypeptide comprising a chimera, wherein the recombinant polypeptide binds both CdtA and CdtC and induces cell cycle arrest. In another embodiment, provided herein is a recombinant polypeptide comprising a chimera, wherein the recombinant polypeptide binds CdtC and induces cell cycle arrest. In another embodiment, provided herein is a recombinant polypeptide comprising a chimera, wherein the recombinant polypeptide binds CdtA and induces cell cycle arrest. In another embodiment, provided herein is a recombinant polypeptide comprising a chimera, wherein the recombinant polypeptide binds both CdtA and CdtC and inhibits proliferation of a neoplastic cell. In another embodiment, provided herein is a recombinant polypeptide comprising a chimera, wherein the recombinant polypeptide binds CdtC and inhibits proliferation of a neoplastic cell. In another embodiment, provided herein is a recombinant polypeptide comprising a chimera, wherein the recombinant polypeptide binds CdtA and inhibits proliferation of a neoplastic cell.

In another embodiment, provided herein is a recombinant polypeptide comprising a chimera encoded by the DNA sequence of SEQ ID NO: 28, wherein the recombinant polypeptide binds both CdtA and CdtC and inhibits proliferation of a neoplastic cell. In another embodiment, provided herein is a recombinant polypeptide comprising a chimera encoded by the amino acid sequence of SEQ ID NO: 29, wherein the recombinant polypeptide binds both CdtA and CdtC and inhibits proliferation of a neoplastic cell.

In another embodiment, a chimera as described herein comprises a human DNase I/CdtB protein comprising potent supercoiled DNA nicking activity and cell delivery and nuclear localization mechanisms.

In another embodiment provided herein is a recombinant CdtA polypeptide comprising at least one of the mutations C149A and C178A, said polypeptide operably linked to a ligand that binds specifically to an antigen expressed on the surface of a cancerous epithelial cell type. In an exemplary embodiment, the antigen is prominin-1 or CD 133.

A prominin-1 peptide or protein can be attached to heterologous sequences to form chimeric or fusion proteins. Such chimeric and fusion proteins comprise a peptide operatively linked to a heterologous protein having an amino acid sequence not substantially homologous to the peptide. "Operatively linked" indicates that the peptide and the heterologous protein are fused in-frame. The heterologous protein can be fused to the N-terminus or C-terminus of the peptide.

In some uses, the fusion protein does not affect the activity of the peptide or protein per se. For example, the fusion protein can include, but is not limited to, beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant prominin-1 proteins or peptides. In certain host cells (e.g., mammalian host cells), expression and/or secretion of a protein can be increased by using a heterologous signal sequence.

A chimeric or fusion prominin-1 protein or peptide can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992-2006). Moreover, many expression vectors are commercially available that already encode a fusion moiety (e.g., a GST protein). A prominin-1-encoding nucleic acid can be cloned into such an expression vector such that the fusion moiety is linked in-frame to the prominin-1 protein or peptide.

Variants of the prominin-1 protein can readily be identified/made using molecular techniques and the sequence information disclosed herein. Further, such variants can readily be distinguished from other peptides based on sequence and/or structural homology to the prominin-1 peptides of the present invention. The degree of homology/identity present will be based primarily on whether the peptide is a functional variant or nonfunctional variant, the amount of divergence present in the paralog family and the evolutionary distance between the orthologs.

Antibodies that selectively bind to the prominin-1 protein or peptides of the present invention can be made using standard procedures known to those of ordinary skills in the art. The term "antibody" is used in the broadest sense, and specifically covers monoclonal antibodies (including full length monoclonal antibodies), polyclonal antibodies, multispecific antibodies (e.g., bispecific antibodies), chimeric antibodies, humanized antibodies, and antibody fragments (e.g., Fab, F(ab')$_2$, Fv and Fv-containing binding proteins) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity. Antibodies can be of the IgG, IgE, IgM, IgD, and IgA class or subclass thereof (e.g., IgG1, IgG2, IgG3, IgG4, IgA1 and IgA2).

As used herein, antibodies are usually heterotetrameric glycoproteins of about 150,000 daltons, composed of two identical light (L) chains and two identical heavy (H) chains (referred to as an "intact" antibody). Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains. Chothia et al., J. MoI. Biol. 186:651-63 (1985); Novotny and Haber, Proc. Natl. Acad. Sci. USA 82:4592-4596 (1985).

An "isolated" antibody is one which has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, the isolated antibody will be prepared by at least one purification step.

An "antigenic region" or "antigenic determinant" or an "epitope" includes any protein determinant capable of specific binding to an antibody. This is the site on an antigen to which each distinct antibody molecule binds. Epitopic determinants usually consist of active surface groupings of molecules such as amino acids or sugar side chains and usually have specific three-dimensional structural characteristics, as well as charge characteristics.

"Antibody specificity" refers to an antibody that has a stronger binding affinity for an antigen from a first subject species than it has for a homologue of that antigen from a second subject species. Normally, the antibody "binds specifically" to a human antigen (i.e., has a binding affinity (Kd) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second subject species which is at least about 50 fold, or at least about 500 fold, or at least about 1000 fold, weaker than its binding affinity for the human antigen. The antibody can be of any of the various types of antibodies as defined above, but preferably is a humanized or human antibody (see, e.g., Queen et al., U.S. Pat. Nos. 5,530,101; 5,585,089; 5,693,762; and 6,180,370).

The present invention provides an "antibody variant," which refers to an amino acid sequence variant of an antibody wherein one or more of the amino acid residues have been modified. Such variants necessarily have less than 100% sequence identity or similarity with the amino acid sequence and have at least 75% amino acid sequence identity or similarity with the amino acid sequence of either the heavy or light chain variable domain of the antibody, more preferably at least 80%, more preferably at least 85%, more preferably at least 90%, and most preferably at least 95%. Since the method of the invention applies equally to both polypeptides and antibodies and fragments thereof, these terms are sometimes employed interchangeably.

The term "antibody fragment" refers to a portion of a full-length antibody, including the antigen binding or variable region or the antigen-binding portion thereof. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')2 fragment that has two antigen binding fragments which are capable of crosslinking antigen, and a residual other fragment (which is termed pFc'). Additional antigen-binding fragments can include diabodies, triabodies, tetrabodies, single-chain Fv, single-chain Fv-Fc, a $SMIP_S$ and multispecific antibodies formed from antibody fragments. As used herein, a "functional fragment" with respect to antibodies, refers to an Fv, F(ab), $F(ab')_2$ or other antigen-binding fragments comprising one or more CDRs that has the same antigen-binding specificity as an antibody.

An "Fv" fragment is the minimum antibody fragment that contains a complete antigen recognition and binding site. This region consists of a dimer of one heavy and one light chain variable domain in a tight, non-covalent association ($V_H$-$V_L$ dimer). It is in this configuration that the three complementarity determining regions ("CDRs") of each variable domain interact to define an antigen-binding site on the surface of the VH-$V_L$ dimer. Collectively, the six CDRs confer antigen-binding specificity to the antibody. However, even a single variable domain (or half of an Fv comprising only three CDRs specific for an antigen) has the ability to recognize and bind antigen, although typically at a lower affinity than the entire binding site.

The Fab fragment [also designated as F(ab)] also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')2 pepsin digestion product. Additional chemical couplings of antibody fragments are known to those of ordinary skill in the art.

A "single-chain Fv" or "scFv" antibody fragment contains $V_H$ and $V_L$ domains, wherein these domains are present in a single polypeptide chain. Typically, the Fv polypeptide further comprises a polypeptide linker between the $V_H$ and $V_L$ domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). A single chain Fv-Fc is an scFv linked to a Fc region.

A "diabody" is a small antibody fragment with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., Proc. Natl. Acad. Sci. USA 90:6444-6448 (1993). Triabodies, tetrabodies and other antigen-binding antibody fragments have been described by Hollinger and Hudson, 2005, Nature Biotechnology 23:1126.

A "small modular immunopharmaceutical" or "SMIP" is a single-chain polypeptide including a binding domain (i.e., an scFv or an antigen binding portion of an antibody), a hinge region and an effector domain (e.g., an antibody Fc region or a portion thereof). SMIPs are described in Published U.S. Patent Application No. 2005-0238646.

The present invention further provides monoclonal antibodies, polyclonal antibodies as well as chimeric and humanized antibodies, and antigen-binding fragments thereof to prominin-1. In general, to generate antibodies, an isolated peptide is used as an immunogen and is administered to a mammalian organism, such as a rat, rabbit or mouse. The full-length prominin-1 protein, or an antigenic peptide fragment or a fusion protein thereof, can be used as an immunogen. Particularly important fragments are those covering functional domains, such as the extracellular domain or a portion thereof. Many methods are known for generating and/or identifying antibodies to a given target peptide. Several such methods are described by Harlow, Antibodies, Cold Spring Harbor Press (1989); Harlow and Lane, Using Antibodies, Cold Spring Harbor Press (1998); Lane, R. D., 1985, J. Immunol. Meth. 81:223-228; Kubitz et al., 1996, J. Indust. Microbiol. Biotech. 19:71-76; and Berry et al., 2003, Hybridoma and Hybridomics 22 (I): 23-31.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that substantially homogenous antibodies can be produced by a hybridoma culture which is uncontaminated by other immunoglobulins or antibodies. The modifier "monoclonal" antibody indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256: 495-497 (1975) or may be made by recombinant methods, e.g., as described in U.S. Pat. No. 4,816,567. The monoclonal antibodies for use with the present invention may also be isolated from phage antibody libraries using the techniques described in Clackson et al., Nature 352: 624-628 (1991), as well as in Marks et al., J. Mol. Biol. 222: 581-597 (1991).

"Humanized" forms of non-human (e.g., murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (a recipient antibody) in which residues from a complementary determining region (CDR) of the recipient are replaced by residues from a CDR of a non-human species (a donor antibody) such as mouse, rat or rabbit having the desired, specificity, affinity and capacity. In some instances, Fv framework residues of the human immunoglobulin are replaced by corresponding non-human residues. Furthermore, a humanized antibody may comprise residues which are found neither in the recipient antibody nor in the imported CDR or framework region (FR) sequences. These modifications are made to further refine and optimize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin consensus sequence. The humanized antibody optimally also will comprise at least a portion of an immunoglobulin constant region (Fc), typically that of a human immunoglobulin. For further details, see: Jones et al., Nature 321:522-525 (1986); Reichmann et al., Nature 332:323-327 (1988) and Presta, Curr. Op. Struct. Biol. 2:593-596 (1992).

Polyclonal antibodies may be prepared by any known method or modifications of these methods including obtaining antibodies from patients. For example, a complex of an immunogen such as prominin-1 protein, peptides or fragments thereof, and a carrier protein is prepared and an animal is immunized by the complex according to the same manner as that described with respect to the above monoclonal antibody preparation and the description in the Example. A serum or plasma containing the antibody against the protein is recovered from the immunized animal and the antibody is separated and purified. The gamma globulin fraction or the IgG antibodies can be obtained, for example, by use of saturated ammonium sulfate or DEAE SEPHADEX, or other techniques known to those skilled in the art.

The antibody titer in the antiserum can be measured according to the same manner as that described above with respect to the supernatant of the hybridoma culture. Separation and purification of the antibody can be carried out according to the same separation and purification method of antibody as that described with respect to the above monoclonal antibody and in the Example.

The antibodies of the present invention can also be generated using various phage display methods known in the art. In phage display methods, functional antibody domains are displayed on the surface of phage particles which carry the polynucleotide sequences encoding them. In particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen. or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187:9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibodies, e.g., antibody variants, can be also made recombinantly. When using recombinant techniques, the antibody variant can be produced intracellularly, in the periplasmic space, or directly secreted into the medium. If the antibody variant is produced intracellularly, as a first step, the particulate debris, either host cells or lysed fragments, is removed, for example, by centrifiigation or ultrafiltration. Carter et al., Bio/Technology 10: 163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifiigation. Where the antibody variant is secreted into the medium, supernatants from such expression systems are generally first concentrated using a commercially available protein concentration filter, for example, an Amicon or Millipore PELLICON ultrafiltration unit. A protease inhibitor such as PMSF may be included in any of the foregoing steps to inhibit proteolysis and antibiotics may be included to prevent the growth of adventitious contaminants.

The antibodies or antigen binding fragments may also be produced by genetic engineering. The technology for expression of both heavy and light chain genes in E. coli is the subject of PCT publication numbers WO 901443, WO901443, and WO 9014424 and in Huse et al., 1989 Science 246:1275-1281. The general recombinant methods are well known in the art.

The antibody composition prepared from the cells can be purified using, for example, hydroxylapatite chromatography, gel electrophoresis, dialysis, and/or affinity chromatography, with affinity chromatography being the preferred purification technique.

An antibody against Promin-1 may be coupled (e.g., covalently bonded) to a Cdt polypeptide either directly or indirectly (e.g., via a linker group). A direct reaction between an antibody and a therapeutic agent is possible when each possesses a substituent capable of reacting with the other. For example, a nucleophilic group, such as an amino or sulfhydryl group, on one molecule may be capable of reacting with a carbonyl-containing group, such as an anhydride or an acid halide, or with an alkyl group containing a good leaving group (e.g., a halide) on the other molecule.

Alternatively, it may be desirable to couple a Cdt polypeptide and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g. U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), by protease cleavable linker (e.g., U.S. Pat. No. 6,214,345), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody.

Regardless of the particular embodiment, conjugates with more than one agent may be prepared in a variety of ways as described herein.

In another embodiment, provided herein is a method for inhibiting the proliferation of a neoplastic cell comprising the step of contacting a cell with a recombinant polypeptide comprising a chimera as described herein or a nucleic acid molecule encoding the same, thereby inhibiting the proliferation of a neoplastic cell. In another embodiment, provided herein is a method for inhibiting the proliferation of a neoplastic cell comprising the step of contacting a cell with a nucleic acid molecule encoding a recombinant polypeptide comprising a chimera as described herein comprising the step of administering a DNA vector comprising said nucleic acid molecule. In one embodiment, methods of contacting a cell with a nucleic acid molecule by administering a DNA vector are known to one of skill in the art.

In another embodiment, the vector consists of a DNA sequence encoding a recombinant polypeptide comprising a chimera and a larger sequence that serves of the "backbone" of the vector. In another embodiment, the vector consists of a DNA sequence encoding a recombinant polypeptide consisting of a chimera and a larger sequence that serves of the "backbone" of the vector. In another embodiment, the vector multiplies in the target cell. In another embodiment, the vector is expressed in the target cell, thus expressing a recombinant polypeptide such as those described herein. In another embodiment, the vector is an expression vector.

In one embodiment, the formulations and methods of the instant invention comprise a nucleic acid sequence operably linked to one or more regulatory sequences. In one embodiment, a nucleic acid molecule introduced into a cell is in a form suitable for expression in the cell of the gene product encoded by the nucleic acid. Accordingly, in one embodiment, the nucleic acid molecule includes coding and regulatory sequences required for transcription of a gene (or portion thereof). When the gene product is a protein or peptide, the nucleic acid molecule includes coding and regulatory sequences required for translation of the nucleic acid molecule include promoters, enhancers, polyadenylation signals, sequences necessary for transport of an encoded protein or peptide.

In one embodiment, nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell Biol.* 9:2396), the creatine kinase gene (Buskin and Hauschka, (1989) *Mol. Cell Biol.* 9:2627) and the troponin gene (Mar and Ordahl, (1988) *Proc. Natl. Acad. Sci. USA.* 85:6404). Negative response elements in keratin genes mediate transcriptional repression (Jho Sh et al, (2001). J. Biol Chem). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus (CMV) and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S, and White, J. H. (1993) *Proc. Natl. Acad. Sci. USA* 90:5603-5607), synthetic ligand-regulated elements (see, e.g., Spencer, D. M. et al (1993) *Science* 262:1019-1024) and ionizing radiation-regulated elements (e.g., see Manome, Y. Et al. (1993) *Biochemistry* 32:10607-10613; Datta, R. et al. (1992) *Proc. Natl. Acad. Sci. USA* 89:1014-10153). Additional tissue-specific or inducible regulatory systems which may be developed can also be used in accordance with the invention.

In one embodiment, a regulatory sequence of the instant invention may comprise a CMV promoter, while in another embodiment, the regulatory sequence may comprise a CAG promoter. In one embodiment, a CAG promoter is a composite promoter that combines the human cytomegalovirus immediate-early enhancer and a modified chicken beta-actin promoter and first intron. In one embodiment, a regulatory sequence may comprise a simian virus (SV)-40 polyadenylation sequence, which in one embodiment, is the mechanism by which most messenger RNA molecules are terminated at their 3' ends in eukaryotes. In one embodiment, the polyadenosine (poly-A) tail protects the mRNA molecule from exonucleases and is important for transcription termination, for export of the mRNA from the nucleus, and for translation. In another embodiment, a formulation of the present invention may comprise one or more regulatory sequences.

In another embodiment, the vector comprises a promoter sequence that drives expression of the gene encoding a recombinant polypeptide comprising a chimera, as described herein. In another embodiment, the vector is a transcription vector.

In another embodiment, the promoter is a constitutively active promoter. In another embodiment, the promoter is an inducible promoter.

In another embodiment, the vector is a plasmid. In another embodiment, the vector is a viral vector. In another embodiment, the vector comprises an origin of replication. In another embodiment, the vector comprises a "multiple cloning site". In another embodiment, the vector is a bacterial vector. In another embodiment, a bacterial vector comprising a transgene encoding a recombinant polypeptide as described herein induces the expression of the recombinant polypeptide In another embodiment, the vector is a genetically-engineered virus. In another embodiment, the vector further comprises a helper virus or packaging lines for large-scale transfection. In another embodiment, the vector is designed for permanent incorporation of the insert into a host genome.

In another embodiment, methods for of contacting a cell with a nucleic acid provided herein include "naked DNA" technology. In another embodiment, methods including "naked DNA" technology result in transiently expressed recombinant polypeptide.

This invention provides, in one embodiment, a recombinant polypeptide comprising a chimera, wherein said chimera comprises a DNase I fragment or a homologue thereof and a Cdt fragment or a homologue thereof.

In one embodiment, "protein" or "polypeptide" refers to an amino acid chain comprising multiple peptide subunits, and may, in one embodiment, include a full-length protein, oligopeptides, and fragments thereof, wherein the amino acid residues are linked by covalent peptide bonds. In one embodiment, a protein described in the present invention may comprise a polypeptide of the present invention. In one embodiment, a protein is a multimeric structure. In one embodiment, a protein of the present invention is a holotoxin.

The term "native" or "native sequence" refers to a polypeptide having the same amino acid sequence as a polypeptide that occurs in nature. A polypeptide is considered to be "native" in accordance with the present invention regardless of its mode of preparation. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

As used herein in the specification and in the examples section which follows the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Either naturally occurring amino acids or non-conventional or modified amino acids may be used in the compositions and methods of the present invention.

As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

In another embodiment, the present invention provides a recombinant polynucleotide encoding a recombinant polypeptide comprising a chimera, wherein said chimera comprises a DNase I fragment or a homologue thereof and a Cdt fragment or a homologue thereof.

In one embodiment, the term "nucleic acid" or "polynucleotide" refers to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The nucleic acids can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

The term "promoter" means a nucleotide sequence that, when operably linked to a DNA sequence of interest, promotes transcription of that DNA sequence.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

The formulations of this invention may comprise nucleic acids, in one embodiment, or in another embodiment, the methods of this invention may include delivery of the same, wherein, in another embodiment, the nucleic acid is a part of a vector.

The efficacy of a particular expression vector system and method of introducing nucleic acid into a cell can be assessed by standard approaches routinely used in the art as described hereinbelow.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In another embodiment, the present invention provides a DNA vector comprising a recombinant polynucleotide encoding a recombinant polypeptide comprising a chimera, wherein said chimera comprises a DNase I fragment or a homologue thereof and a Cdt fragment or a homologue thereof.

In one embodiment, the term "vector" or "expression vector" refers to a carrier molecule into which a nucleic acid sequence can be inserted for introduction into a cell where it can be replicated. In one embodiment, the vector is a DNA vector. In one embodiment, the vector is a plasmid. In one embodiment, the nucleic acid molecules are transcribed into RNA, which in some cases are then translated into a protein, polypeptide, or peptide. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. In one embodiment the vector may be a shuttle vector, which in one embodiment can propagate both in prokaryotic and eukaryotic cells, or in another embodiment, the vector may be constructed to facilitate its integration within the genome of an organism of choice. The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus. In one embodiment, a vector is a plasmid.

In another embodiment, provided herein is a method for treating a neoplastic disease in a subject comprising the step of administering to a subject a recombinant polypeptide as described herein or a nucleic acid encoding the same, thereby treating a neoplastic disease in a subject.

In another embodiment, provided herein is a method for inhibiting or suppressing a neoplastic disease in a subject comprising the step of administering to a subject a recombinant polypeptide as described herein or a nucleic acid encoding the same, thereby inhibiting or suppressing a neoplastic disease in a subject.

In another embodiment, provided herein is a method for reducing the symptoms associated with a neoplastic disease in a subject comprising the step of administering to a subject the recombinant polypeptide as described herein or a nucleic acid encoding the same, thereby reducing the symptoms associated with a neoplastic disease in a subject.

In one embodiment, the present invention provides a method for inhibiting the proliferation of a neoplastic cell comprising the step of contacting said cell with a recombinant polypeptide comprising a chimera or a nucleic acid molecule encoding the same, wherein said chimera comprises a DNase I fragment or a homologue thereof and a Cdt fragment or a homologue thereof, thereby inhibiting the proliferation of a neoplastic cell.

In one embodiment, the present invention provides a method for treating a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby treating a neoplastic disease in a subject.

In one embodiment, the present invention provides a method for inhibiting or suppressing a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby inhibiting or suppressing a neoplastic disease in a subject.

In one embodiment, the present invention provides a method for reducing the symptoms associated with a neoplastic disease in a subject comprising the step of administering to said subject a recombinant polypeptide comprising a chimera or a nucleic acid encoding the same, wherein said chimera comprises a DNase I fragment or a homologue thereof and a Cdt fragment or a homologue thereof, thereby reducing the symptoms associated with a neoplastic disease in a subject.

In one embodiment, the present invention provides a method for inhibiting the proliferation of a neoplastic cell comprising the step of contacting said cell with a recombinant polypeptide comprising a chimera, wherein said chimera comprises a DNase I fragment or a homologue thereof and a Cdt fragment or a homologue thereof, thereby inhibiting the proliferation of a neoplastic cell.

In one embodiment, the present invention provides a method for treating a neoplastic disease in a subject comprising the step of administering to said subject a recombinant polypeptide comprising a chimera, wherein said chimera comprises a DNase I fragment or a homologue thereof and a Cdt fragment or a homologue thereof, thereby treating a neoplastic disease in a subject.

In one embodiment, the present invention provides a method for inhibiting or suppressing a neoplastic disease in a subject comprising the step of administering to said subject a recombinant polypeptide comprising a chimera, wherein said chimera comprises a DNase I fragment or a homologue thereof and a Cdt fragment or a homologue thereof, thereby inhibiting or suppressing a neoplastic disease in a subject.

In one embodiment, the present invention provides a method for reducing the symptoms associated with a neoplastic disease in a subject comprising the step of administering to said subject a recombinant polypeptide comprising a chimera, wherein said chimera comprises a DNase I fragment or a homologue thereof and a Cdt fragment or a homologue thereof, thereby reducing the symptoms associated with a neoplastic disease in a subject.

In one embodiment, the present invention provides a method for inhibiting the proliferation of a neoplastic cell comprising the step of contacting said cell with a nucleic acid molecule encoding a recombinant polypeptide comprising a chimera, wherein said chimera comprises a DNase I fragment or a homologue thereof and a Cdt fragment or a homologue thereof, thereby inhibiting the proliferation of a neoplastic cell.

In one embodiment, the present invention provides a method for treating a neoplastic disease in a subject comprising the step of administering to said subject a nucleic acid encoding a recombinant polypeptide comprising a chimera, wherein said chimera comprises a DNase I fragment or a homologue thereof and a Cdt fragment or a homologue thereof, thereby treating a neoplastic disease in a subject.

In one embodiment, the present invention provides a method for inhibiting or suppressing a neoplastic disease in a subject comprising the step of administering to said subject a nucleic acid encoding a recombinant polypeptide comprising a chimera, wherein said chimera comprises a DNase I fragment or a homologue thereof and a Cdt fragment or a homologue thereof, thereby inhibiting or suppressing a neoplastic disease in a subject.

In one embodiment, the present invention provides a method for reducing the symptoms associated with a neoplastic disease in a subject comprising the step of administering to said subject a nucleic acid encoding a recombinant polypeptide comprising a chimera, wherein said chimera comprises a DNase I fragment or a homologue thereof and a Cdt fragment or a homologue thereof, thereby reducing the symptoms associated with a neoplastic disease in a subject.

In one embodiment, the present invention provides a use of a recombinant polypeptide comprising a chimera or a nucleic acid molecule encoding the same, wherein said chimera comprises a DNase I fragment or a homologue thereof and a Cdt fragment or a homologue thereof in the preparation of a pharmaceutical composition for inhibiting the proliferation of a neoplastic cell.

In one embodiment, the present invention provides a use of a recombinant polypeptide comprising a chimera or a nucleic acid molecule encoding the same, wherein said chimera comprises a DNase I fragment or a homologue thereof and a Cdt fragment or a homologue thereof in the preparation of a pharmaceutical composition for treating a neoplastic disease in a subject.

In one embodiment, the present invention provides a use of a recombinant polypeptide comprising a chimera or a nucleic acid molecule encoding the same, wherein said chimera comprises a DNase I fragment or a homologue thereof and a Cdt fragment or a homologue thereof in the preparation of a pharmaceutical composition for inhibiting or suppressing a neoplastic disease in a subject.

In one embodiment, the present invention provides a use of a recombinant polypeptide comprising a chimera or a nucleic acid molecule encoding the same, wherein said chimera comprises a DNase I fragment or a homologue thereof and a Cdt fragment or a homologue thereof in the preparation of a pharmaceutical composition for reducing the symptoms associated with a neoplastic disease in a subject.

In one embodiment, a composition of the present invention is targeted to a rapidly proliferating cell, which in one embodiment, is an undifferentiated epithelial cell, and, in another embodiment, is a lymphocyte. In one embodiment, immortalized epithelial-like cell lines such as HeLa, KB, HEp-2 and GMSM-K (SV40 transformed) are particularly sensitive to Cdt, or in another embodiment, to Cdt-containing chimera of the present invention, or, in another embodiment, a CdtB-containing chimera of the present invention.

In one embodiment, a composition of the present invention may be used to treat, suppress, or inhibit a cancer of epitheloid origin, which in one embodiment, is a carcinoma, which in one embodiment, is a squamous cell carcinoma, adenocarcinoma, or transitional cell carcinoma, which in one embodiment, is a lung, breast, ovarian, or colon cancer. In one embodiment, the squamous cell carcinoma is oral squamous cell carcinoma. In one embodiment, breast cancer, prostate cancer, bladder cancer, brain cancer and hepatic cancer are of epitheloid origin.

In another embodiment, basal cell carcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, and skin cancer, such as squamous cell and basal cell cancers, renal cell carcinoma are of epitheloid origin. Other known cancers that effect epithelial cells throughout the body are known in the art.

In one embodiment, a neoplastic disease is a disease that involves the formation of a tumor or other abnormal tissue growth. In another embodiment, a neoplastic disease is a disease in which a neoplasm is present. In one embodiment, a neoplasm is an abnormal mass of tissue, the growth of which exceeds and is uncoordinated with that of the normal tissues, and persists in the same excessive manner after cessation of the stimulus which evoked the change. In one embodiment, a neoplasm does not form a tumor. In one embodiment, the neoplastic disease is malignant. In another embodiment, the neoplastic disease is pre-malignant. In another embodiment, the neoplastic disease is benign. In one embodiment, the neoplastic disease is a sarcoma, lymphoma, leukemia, carcinoma, or multiple myeloma. in one embodiment, the neoplastic disease is diagnosed in soft tissue tumors of the head and neck, skin, salivary glands, thyroid gland, breast, skeletal system, maxilla, orbit or, temporal fossa, nervous system, lungs, pleura or mediastinum, esophagus or stomach, small intestine, large intestine, liver or gallbladder, pancreas, kidneys, adrenal, glands, or, ureters-carcinoma, urinary bladder-carcinoma, cancers of the female genital tract, prostate gland, testicles, or penis.

In another embodiment, the compositions and methods of the present invention may be used for reducing the symptoms associated with neoplastic disease. Such symptoms are dependent on the location of the neoplastic disease, and are known to a skilled artisan and may, in one embodiment, include fevers, chills, night sweats, weight loss, loss of appetite, fatigue, malaise, or a combination thereof. In one embodiment, lung tumors can cause coughing, shortness of breath, or chest pain while, in one embodiment, tumors of the colon can cause weight loss, diarrhea, constipation and blood in the stool.

In one embodiment, the compositions and methods of the present invention may be used for treating, suppressing, or inhibiting tumor metastasis. In one embodiment, "metastasis" refers to the condition of spread of cancer from the organ of origin to additional distal sites in the patient.

In one embodiment, the compositions and methods of the present invention may be used for treating, suppressing, or inhibiting a "primary tumor", which, in one embodiment, is a tumor appearing at a first site within the subject and can be distinguished from a "metastatic tumor" which appears in the body of the subject at a remote site from the primary tumor. In one embodiment, a primary tumor is a solid tumor.

In one embodiment, the compositions and methods of the present invention may be used for treating, suppressing, or inhibiting wounds, ulcers, bronchitis, inflammatory conditions, herpes infection, or cystic fibrosis. In one embodiment, the compositions and methods of the present invention may be used for reducing the viscoelasticity of pulmonary secretions (mucus). In one embodiment, the compositions and methods of the present invention may be used for treating, suppressing, or inhibiting pneumonia and cystic fibrosis (CF). See e.g., Lourenco, et al., Arch. Intern. Med. 142:2299-2308 (1982); Shak, et al., Proc. Nat. Acad. Sci. 87:9188-9192 (1990); Hubbard, et al., New Engl. J. Med. 326:812-815 (1992); Fuchs, et al., New Engl. J. Med. 331:637-642 (1994); Bryson, et al., Drugs 48:894-906 (1994). In one embodiment, the compositions and methods of the present invention may be used for treating, suppressing, or inhibiting chronic bronchitis, asthmatic bronchitis, bronchiectasis, emphysema, acute and chronic sinusitis, the common cold, in which, in one embodiment, mucus also contributes to its morbidity.

The examples provided herein demonstrate that functional chimeras of the cdtB and human DNase I genes may be obtained and strongly supports the close relationship between the two gene products. The chimeric cdtB-DNase I genes were expressed in *E. coli* and the gene products exhibited nuclease activity, in vitro, comparable to that of CdtB. The fact that these artificial prokaryotic/eukaryotic gene constructs were expressed by *E. coli* and satisfied very stringent requirements to maintain a specific enzymatic activity provides compelling and novel evidence that the cdtB gene has evolved as an atypical divalent cation-dependent nuclease with remarkable similarities to mammalian DNase I.

In one embodiment, the successful construction of the chimeric genes indicates that there is significant potential to exploit the functional relationship between CdtB and human DNase Ito genetically engineer novel therapeutic reagents that take advantage of the most desirable features of each native protein. In one embodiment, DNase I has potent DNA-cutting/nicking activity. In one embodiment, CdtB can enter cells and translocate to the cell nucleus. Thus, in one embodiment, the CdtB portion or portions of the chimera allows cell entry and translocation of the chimera and the DNase I portion or portions of the chimera provide potent DNA-cutting/nicking activity. In one embodiment, the CdtB portion or portions of the chimera confers cell type specificity to the chimera, which in one embodiment, is specificity for epitheloid cells.

In another embodiment, the compositions of the present invention further comprise a targeting molecule used to target the chimera to a particular cell type of interest. In one embodiment, the targeting molecule is an antibody to a specific polypeptide expressed by a tumor or to a polypeptide expressed by a particular cell type. In one embodiment, somatostatin, neurotensin, bombesin receptor binding molecules, monoclonal antibodies, Penetratines™, or glycoproteins, may be used as targeting molecules. Other targeting molecules are known in the art.

In another embodiment, provided herein is a method for inhibiting the proliferation of a cancerous epithelial cell type comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, provided herein is a method for inhibiting the proliferation of a cancerous epithelial cell comprising: contacting said cell with a recombinant CdtA polypeptide comprising at least one of the mutations C149A and C178A, said polypeptide operably linked to a ligand that binds specifically to an antigen expressed on the surface of said cell.

In another embodiment, provided herein is a method for treating cancer comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, provided herein is a method for treating a disease associated with oral candidiasis comprising: administering a recombinant CdtA polypeptide comprising at least one of the mutations C149A and C178A, said polypeptide operably linked to a ligand that binds specifically to an antigen expressed on the surface of a cancerous epithelial cell type.

In another embodiment, provided herein is a method for treating a disease associated with oral candidiasis comprising: administering a toxin composition specific to *Candida albicans*, said toxin composition comprising a recombinant CdtA polypeptide comprising at least one of the mutations C149A and C178A, said polypeptide operably linked to a ligand that binds specifically to an antigen expressed on the surface of a cancerous epithelial cell type.

In one embodiment, "fragment" refers to a portion of a larger polypeptide or polynucleotide. In one embodiment, a fragment retains one or more particular functions as the larger molecule from which it was derived. In one embodiment, a fragment may maintain a functional domain, which in one embodiment, is a nuclear localization signal (NLS), a glycosylation site, a cleavage site, a binding site, a DNA contact site or residues, a G-actin binding site or residues, a metal binding site or residues, a Sph chimera fusion site, a catalytic His, a Hi hydrogen-bond pair, or a combination thereof. In one embodiment, a fragment may be approximately 50% of the length of the source polypeptide or polynucleotide.

In another embodiment, a fragment may be approximately 90% of the length of the source polypeptide or polynucleotide. In another embodiment, a fragment may be approximately 75% of the length of the source polypeptide or polynucleotide. In another embodiment, a fragment may be approximately 70% of the length of the source polypeptide or polynucleotide. In another embodiment, a fragment may be approximately 60% of the length of the source polypeptide or polynucleotide. In another embodiment, a fragment may be approximately 40% of the length of the source polypeptide or polynucleotide. In another embodiment, a fragment may be approximately 30% of the length of the source polypeptide or polynucleotide. In another embodiment, a fragment may be approximately 25% of the length of the source polypeptide or polynucleotide. In another embodiment, a fragment may be approximately 10% of the length of the source polypeptide or polynucleotide. In another embodiment, a fragment may be approximately 5% of the length of the source polypeptide or polynucleotide.

In another embodiment, a fragment is approximately 150 amino acids. In another embodiment, a fragment is approximately 180 amino acids. In another embodiment, a fragment is approximately 200 amino acids. In another embodiment, a fragment is 100-200 amino acids. In another embodiment, a fragment is 125-175 amino acids. In another embodiment, a fragment is 140-160 amino acids. In another embodiment, a fragment is 50-150 amino acids. In another embodiment, a fragment is the equivalent number of nucleic acids required to encode an amino acid as described, as would be understood by a skilled artisan.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

In another embodiment, a chimeric polypeptide or isolated nucleic acid of the present invention is homologous to a sequence set forth hereinabove, either expressly or by reference to a GenBank entry. The terms "homology," "homologous," etc, when in reference to any protein or peptide, or any sequence, whether amino acid or nucleotide sequence, refer, in one embodiment, to a percentage of amino acid residues or nucleic acid residues, as appropriate, in the candidate sequence that are identical with the residues of a corresponding native polypeptide or nucleic acid, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to the identity between two sequences being greater than 70%. In another embodiment, "homology" refers to the identity between two sequences being greater than 72%. In another embodiment, "homology" refers to the identity between two sequences being greater than 75%. In another embodiment, "homology" refers to the identity between two sequences being greater than 78%. In another embodiment, "homology" refers to the identity between two sequences being greater than 80%. In another embodiment, "homology" refers to the identity between two sequences being greater than 82%. In another embodiment, "homology" refers to the identity between two sequences being greater than 83%. In another embodiment, "homology" refers to the identity between two sequences being greater than 85%. In another embodiment, "homology" refers to the identity between two sequences being greater than 87%. In another embodiment, "homology" refers to the identity between two sequences being greater than 88%. In another embodiment, "homology" refers to the identity between two sequences being greater than 90%. In another embodiment, "homology" refers to the identity between two sequences being greater than 92%. In another embodiment, "homology" refers to the identity between two sequences being greater than 93%. In another embodiment, "homology" refers to the identity between two sequences being greater than 95%. In another embodiment, "homology" refers to the identity between two sequences being greater than 96%. In another embodiment, "homology" refers to the identity between two sequences being greater than 97%. In another embodiment, "homology" refers to the identity between two sequences being greater than 98%. In another embodiment, "homology" refers to the identity between two sequences being greater than 99%. In another embodiment, "homology" refers to the identity between two sequences being 100%.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7. 6), 5×Denhardt's solution, 10% dextran sulfate, and 20 µg/ml denatured, sheared salmon sperm DNA.

Homology for any amino acid or nucleic acid sequence listed herein is determined, in another embodiment, by methods well described in the art, including immunoblot analysis, or via computer algorithm analysis of amino acid sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In some embodiments, any of the chimeric polypeptides or nucleic acids of and for use in the methods of the present invention will comprise a DNase I fragment or a homologue thereof and a Cdt fragment or a homologue thereof, or an isolated nucleic acid encoded said components, in any form or embodiment as described herein. In some embodiments, any of the chimeric polypeptides or nucleic acids of and for use in the methods of the present invention will consist of a DNase I fragment or a homologue thereof and a Cdt fragment or a homologue thereof, or an isolated nucleic acid encoded said components of the present invention, in any form or embodiment as described herein. In some embodiments, the chimeric polypeptides or nucleic acids of this invention will consist essentially of a DNase I fragment or a homologue thereof and a Cdt fragment or a homologue thereof, or an isolated nucleic acid encoded said components of the present invention, in any form or embodiment as described herein. In some embodiments, the term "comprise" refers to the inclusion of other fragments of DNase I or Cdt, additional polypeptides, as well as inclusion of other proteins that may be known in the art. In some embodiments, the term "consisting essentially of" refers to a vaccine, which has a DNAse I polypeptide or fragment thereof and a Cdt fragment or a homologue thereof. However, other peptides may be included that are not involved directly in the utility of the chimeric polypeptide. In some embodiments, the term "consisting" refers to a chimeric polypeptide having the specific DNAse I polypeptide or fragment thereof and a Cdt fragment or a homologue thereof of the present invention, in any form or embodiment as described herein.

In one embodiment, a "chimeric" polypeptide or toxin is a protein or toxin created through the joining of two or more nucleotides or genes which originally coded for separate proteins. In one embodiment, translation of this fusion polynucleotide results in a single polypeptide with functional properties derived from each of the original proteins. In one embodiment, a chimeric polypeptide of the present invention comprises an IgE Fc or fragment thereof and a Cdt subunit.

Pharmaceutical Compositions

In another embodiment, the use of a recombinant polypeptide as described hereinabove and/or its analog, derivative, isomer, metabolite, pharmaceutically acceptable salt, pharmaceutical product, hydrate, N-oxide, or combinations thereof for treating, preventing, suppressing, inhibiting or reducing the incidence of cancer.

Thus, in one embodiment, the methods of the present invention comprise administering a recombinant polypeptide as described hereinabove. In another embodiment, the methods of the present invention comprise administering a derivative of the recombinant polypeptide as described hereinabove. In another embodiment, the methods of the present invention comprise administering an isomer of the recombinant polypeptide as described hereinabove. In another embodiment, the methods of the present invention comprise administering a metabolite of the recombinant polypeptide as described hereinabove. In another embodiment, the methods of the present invention comprise administering a pharmaceutically acceptable salt of the recombinant polypeptide as described hereinabove. In another embodiment, the methods of the present invention comprise administering a pharmaceutical product of the recombinant polypeptide as described hereinabove. In another embodiment, the methods of the present invention comprise administering a hydrate of the recombinant polypeptide as described hereinabove. In another embodiment, the methods of the present invention comprise administering an N-oxide of the recombinant polypeptide as described hereinabove. In another embodiment, the methods of the present invention comprise administering any of a combination of an analog, derivative, isomer, metabolite, pharmaceutically acceptable salt, pharmaceutical product, hydrate or N-oxide of the recombinant polypeptide as described hereinabove.

As used herein, "pharmaceutical composition" means a "therapeutically effective amount" of the active ingredient, i.e. the recombinant polypeptide as described hereinabove, together with a pharmaceutically acceptable carrier or diluent. A "therapeutically effective amount" refers, in one embodiment, to that amount which provides a therapeutic effect for a given condition and administration regimen.

The pharmaceutical compositions containing the recombinant polypeptide as described hereinabove can be administered to a subject by any method known to a person skilled in the art, such as parenterally, paracancerally, trans-mucosally, trans-dermally, intramuscularly, intravenously, intra-dermally, subcutaneously, intra-peritonealy, intra-ventricularly, intra-cranially, intra-vaginally or intra-tumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the recombinant polypeptide as described hereinabove is formulated in a capsule. In accordance with this embodiment, the compositions of the present invention comprise, in addition to the recombinant polypeptide as described hereinabove and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intraarterially and are thus formulated in a form suitable for intraarterial administration. In another embodiment, the pharmaceutical compositions are administered intramuscularly and are thus formulated in a form suitable for intramuscular administration.

Further, in another embodiment, the pharmaceutical compositions are administered topically to body surfaces and are thus formulated in a form suitable for topical administration. Suitable topical formulations include gels, ointments, creams, lotions, drops and the like. For topical administration, the recombinant polypeptides as described hereinabove or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the recombinant polypeptides as described hereinabove over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the recombinant polypeptide as described hereinabove is released over a period of time after administration. Controlled- or sustained-release compositions include formulation in lipophilic depots (e.g. fatty acids, waxes, oils). In another embodiment, the composition is an immediate-release composition, i.e. a composition in which all of the recombinant polypeptide as described hereinabove is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the recombinant polypeptide as described hereinabove or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the recombinant polypeptide as described hereinabove or their physiologically tolerated derivatives such as salts, esters, N-oxides, and the like are converted into a solution, suspension, or emulsion, if desired with the substances customary and suitable for this purpose, for example, solubilizers or other substances.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In one embodiment, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

In one embodiment, "treating" refers to either therapeutic treatment or prophylactic or preventative measures, wherein the object is to prevent or lessen the targeted condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

"Contacting," in one embodiment, refers to directly contacting the target cell with a chimeric polypeptide of the present invention. In another embodiment, "contacting" refers to indirectly contacting the target cell with a chimeric polypeptide of the present invention. Thus, in one embodiment, methods of the present invention include methods in which the subject is contacted with a chimeric polypeptide which is brought in contact with the target cell by diffusion or any other active transport or passive transport process known in the art by which compounds circulate within the body.

In one embodiment, the methods of the present invention comprising the step of administering a composition of the present invention to a subject in need. In one embodiment, "administering" refers to directly introducing into a subject by injection or other means a composition of the present invention. In another embodiment, "administering" refers to contacting a cell with a composition of the present invention. In one embodiment, the term "administering" refers to bringing a subject in contact with the recombinant polypeptide as described hereinabove. As used herein, administration can be accomplished in vitro, i.e. in a test tube, or in vivo, i.e. in cells or tissues of living organisms, for example humans. In one embodiment, the present invention encompasses administering the compounds of the present invention to a subject. In one embodiment, the compositions of the present invention are administered chronically, while in another embodiment, they are administered intermittently.

In one embodiment, "chronic" administration refers to administration of the agent(s) in a continuous mode as opposed to an acute mode, so as to maintain a desired effect or level of agent(s) for an extended period of time.

In one embodiment, "intermittent" administration is treatment that is not consecutively done without interruption, but rather is periodic in nature.

Administration "in combination with" or "in conjunction with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

In one embodiment, the methods of the present invention comprise administering a chimera as the sole active ingredient. In another embodiment, the present invention provides methods that comprise administering a chimera in combination with one or more therapeutic agents.

EXPERIMENTAL DETAILS SECTION

Materials and Methods

Construction of Chimeric cdtB Genes

Plasmids and primers used in this study are listed in Tables 1 and 2, respectively. All PCR and restriction digestion reactions were performed using standard techniques. Restriction endonucleases were purchased from New England Biolabs (Beverly, Mass.) and PCR oligonucleotide primers were obtained from Integrated DNA Technologies (IDT, Coralville, Iowa). Constructs were first selected in E. coli DH5α [supE44 ΔlacU169 (φ80lacZΔM15) hsdR17 recA1 endA1 gyrA96 thi-1 relA1] and transformed into E. coli BL-21 (DE3) for gene expression analysis and isolation of the gene product. Bacteria were grown in LB broth containing 75 μg/ml ampicillin at 37° C. with vigorous shaking. Plasmid DNA was isolated using either a QIAprep Miniprep (QIAGEN, Valencia, Calif.) or the Wizard Miniprep Kit (Promega Corporation, Fitchburg, Wis.). All constructs and mutations were confirmed by DNA sequencing. Automated cycle sequencing reactions were conducted by the DNA Sequencing Facility at the University of Pennsylvania Abramson Cancer Center using an Applied Biosystems 96-capillary 3730XL sequencer with BigDye Taq FS Terminator V 3.1.

The cdtB gene sequence used throughout these experiments was from construct pJDB7 originally made in Cao et al., (2005) and based on the sequence deposited in GenBank (accession no. AF006830). The full length DNase I sequence (GenBank accession no. AC005203) was amplified from plasmid GC-00001 (GeneCopoeia, Inc., Germantown, Md.) using the PCR primers N-DNase-F and X-DNase-R. This amplicon was cloned, in frame, to the His-tag in pETBlue2 (EMD Chemicals-Novagen, San Diego, Calif.) using NcoI and XhoI restriction endonuclease cleavage sites. Portions of the DNA sequence from the resulting clone, pJD1, were used to construct the chimeras. To construct the DNase I/cdtB gene chimera the 5'-half of the DNase I gene sequence was obtained by digestion of pJD1 with NcoI and SphI, the 3'-half of the cdtB gene was obtained by digesting pJDB7 with SphI and BamHI and pET15b was cut with NcoI and BamHI. The three DNA fragments were ligated to obtain pETDB1 (Table 1). To construct the cdtB/DNase I gene chimera the PCR primers N-cdtB-F and S-cdtB-R were used to amplify the 5'-half of cdtB using pJDB7 as the template DNA. pJD1 was digested with NcoI and SphI and the large DNA fragment was ligated to the pJDB7 amplicon after digestion with the same enzymes (clone pBDN1). The insert DNA fragment from pBDN1 was amplified using the PCR primers N-cdtB-F and NdeI-His and the amplicon was cloned into the NcoI and NdeI sites of pET15b. The resulting plasmid, pETBDN2, contained the cdtB/DNase I chimeric gene, with codons for a His-tag at the 3'-end, in the same vector background as the DNase I/cdtB gene chimera.

TABLE 1

Plasmids used in this study

| Plasmid | Features | Source or reference |
|---|---|---|
| GC-C0001 | human DNase I gene in pReceiver-B02 | GeneCopoeia |
| pJD1 | DNase I gene containing 6 His codons at 3'-end in pETBlue2 | This study |
| pJDB7 | cdtB gene containing 6 His codons at 3'-end in pET15b | Cao et al., 2005 |
| pMUT160cdtB | pJDB7 with substitution H160A | This study |
| pDN1 | human DNase I gene in pETBlue2 with 3'-His$_6$-tag | This study |
| pETDN1 | human DNase I gene containing 7 His codons at 3'-end in pET15b | This study |
| pBDN1 | cdtB/DNase I chimeric gene containing 6 His codons at 3'-end in pETBlue2 | This study |
| pETBDN1 | cdtB/DNase I hybrid gene in pET15b with 3'-His$_6$-tag | This study |
| pETBDN2 | cdtB/DNase I chimeric gene containing 7 His codons at 3'-end in pET15b | This study |
| pETDNB1 | DNase I/cdtB chimeric gene containing 6 His codons at 3'-end in pET15b | This study |
| pETBDNmut5 | pETBDN1 containing 5 codon changes in the hybrid gene (Table 4) | This study |
| pETBDN2-1 | pETBDN2 with substitutions S99Y and R100E | This study |
| pETBDN2-2 | pETBDN2-1 with substitution L62E | This study |
| pETBDN2-4 | pETBDN2-3 with substitution G55R | This study |
| pETBDN2-5 | pETBDN2-4 with substitution V134R | This study |
| pETBDN2-5LL | pETBDN2-5 with substitution N265-I275 to L265-T275 | This study |
| pETBlue2 | Cloning vector | Novagen |
| pET15b | Cloning vector | Novagen |

Amino Acid Substitutions Mutants

Amino acid substitutions were made in the CdtB/DNase I hybrid protein by site-directed mutagenesis as described previously (Cao et al., 2006). Synthetic oligonucleotide primer pairs were used to change S99Y and R100E (both in same primer), L62E, G55R and V134R. Briefly, mutant DNA strands were made using PfuUltra DNA polymerase (Stratagene, La Jolla, Calif.) in PCR. Plasmid DNA from pETBDN2 was used as the first PCR template. Additional mutations were then made sequentially using plasmid DNA from pETBDN2-1 to pETBDN2-5. Methylated parental DNA strands were digested with DpnI and the intact mutated DNA strand was transformed into E. coli TOP10 [F$^-$ mcrAΔ(mrr-hsdRMS-mcrBC) φ80lacZΔM15ΔlacX74 recA1 araD139Δ (ara-leu)7697 galU galK rpsL(str$^R$) endA1 nupG] chemically competent cells (Invitrogen, Carlsbad, Calif.). The mutations were confirmed by sequencing of the plasmid insert DNA from a single transformant.

The same strategy was used to change the active site H160 in CdtB-His$_6$ to Ala. DNA from pJDB7 was used as the PCR template for primers H160for and H160rev. The mutated protein from this clone was used as a negative activity control in the bioassays.

The large loop domain was added to CdtB/DNase I using an inverse PCR method (Cao et al., 2004) with the Loop-F and Loop-R primers (Table 2) and the insert fragment from pETBDN2-5 (Table 1), containing the cdtB/DNase I nucleotide sequence, as the template DNA. Codons for LMLNQLRSQIT (SEQ ID NO: 58) replaced NGLSDQLAQAI (SEQ ID NO: 59) in pETBDN2-5LL.

TABLE 2

Primers used in this study

| Name | Sequence* | SEQ ID NO: |
|---|---|---|
| N-DNase-F | 5'-AAATTA<u>CCATGG</u>TGAGGGGAATGAAGC-3' | 40 |
| X-DNase-R | 5'-TAATATT<u>CTCGAG</u>CTTCAGCATCACCT-3' | 41 |
| N-cdtB-F | 5'-AAACGCG<u>CCATGG</u>AGTGGGTAAAGCAAT-3' | 42 |
| S-cdtB-R | 5'-GGCCAAA<u>GCATGC</u>ACTGTAAAA-3' | 43 |
| NdeI-His | 5'-ATTAACTTAATTA<u>CATATG</u>GTGGTGGTGGTGGTGGTG-3' | 44 |
| DNaseI-His | 5'-TTT<u>GGATCC</u>GTGGTGGTGGTGGTGCTTCAGCATCAC-3' | 45 |
| H160Afor | 5-ACTGATGTATTTTTACAGTGGCTGCTTTGGCCACAGGTGG-3' | 46 |
| H160Arev | 5-CCACCTGTGGCCAAAGCAGCCACTGTAAAAATACATCAGT-3' | 47 |
| CdtB-DN-S99Y, R100E-F | 5'-GAGGAATATACCTGGAATTTAGGTACTCGCTATGAGCCAAATATGGTCTATATTA-TT-3' | 48 |
| CdtB-DN-S99Y, R100E-R | 5'-AATAAATATAGACCATATTTGGCTCATAGCGAGTACCTAAATTCCAGGTATATTC-CTC-3' | 49 |
| CdtB-DN-L62E-F | 5'-AATTATTATCGCGAGAACAAGGTGCAGATATTGAGATGGTACAAGAAGC-3' | 50 |
| CdtB-DN-L62E-R | 5'-GCTTCTTGTACCATCTCAATATCTGCACCTTGTTCTCGCGATAATAATT-3' | 51 |
| CdtB-DN-G55R-F | 5-AATGTGCGCCAATTATTATCGAGGGAACAAGGTGC-3' | 52 |
| CdtB-DN-G55R-R | 5'-GCACCTTGTTCCCTCGATAATAATTGGCGCACATT-3' | 53 |
| CdtB-DN-V134R-F | 5'-CAAGCCGATGAAGCTTTTATCCGACATTCTGATTCTTCTGTGCT-3' | 54 |
| CdtB-DN-V134R-R | 5'-AGCACAGAAGAATCAGAATGTCGGATAAAAGCTTCATCGGCTTG-3' | 55 |
| Loop-F | 5'-CGCTCACAAATTACAAGTGACCACTATCCAG-3' | 56 |
| Loop-R | 5'-TAACTGATTTAACATTAAGGCAGCCTGGAAG-3' | 57 |

*Underlined bases show the NcoI (CCATGG), XhoI (CTCGAG), SphI (GCATGC), NdeI (CATATG) and BamHI (GGATCC) restriction endonuclease cleavage sites. Bold type marks the changed codon(s).

Isolation of Gene Products and Heterotoxin Reconstitution

*Escherichia coli* BL-21(DE3) [F⁻ ompT hsdS$_B$ (r$_B$⁻ m$_B$⁻) gal dcm (DE3)] (Novagen) containing pJDA9 (wild-type CdtA-His$_6$), pJDC2 (wild-type CdtC-His$_6$), pJDB7 (wild-type CdtB-His$_6$), pMUT160cdtB (active site mutant), pETBDN2 (cdB-DNase I chimera), pETDNB1 (DNase I-cdB chimera) and pETBDN2-1 to pETBDN2-5(cdB-DNase I mutated chimera) were used to isolate gene products by affinity chromatography on nickel-iminodiacetic acid columns (Novagen) as described previously (Cao et al., 2005). All of the gene products have a His$_{6-7}$ tag at the carboxy-terminal end. The final protein preparations were dialyzed to remove urea, passed through 45 micron filters and quantified with the Micro BCA protein assay kit (Pierce, Rockville, Ill.). Purity was assessed by analysis on 10-20% polyacrylamide gels. The presence of the His-tag on all protein constructs was verified by western blotting using Anti-His•Tag Monoclonal Antibody (Novagen). Aliquots of the quantified protein samples were stored at −70° C. in a buffer containing 10 mM Tris-HCl (pH 7), 100 mM NaCl, 5 mM MgCl$_2$ and 5 mM imidazole for use in the various bioassays. Wild-type heterotoxin and heterotoxin containing hybrid and mutated hybrid proteins were reconstituted as described previously (Mao & DiRienzo, 2002). Attempts to purify recombinant human DNase I from either *E. coli* BL-21(DE3) (pJD1) or *E. coli* BL-21(DE3) (pETDN1) were unsuccessful most likely due to the poor expression of the human DNase I gene in *E. coli* as noted by Linardou et al. (2000).

In Vitro DNase Activity

Supercoiled DNA nicking activity was determined, with minor modifications, as described previously (Elwell & Dreyfus, 2000; Mao & DiRienzo, 2000). In a typical assay 1 μg of supercoiled pBluescript II SK(+) DNA (Sigma-Aldrich, St. Louis, Mo.) was incubated with 1 μg of wild-type, mutant or hybrid CdtB protein in 25 mM HEPES (Sigma-Aldrich) (pH 7.0) containing 50 mM MgCl$_2$ at 37° C. for 1 h. DNase I (0.1 ng), from bovine pancreas (Sigma-Aldrich), was used in place of human DNase I. Bovine DNase I is approximately 2.4-fold more active than the human homolog (Pan et al., 1998). Each form of DNA (supercoiled, relaxed, linear) was quantified and compared using ImageJ version 1.34 (http://rsb.info.nih.gov/ij/) and digitized images of ethidium bromide-stained gels. Protein and divalent cation concentrations were varied in some kinetic and biochemical analyses.

Heat lability was compared by pretreating proteins at 100° C. for up to 30 min prior to determining DNA nicking activity. Actin inhibition of DNA nicking activity was performed essentially as described by Ulmer et al, (1996). Rabbit skeletal muscle G-actin (Sigma-Aldrich) was de-polymerized at room temperature for 15 min in a buffer containing 25 mM HEPES (pH 7.5), 5 mM CaCl$_2$, 5 mM MgCl$_2$, 0.1% BSA, 0.05% Tween 20 and 0.5 mM 2-mecaptoethanol. Five micrograms of the depolymerized G-actin were preincubated with 1 μg of CdtB-His$_6$ or 0.1 ng of bovine DNase I for 60 min at 37° C. The treated proteins were then examined in the nicking assay. Subunit protection of DNA nicking activity was assessed as described previously (Nešić et al., 2004) except that incubation was performed at room temperature for 1 hour.

In Vivo CdtB Activity

Cell proliferation was measured with a colony-forming assay employing CHO cells [300 cells in 3 ml of medium per well (6-well plate) in triplicate] as described in Mao & DiRienzo (2002). The number of colonies per well was expressed as colony-forming units (CFU). A dose response curve for wild-type reconstituted heterotoxin has been published (Cao et al., 2005). Cell cycle arrest was determined by flow cytometry of propidium iodide stained nuclei as described previously (Cao et al., 2005).

Binding Kinetics

Saturation kinetics were used to assess binding of the hybrid and mutated hybrid proteins to wild-type CdtA-His$_6$ and CdtC-His$_6$ in a thyroglobulin ELISA (Cao et al., 2005).

Wild-type CdtA-His$_6$ (4.0 µg) and CdtC-His$_6$ (3.5 µg) were added to thyroglobulin-coated wells. Hybrid or mutated hybrid protein (0-4 µg) was then added to triplicate wells. Bound protein was detected with a 1×10$^{-6}$ dilution of anti-CdtB IgG rabbit antiserum and a 1×10$^{-3}$ dilution of donkey anti-rabbit IgG-horseradish peroxidase conjugate (Amersham Pharmacia Biotech, Piscataway, N.J.) (Cao et al., 2008). The ability of the hybrid and mutated hybrid proteins to bind the other subunits was also determined by stoichiometric binding in the thyroglobulin ELISA as described previously (Cao et al., 2005). Wild-type CdtA-His$_6$ was prebound to thyroglobulin-coated 96-well microtiter plates as described above. Hybrid and mutated hybrid proteins (4.5 µg) and wild-type CdtC-His$_6$ (3.5 µg) were added to triplicate wells. Total bound protein was detected with anti-His•Tag monoclonal antibody and anti-mouse IgG horseradish peroxidase conjugate both at a 1×10$^{-3}$ dilution. An absorbance ratio of 3.0 is indicative of the binding of the hybrid or mutated hybrid protein to the other two subunits. CdtB-His$_6$ and DNase I do not bind to thyroglobulin. ELISA plates were washed in a BioTek Model EL405 HT microplate washer (BioTek Instruments, Inc., Winooski, Vt.). Absorbance values were obtained with a BioTek Synergy 2 Multi-Detection Microplate Reader.

Differential dialysis was performed as described previously using dialysis membrane with a molecular weight exclusion limit of 100 kDa (Spectrum Laboratories, Inc., Rancho Dominguez, Calif.) (Cao et al., 2008). Immunopositive bands on western blots were quantified with ImageJ.

Computer Modeling

The European Molecular Biology Open Software Suite (EMBOSS release 3.0; http://emboss.sourceforge.net) (Rice et al., 2000) was used to obtain the deduced amino acid sequences for cdtB-His$_6$ (from pJDB7), cdtB/DNase I, DNase I/cdtB and human DNase I (from pETDN1) and to create the alignment using ClustalX 1.83. The crystal structures of the *A. actinomycetemcomitans* Y4 Cdt (Yamada et al., 2006) and bovine DNase I were modeled with UCSF Chimera 1.2197 (http://www.cgl.ucsf.edu/chimera/) (Pettersen et al., 2004). Coordinates were obtained from the Protein Data Bank (accession nos. 2F2F and 3DNI, respectively). Human DNase I has not been crystallized. CdtB/DNase I and DNase I/CdtB structures were predicted using Modeller version 9v1 (http://salilab.org/modeller/) (Marti-Renom et al., 2000).

Polyclonal CdtB and CdtC Antisera

Subunit protein specific antisera for CdtB-His$_6$ and CdtCHis$_6$, used in some experiments, were made in rabbits (Cocalico Biologicals, Inc., Reamstown, Pa.). IgG fractions were purified using a Montage Antibody Purification Kit (Millipore, Billerica, Mass.). IgG titers were obtained by ELISA using purified CdtB-His$_6$ and CdtC-His$_6$ as antigens. Cross-reactivity with all three Cdt proteins was assessed by western blotting. Bound IgG was detected with a 1:3000 dilution of donkey anti-rabbit IgG-horseradish peroxidase conjugate (Amersham Pharmacia Biotech).

EXAMPLE 1

Using a CdtB/DNase I Hybrid Protein as a Therapeutic Agent

In spite of the phylogenetic relationship (FIG. 14) in CdtB/DNase, there are key biological, compositional and structural differences between the CdtB and DNase I (Table 3). However, the similarities between these proteins are strong enough to suggest that genetic modification is possible to adapt them for potential use as growth inhibitors of cancer cells.

TABLE 3

Comparison of physical and biochemical properties of CdtB and DNase I

| Property | CdtB *A. actinomycetemcomitans* | DNase I human | bovine |
|---|---|---|---|
| Number of amino acids | 283 | 282 | 261 |
| Molecular weight (Da)$^a$ | 31,494 | 31,434 | 29,183 |
| pI$^b$ | 7.8 | 3.5-4.3 | 4.7-5.2 |
| Disulfide | no | yes (C124-C127, C196-C232) | yes (C102-C105, C174-C210) |
| Carbohydrate modification$^c$ | no | yes (N18 and N106) | yes (N18) |
| in vitro DNA nicking activity | yes | Yes | yes |
| Actin inhibition | no | Yes | yes |
| Cations required for activity | Mg$^{++}$ or Ca$^{++}$ or Mn$^{++}$ | Mg$^{++}$ or Ca$^{++}$ or Mn$^{++}$ | Mg$^{++}$ or Ca$^{++}$ or Mn$^{++}$ |
| Specific activity for nicking dsDNA$^d$ | 100-1000 fold less | 2.4 fold less | — |

$^a$Calculated molecular weight without carbohydrate moiety [additional 1.3 kDa per carbohydrate chain (NAG$_2$-MAN$_5$); 2 chains bovine, 1 chain human]
$^b$Range due to heterogenity in glycosylation
$^c$Amino acid location from processed proteins (minus signal sequence)
$^d$Relative to bovine DNase DNase I cannot enter cells unaided. Even with some type of physical-, immuno- or ligand-based transport system the protein would not migrate to the cell nucleus. In contrast, CdtB appears to be taken up by cells (possibly with CdtC) via the Golgi complex and transported to the endoplasmic reticulum. However, this uptake occurs only after the Cdt binds to the susceptible cell. Initial binding may be to cholesterol-rich membrane patches (possibly lipid rafts). The CdtB travels to the nucleus by an unknown mechanism and gains access to the chromatin via a nuclear localization sequence. The CdtB sends the cells on a destructive pathway due to activation of DNA damage checkpoint responses leading to growth arrest or apoptosis. These effects are most pronounced in rapidly proliferating cells such as undifferentiated epithelial cells and lymphocytes. The experiments performed revealed that immortalized epithelial-like cell lines such as HeLa, KB, HEp-2 and GMSM-K (SV40 transformed) are particularly sensitive to the toxin. In contrast, oral primary fibroblast-like cell types including human periodontal ligament fibroblasts (HPLF), human gingival fibroblasts (HGF), cementoblasts, and osteoblasts are resistant to the DNA-damaging and cytotoxic effects of the Cdt.

The fact that CdtB is phylogenically related to human DNase I provides an additional advantage over typical prokaryotic-based recombinant toxins. Furthermore, the DNA-damaging strategy (double-strand DNA breaks) of the CdtB subunit of Cdt is likened to the effects of ionizing radiation. Targeting a potent DNA-damaging protein to the nucleus of cancer cells is analogous to a form of localized radiation therapy.

EXAMPLE 2

Kinetic Analysis of Recombinant CdtB-His$_6$ from *A. Actinomycetemcomitans* and Bovine DNase I The difference in specific activities between recombinant CdtB-His$_6$ and bovine DNase I is exemplified in FIG. 1. Purified recombinant *A. actinomycetemcomitans* Y4 CdtB from pJDB7 (FIG. 1*a*), converted supercoiled [superhelical (S) circular, Form I] plasmid DNA to relaxed [(R) nicked circular, Form II] and linear [(L) Form III] forms with dose dependent kinetics in the standard DNA nicking assay (FIG. 1*b*). This conversion was not affected by the location (amino- or carboxy-terminus) of the His$_6$-tag. One μg of recombinant CdtB-His$_6$ converted 95% of 1 μg of supercoiled plasmid DNA to relaxed or linear forms in 1 hour at 37° C. The substitution mutant CdtBH160A (from pMUT160cdtB in Table 1) had no effect on supercoiled plasmid DNA confirming that recombinant CdtB-His$_6$ preparations were not contaminated with *E. coli* nucleases (data not shown). In comparison, 0.1 ng bovine DNase I converted 100% of 1 μg of supercoiled plasmid DNA to relaxed form in 1 hour at 37° C. (FIG. 1*c*). A ten-fold higher concentration of DNase I converted 98% of 1 μg of supercoiled DNA to linear form and a 100-fold higher concentration of the nuclease completely digested the DNA into small fragments. Based on these results, the specific activity of recombinant CdtB-His$_6$ was estimated to be as much as $10^3$-fold lower than that of bovine DNase I.

Maximum conversion of supercoiled DNA to relaxed and linear forms was obtained with either 50 mM MgCl$_2$, CaCl$_2$ or MnCl$_2$ (FIG. 2). Reactions containing CaCl$_2$ consistently failed to go to completion. CdtB-His$_6$ nuclease activity was inhibited by MgCl$_2$, CaCl$_2$ and MnCl$_2$ when the cation concentrations were greater than 150-200 mM. No conversion of supercoiled DNA was observed at any divalent cation concentration in the absence of CdtB and various combinations of the cations (50 mM of each) did not affect digestion patterns relative to those obtained with the individual cations. A time course of digestion with 50 mM MgCl$_2$ in the reaction established that 1 μg of CdtB-His$_6$ completely converted 1 μg of supercoiled DNA to relaxed and linear forms in 1 hour at 37° C. (data not shown). Incubation times of 2 hours or greater generated more linear form DNA. Thus, CdtB-His$_6$ requires either Mg++, Ca++ or Mn++ at an individual or combined concentration of 50 mM for optimum activity. This is a 10-fold higher concentration than that required for optimum DNase I activity (Price, 1975). The standard in vitro DNase activity assay used in all subsequent experiments contained 50 mM MgCl$_2$.

Cdt-B-His$_6$ retained greater than 90% of its DNA nicking activity following incubation for 5 min in a boiling water bath (FIG. 3A). There was a loss of virtually all enzymatic activity after heating for 10 min. In contrast, bovine DNase I DNA nicking activity was less than 50% of the control after 5 min of heating (FIG. 3B). The DNA nicking activity of both enzymes was significantly more heat stable than the double-strand cleavage activity.

CdtB-His$_6$ is not inhibited by G-actin (FIG. 4). These results confirmed that both CdtB-His$_6$ and bovine DNase I have supercoiled DNA-nicking activity and that the two enzymes can be distinguished by several key biochemical properties (Table 3).

EXAMPLE 3

Characterization of CdtB/DNase I and DNase I/CdtB Chimeric Genes and Gene Products Notable differences between the biochemical properties of CdtB and DNase I suggested that a genetic strategy based on the analysis of the products of chimeric genes could be used to further examine functional similarities and differences between the two proteins. This approach was facilitated by the presence of a unique SphI restriction endonuclease cleavage site at approximately the mid-point of both wild-type gene sequences. Using each half of the CdtB-His$_6$ and human DNase I gene sequences two genetic constructs, pETBDN2 and pETDNB1 containing the chimeric ORFs cdtB/DNase I and DNase I/cdtB, respectively (Table 1) were made. Both ORFs were placed immediately downstream from a highly efficient, inducible promoter and contained six or seven histidine codons in frame at the 3'-end of each sequence.

Two active site catalytic histidines are conserved in CdtB from *A. actinomycetemcomitans* and bovine DNase I (FIG. 5A). A deduced amino acid sequence alignment showed that both hybrid gene products contain the two histidines [residues H160/157 and H278/271 in CdtB/DNase I and DNase I/CdtB, respectively] (FIG. 5C). Computer modeling indicated that only the CdtB/DNase I hybrid protein maintained a folded structure similar to those of native CdtB and DNase I (FIG. 5B). However, both hybrid proteins exhibited optimum in vitro supercoiled DNA nicking activity in the presence of 50 mM MgCl$_2$. The DNA nicking activity of CdtB/DNase I was not affected after incubation in a boiling water bath for 5 min but there was a significant reduction in the DNA nicking activity of DNase I/CdtB after the same treatment (FIG. 3). In contrast to bovine DNase I, G-actin had no effect on the ability of CdtB-His$_6$ and CdtB/DNase I to convert supercoiled DNA to relaxed and linear forms. Conversely, actin inhibited the DNA nicking activity of DNase I/CdtB (FIG. 4). The results of these assays demonstrated that the amino terminal portions of CdtB and DNase I carry the biochemical properties of thermostability and actin binding, respectively.

EXAMPLE 4

Subunit Assembly of CdtB/DNase I and DNase I/CdtB Hybrid Proteins

Figure 6B:
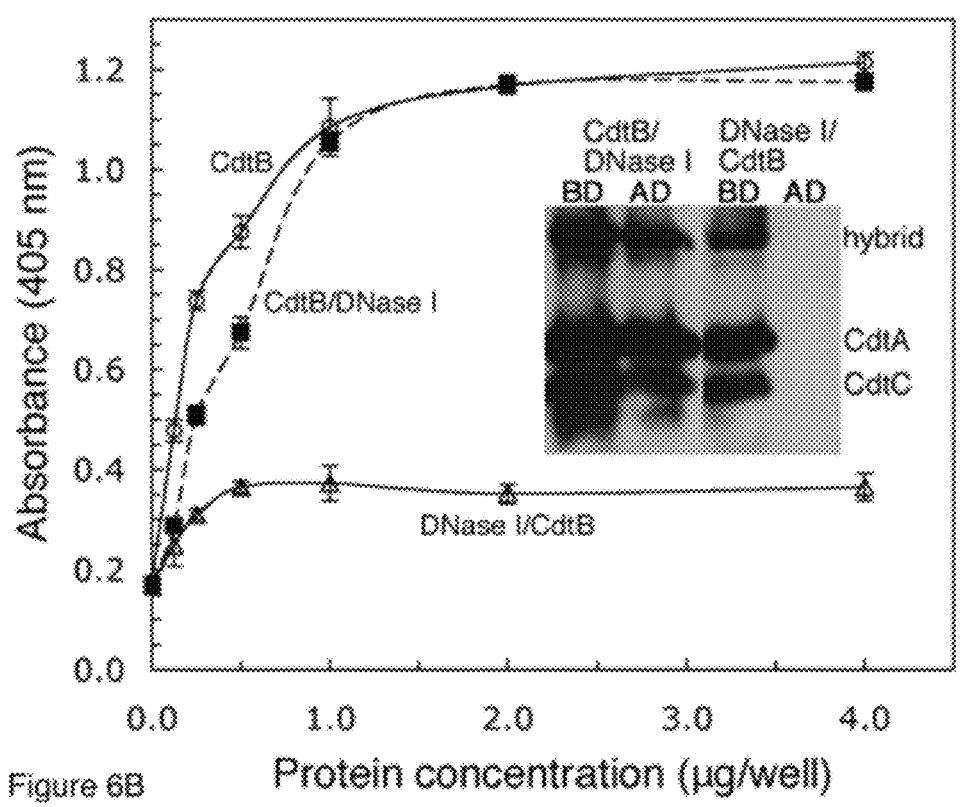
Figure 6C:
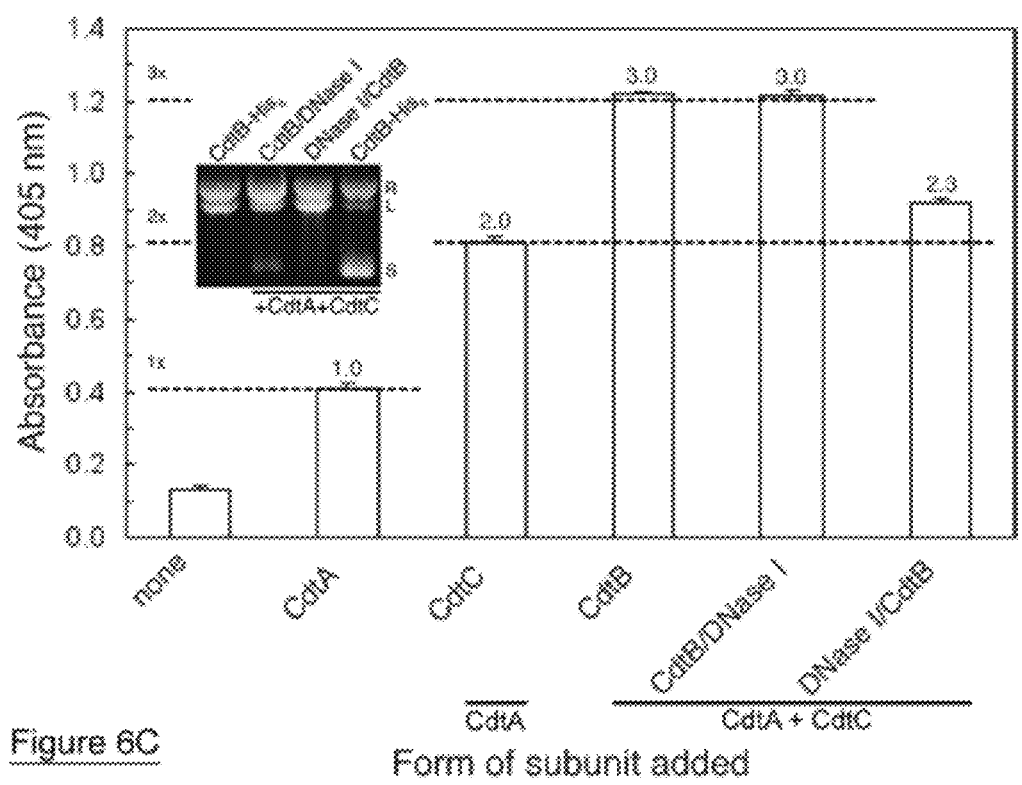

The ability of the hybrid proteins to form biologically active reconstituted heterotoxin was tested. Each hybrid protein was mixed with wild-type CdtA and CdtC in refolding buffer as described previously. CHO cell cultures were then treated with the reconstituted preparations. Neither hybrid protein yielded a biologically active heterotoxin as measured in the cell proliferation assay (FIG. 6A). A property specific to CdtB is the ability to bind the CdtA and CdtC subunits to form a biologically active heterotrimer. CdtB/DNase I but not DNase I/CdtB bound to CdtA-CdtC heterodimer at concentrations comparable to CdtB-His$_6$ (FIG. 6*b*). Both the CdtB-His$_6$ control and CdtB/DNase I hybrid proteins reached saturation binding at approximately 3-4 μg per 4.0 μg of CdtA-His$_6$ and 3.5 μg of CdtC-His$_6$. Consistent with these results, CdtB/DNase I but not DNase I/CdtB, formed a heterotrimer complex in the differential dialysis assay (FIG. 6*b*; inset). In addition, CdtB/DNase I but not DNase I/CdtB bound stoichiometrically to CdtA and CdtC (FIG. 6*c*) and reconstituted heterotrimer preparations containing the CdtB/DNase I hybrid protein failed to convert supercoiled DNA to linear and relaxed forms (FIG. 6c; inset). Although these four independent assays established that the CdtB/DNase I hybrid protein formed a heterotrimer, this complex failed to inhibit the proliferation and cell cycle progression of CHO cells.

Computer modeling of the two hybrid proteins provided supporting evidence for reconciling the results of the proliferation inhibition (FIG. 6A) and thyroglobulin ELISA (FIG. 6B) assays. There are two structural domains in CdtB, an α-helix labeled H1 (residues N41-S54) and a large loop (residues L261-S272), that are predicted to be important for the binding of this subunit to CdtC and CdtA, respectively (FIGS. 5 and 7). A modeled ribbon structure of the CdtB/DNase I hybrid protein shows that α-helix H1, located in the amino terminal half of CdtB, is still present but the large loop, located in the carboxy-terminal half of CdtB is missing. The presence of only the α-helix H1 suggests that CdtB/DNase I is capable of binding only to CdtC. Addition of the large loop CdtA-binding domain to CdtB/DNase I is discussed below. In contrast, the ribbon model of the DNase I/CdtB hybrid protein contains only the large loop structure and displays a significant change in overall protein conformational relative to that of the native CdtB.

EXAMPLE 5

Figure 8:
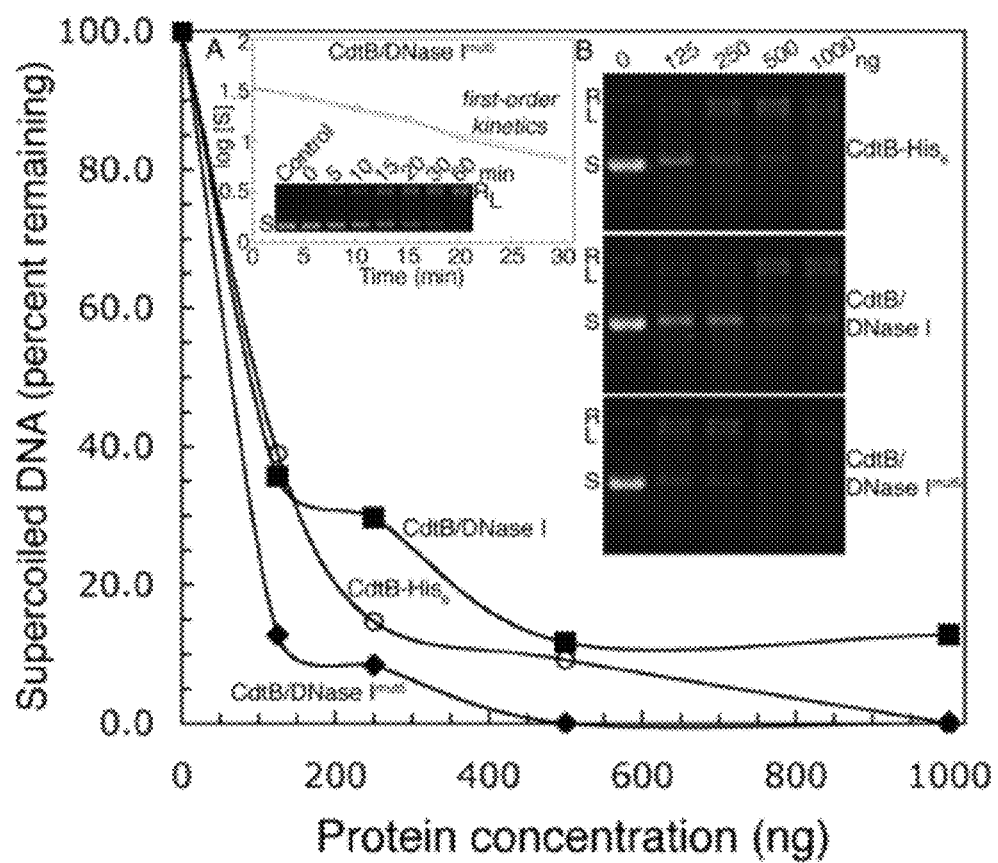

Effect of Targeted Amino Acid Substitutions on the DNA Nicking and Subunit Binding Activities of CdtB/DNase I Since the DNase I/CdtB hybrid protein failed to bind CdtA and CdtC (FIG. 6), lacked a key domain for nuclear localization (FIG. 5C) and appeared to have an unfolded conformation in computer models (data not shown), it was not studied further. Single amino acid substitutions were sequentially made in the CdtB/DNase I hybrid protein based on the results from mutagenesis studies of the bovine and human forms of the DNase I gene (Pan et al., 1998). Substitutions G55R, S99Y and V134R added DNA contact residues, L62E added a metal ion binding residue and R100E added a residue that hydrogen bonds to the catalytic H160 in DNase I (FIG. 5C and Tables 1 and 4). Five hundred ng of the final mutated hybrid gene product, CdtB/DNase I$^{mut5}$ (clone pETBDN2-5), converted 100% of 1 μg of supercoiled DNA to relaxed and linear forms under standard assay conditions resulting in an approximately 1.4-fold increase in specific activity relative to CdtB-His$_6$ and CdtB/DNase I (FIG. 8 and inset B). CdtB/DNase I$^{mut5}$ exhibited classical first-order kinetics (inset A).

TABLE 4

Successive amino acid substitutions made in the CdtB/DNase I hybrid protein.

| Amino acid substitution | Position (residue number)[a] | Description of mutation |
|---|---|---|
| R→E | 100 | Add acidic residue that forms a hydrogen-bond pair with catalytic His residue 160 |
| G→R | 55 | Add DNA contact residue |
| S→Y | 99 | Add DNA contact residue |
| V→R | 134 | Add DNA contact residue |
| L→E | 62 | Add metal ion binding residue |

[a]Based on the deduced amino acid sequence alignment of CdtB/DNase I and human DNase I (see FIG. 5).

EXAMPLE 6

Cdt-Induced Cell Cycle Arrest of Human Cancer Cell Lines

As a prelude to determining the therapeutic efficacy of heterotoxin reconstituted with CdtB/DNase I$^{mut5}$, experiments were initiated to detail the response of established human cancer cell lines to the native Cdt. Four cancer cell lines derived from carcinomas of the tongue, nasal septum and pharynx were purchased from the American Type Culture Collection (ATCC) (Table 5). HeLa cells were used as a transformed human cell control. The response of the cancer cell lines to that of normal primary human gingival epithelial cells (HGEC strain AL-1) which have been recently isolated and cultured in our laboratory was performed. Each of the cell lines were treated with reconstituted recombinant A. actinomycetemcomitans Cdt for 24 hours and effects on the cell cycle were assessed by flow cytometry as described previously. All four Cdt-treated cancer cell cultures exhibited a significant accumulation of cells having a 4n DNA content indicative of a G$_2$ block in cell cycle progression (Table 5). The portion of the cancer cell populations having a 4n DNA content ranged from 49-70 percent compared to 44 and 45 percent for HeLa and A1-1 cells, respectively. The accumulation of Cdt-treated CAL-27 cells at the G$_2$/M interphase of the cell cycle is shown, compared to controls, as an example in FIG. 9.

Thus, all of the cancer cell lines examined exhibited cell cycle arrest and on average appeared to be more sensitive to the Cdt then the HeLa cells and normal primary HGEC. These cancer cell lines were used in experiments described below to test the cytotoxic effects of heterotrimer made with the final genetically modified hybrid protein. These cells are used to generate solid tumors in mice to test the efficacy of the hybrid protein.

Table 5. Cell Cycle Analysis of Cancer Cell Lines Treated with Reconstituted Cdt

TABLE 4

Cell cycle analysis of cancer cell lines treated with reconstituted Cdt

| ATCC number | Cell line[a,b] | Source | Disease | Treatment | Diploid G1 (2n) (%) | Diploid G2 (4n) (%) | Diploid S (%) | Coefficient of variance (%) |
|---|---|---|---|---|---|---|---|---|
| CRL-1624 | SCC-4 | tongue | squamous cell carcinoma | none | 73.98 | 7.42 | 18.59 | 5.33 |
| | | | | Cdt | 17.90 | 63.52 | 18.58 | 4.61 |
| CRL-2095 | CAL-27 | tongue | squamous cell carcinoma | none | 74.35 | 2.04 | 23.61 | 5.57 |
| | | | | Cdt | 39.23 | 49.01 | 11.76 | 3.74 |
| CCL-30 | RPMI 2650 | nasal septum | squamous cell carcinoma | none | 73.87 | 8.71 | 17.43 | 4.25 |
| | | | | Cdt | 11.38 | 69.90 | 19.02 | 4.37 |
| HTB-43 | FaDu | pharynx | squamous cell carcinoma | none | 62.00 | 3.91 | 34.09 | 3.96 |
| | | | | Cdt | 22.01 | 56.06 | 21.93 | 4.46 |

TABLE 4-continued

Cell cycle analysis of cancer cell lines treated with reconstituted Cdt

| ATCC number | Cell line[a,b] | Source | Disease | Treatment | Diploid G1 (2n) (%) | Diploid G2 (4n) (%) | Diploid S (%) | Coefficient of variance (%) |
|---|---|---|---|---|---|---|---|---|
| CCL-2 | HeLa | cervix | adenocarcinoma | none | 65.16 | 1.22 | 33.62 | 5.86 |
|  |  |  |  | Cdt | 39.19 | 43.58 | 17.23 | 4.16 |
| — | AL-1 | human gingiva | none | none | 43.57 | 24.42 | 32.01 | 8.43 |
|  |  |  |  | Cdt | 26.89 | 45.40 | 27.61 | 5.02 |

[a]All are adherent cells with epithelial cell morphology.
[b]All cancer cell lines will form solid tumors in mice except HeLa cells.

EXAMPLE 7

Modification of CdtB/DNase I$^{mut5}$ to Improve Binding to CdtA

The genetically modified hybrid protein CdtB/DNase I$^{mut5}$ (see Table 1) had an increased specific activity, relative to CdtB and CdtB/DNase I (see FIG. 8), and formed a heterotrimer with wild-type CdtA and CdtC. However, this heterotrimer failed to inhibit the proliferation of cells or cause cell cycle arrest. As seen in the Cdt structure depicted in FIG. 7, two regions in CdtB appear to be in contact with CdtA (large loop; L261-S272 in FIG. 5) and CdtC (α-helix H1; N41-S54 in FIG. 5). The large loop is not present in CdtB/DNase I$^{mut5}$. The CdtB/DNase I hybrid protein does not inhibit cell proliferation (see FIG. 6A), yet appears to bind to the other subunits when CdtA is immobilized on thyroglobulin or subjected to differential dialysis (FIG. 6B). This result could be obtained if CdtB/DNase I$^{mut5}$ binds in the heterotrimer only to CdtC instead of to both CdtA and CdtC thus forming an aberrant heterotrimer. To entice the CdtB/DNase I hybrid to form a correctly assembled heterotoxin, the large loop region was added to the CdtB/DNase I$^{mut5}$ hybrid protein by genetically substituting the sequence LMLNQLRSQIT (SEQ ID NO: 58, positions 261-271) for NGLSDQLAQAI (SEQ ID NO: 59, positions 265-275).

A computer model of CdtB/DNase I$^{mut5}$ containing the restored large loop sequence shows an increased distance (32.48 Å) between this putative CdtA binding domain and the CdtC binding domain (α-helix H1) relative to that in CdtB (10.03 Å) (FIG. 10). It was hypothesized that this difference in conformation between CdtB and the hybrid protein may affect assembly of the heterotrimer. In a series of modeling exercises a proline residue was added at key theoretical folding regions in the CdtB/DNase I$^{mut5}$ structure. One theoretical substitution, Y174P (FIG. 5) reduced the estimated distance between the putative subunit binding domains to 15.38 Å. This proline was genetically added to the CdtB/DNase I$^{mut5}$ hybrid protein that contained the large loop modification.

The new mutated hybrid protein designated CdtB/DNase I$^{Y174P}$ (SEQ ID NO: 29, 28), containing both the large loop and Y174P substitutions, was used to make a heterotrimer with wild-type CdtA and CdtC. Like the previous variations of the CdtB/DNase I hybrid proteins, CdtB/DNase I$^{Y174P}$ bound to CdtA and CdtC as measured in the thyroglobulin ELISA (FIG. 11). The stoichiometric increase in binding suggested that a heterotrimer was formed. Unlike previous versions of the hybrid protein, the heterotrimer formed with CdtB/DNase I$^{Y174P}$ inhibited proliferation of CHO cells (FIG. 12). To confirm that the new mutated hybrid protein formed an active heterotoxin culture, HeLa cells and two of the oral squamous cell carcinoma lines were treated with the reconstituted heterotrimer preparation. All three cell lines treated with heterotoxin made with CdtB/DNase I$^{Y174P}$ exhibited a significant accumulation of cells having a 4n DNA content indicative of a $G_2$ block in cell cycle progression (Table 6). The portion of the cancer cell populations having a 4n DNA content ranged from 57-75 percent compared to 39 percent for HeLa cells. The accumulation of CdtB/DNase I$^{Y174P}$-treated cells at the $G_2$/M interphase of the cell cycle is shown, compared to controls, in FIG. 13.

TABLE 6

Cell cycle analysis of cancer cells treated with reconstituted mutant heterotoxin

| Cell line | Wild-type or mutant protein in heterotrimer | Diploid G1 (2n) (%) | Diploid G2 (4n) (%) | Diploid S (%) | Coefficient of variance (%) |
|---|---|---|---|---|---|
| HeLa | none | 71.54 | 5.97 | 22.49 | 4.60 |
|  | CdtB[a] | 25.42 | 32.79 | 41.80 | 4.50 |
|  | CdtB/DNase I$^{Y174P}$ | 30.06 | 38.75 | 31.19 | 4.47 |
| CCL-30 | none | 58.83 | 0.00 | 41.17 | 12.05 |
|  | CdtB[a] | 18.47 | 54.09 | 27.44 | 5.32 |
|  | CdtB/DNase I$^{Y174P}$ | 19.91 | 56.73 | 23.37 | 6.10 |
| CAL-27 | none | 75.38 | 2.63 | 21.99 | 4.68 |
|  | CdtB[a] | 12.37 | 78.85 | 8.79 | 3.23 |
|  | CdtB/DNase I$^{Y174P}$ | 11.51 | 74.58 | 13.92 | 3.07 |

[a]Wild-type recombinant protein from *E. coli* BL-21(DE3) (pJDB7).

EXAMPLE 8

Cell-Specific Targeting of a Microbial Genotoxin Results in Selective Inhibition of Cancer Stem Cells Materials and Methods Epithelial Cells. CAL-27, HeLa and AC133.1 (mouse B cell hybridoma; ATCC) were cultured in DMEM (Invitrogen). Caco-2, RPMI 2650 and FaDu were cultured in EMEM supplemented with 0.1 mM Non-Essential Amino Acids (Invitrogen-GIBCO). All cell lines were also supplemented with 10% FCS, except for Caco-2 (20% FCS), and 0.1% Anti-Anti Antibiotic Antimycotic (Invitrogen-GIBCO). Primary human gingival epithelial cells (HGEC) were isolated from gingival tissue removed as part of routine periodontal surgeries conducted in the University of Pennsylvania School of Dental Medicine Graduate-Periodontics Clinic. The protocol for tissue procurement received Institutional Review Board approval and all donors were required to provide informed consent. Epithelial cells were isolated as described previously. Since isolated cells typically reached senescence by the third passage experiments requiring primary HGEC were repeated using cells isolated from gingival provided by different subjects.

HGEC isolated from a single explant culture were grown to 70% confluence in F12 medium containing 10% FCS and were transfected with 2 μg of pSG5T DNA, containing the SV40 large T-antigen gene. Effective Transfection Reagent (QIAGEN) was added according to the manufacturer's instructions. Transfected cells were obtained by clonal dilution. Expression of the SV40 large T-antigen gene was confirmed by western blotting using an anti-S V40 large T- and small t-antigen-specific MAb (BD Pharmingen; 1:200).

Cultures of a single immunopositive clone survived up to 22 passages before reaching senescence. Intact cells were examined for the presence of Ep-OAM by immunofluorescence staining.

RNA Extraction and Real-Time PCR. Total mRNA was isolated from cells using the Trizol reagent (Invitrogen) following the manufacturer's recommendations. cDNA was prepared from 2 ug of total mRNA using oligo(dT) and the Superscript First-Strand Synthesis System for RT-PCR (Invitrogen). Real-time PCR reactions were preformed in an ABI 7300 Real-Time PCR System using Power SYBR Green PCR Master Mix (Applied Biosystems). The cDNA-specific primers designed using the Primer Express software (Applied Biosystems), were 5' GAGAAAGTGGCATCGTGCAA-3' (forward) and 5'-TGCCAAACCAAAACAAATTCAA-3' (reverse). TATA-binding protein (TBP) mRNA served as normalizing control. Forward and reverse primers were 5'-GGAGCTGTGATGTGAAGTTTCCTA-3' and 5'-CCAG-GAAATAACTCTGGCTCATAAC-3', respectively. A negative PCR control without template cDNA was included in each assay.

Western Blotting. CD133 was detected in whole cell lysates of the various SCC and primary HGEC by western blotting using a standard procedure. Lysates of Caco-2 and HeLa cells were used as positive and negative controls, respectively.

Site-Specific Mutagenesis. The CdtA residue C178 was replaced with alanine by site directed mutagenesis using the primer pair 5'-AAAGTGTGTCACAAGGACGT GCAGTCACTTATAATCCTGTAAGTCC-3' (forward) and 5'-GGACTTACAGGATTATAAGTGACT GCACGTCCTTGTGACACACTT-TT-3[1] (reverse). The underlined bases mark the alanine codon. Mutated DNA strands were made using PfuUltra DNA polymerase in PCR (Stratagene). Template DNA was obtained from pMUTc149cdtA which contained a mutation resulting in the amino acid substitution C149A in CdtA. The methylated parental DNA strands were digested with Dpn\ (New England Biolabs, Beverly, Mass.) prior to transformation of *Escherichia coli* TOP10 chemically competent cells (Invitrogen). The mutation was confirmed by DNA sequencing. Plasmid DNA having the confirmed sequence was isolated and transformed into *E. coli* BL-21(DE3) competent cells (Novagen) to express the mutated gene and for isolation of the gene product. The resulting double cysteine mutant was designated $CdtA^{c149A,C178A}$.

Protein Isolation and Toxin Reconstitution. Recombinant clones *E. coli* BL-21(DE3) (pJDA9), *E. coli* BL-21(DE3) (pJDB7) and *E. coli* BL-21(DE3) (pJDC2) were used to prepare the three wild-type CdtA-His6, CdtB-HiS6 and CdtC-His6 proteins, respectively, by affinity chromatography as described previously. All three proteins have His6 tags at the carboxy-terminal end. The same method was used to obtain the $CdtA^{c149A,C178A}$-His6 gene product. Protein purity was assessed as described previously.

Wild-type heterotoxin (CdtABC) and heterotoxin containing the unconjugated and MAb-conjugated $CdtA^{c149AtC178A}$-His6 protein were reconstituted in a refolding buffer as described previously. Heterotrimer formation was confirmed by a differential dialysis technique using a membrane with a molecular weight exclusion limit of 100 kDa (Spectrum Laboratories Inc.). Each reconstituted protein sample was examined before and after dialysis on a western blot.

Binding Assay. A previously characterized enzyme-linked immunosorbent assay for binding of Cdt subunits to cultured cells (CELISA) was used to examine binding kinetics of $CdtA^{c149A}\_{C178A}$-His6. 96-well microtiter plates were seeded with $1.5 \times 10^4$ RPMI 2650 or FaDu cells/well in growth medium and incubated for 48 h to allow the cells to attach and become confluent. The cells were fixed with buffered 10% formalin followed by the addition of increasing concentrations protein (0-2 μg of purified $CdtA^{c149A,c178A}\_{HiS6or}$ cdtA-$His_6$) and 2% bovine serum albumin (BSA). After incubation for 1 h at room temperature bound protein was fixed with a mixture of 2% formaldehyde and 2% glutaraldehyde and detected with an anti-His>>Tag monoclonal antibody (Novagen).

Immunochemistry. The IgG1 kappa fraction was purified from cultured AC133.1 mouse hybridoma cells using the Montage™ Antibody Purification PROSEP-A Kit (Millipore). Antibody concentration was determined using the Beer-Lambert Law [IgG (mg/ml)=A280×0.72] and a titer was obtained using a whole cell lysate of Caco-2 cells. The $CdtA^{c149A,c178A}$-His6-MAb conjugate was made using a modification of a procedure described previously. The chemical crosslinker 4-succinimidyloxycarbonyl-a-methyl-a-(2-pyridyldithio)toluene (SMPT; Pierce) was incubated with the purified IgG (1 mg SMPT/10 mg of IgG) overnight at 4° C. Excess SMPT was removed by dialysis. $CdtA^{c149A,c178A}\cdot_{His6}$ (0.5 mg) was added to the SMPT-MAb complex and the preparation incubated for 48 h at 4° C. Unconjugated excess SMTP-MAb was removed by passing the sample thorough a nickel-iminodiacetic acid column (Novagen). Unconjugated $CdtA^{c149A,C178A}$-His6 was removed by dialysis of the sample against 20 mM Tris-HCl (pH 7.9), 0.5 M NaCl and 5 mM imidazole. The final protein concentration was determined with the Micro BCA Protein Assay Kit (Pierce).

Cell Cycle Analysis. Cell cycle arrest was determined by flow cytometry as described previously. The various SCC cell lines, HGEC and Caco-2 cells were grown for 24 h and then incubated for an additional 36 h with 10 ug/ml of one of the following preparations: (i) reconstituted wild-type heterotoxin (CdtABC), (ii) heterotoxin made with MAb-conjugated mutated CdtA (CdtA$^{c149A,c178A}$BC-CD133MAb), (iii) heterotoxin made with unconjugated mutated CdtA (CdtA$^{c149A,C178A}$BC) or (iv) purified AC 133.1 MAb IgG (CD133MAb). Input protein concentration was based on dose response data obtained in published standardized assays. Untreated control cell cultures did not receive any additions. Propidium iodide stained nuclei were prepared from $1\times10^6$ cells from each culture as described previously. Stained nuclei were examined with a FACSCalibur four-color dual-laser flow cytometer (BD Biosciences) at the Abramson Cancer Center Flow Cytometry and Cell Sorting Resource Laboratory at University of Pennsylvania. The data from 30,000 events were analyzed with ModFit LT 3.2 (Verity Software House).

In a separate set of experiments, cultures of the RPMI 2650 cell line were incubated for 36 h with increasing concentrations (0-32 µg/ml) of CdtA$^{c149A,c178A}$BC-CD133MAb.

Propidium iodide stained nuclei were prepared and examined by flow cytometry as described above to determine a dose response.

Immunofluorescence Staining. Immunofluorescence microscopy was performed as described previously with minor modifications. Cells ($1\times10^4$ cells per well) were cultured in eight-well chamber slides for 48 h. Slides used for staining of CAL-27 were coated with poly-L-lysine to promote cell attachment. Cells were fixed with 4% buffered formalin, blocked with 1% BSA and stained with mouse anti-human CD133/1 MAb (AC133, Miltenyi Biotec; 1:200) and Alexa Fluor 488 goat anti-mouse IgG conjugate (Invitrogen/Molecular Probes®; 1:400). Cell nuclei were stained with DAPI. Slides were mounted using Prolong Anti-Fade (Promega Corporation) and viewed with a Nikon Eclipse 80i fluorescence microscope. Digital images were recorded with Spot Advanced 4.6 software (Diagnostic Instruments, Inc.).

For flow cytometry, $1\times10^6$ cells, preblocked with 1% BSA, were incubated with either: (i) no antibody (unstained), (ii) an Alexa Fluor 488 goat anti-mouse IgG conjugate (Invitrogen) (Isotype FITC stained), (iii) purified AC133.1 MAb IgG followed by the Alexa Fluor 488 conjugate (CD 133MAb stained) or (iv) mouse anti-human CD133/1 MAb conjugated to PE. The data from 50,000 events were analyzed with FlowJo 8.8.6 (Tree Star, Inc.).

Computer Modeling. The crystal structure of the *A. actinomycetemcomitans* Y4 Cdt (38) was modeled with UCSF Chimera 1.3 (http://www.cgl.ucsf.edu/chimera/) using Protein Data Bank accession number 2F2F coordinates. Disulfide bonds were predicted using the genomic disulfide analysis program (GDAP; 40; http://www.doe-mbi.ucla.edu/~boconnor/GDAP/1)

Statistical Analyses. Experiments were performed a minimum of three times on different days unless otherwise noted. Data are presented as the mean values±SD. Standard deviations were for data sets obtained from independent experiments. The Paired Student's f-test was used to compare differences in data exhibiting normal distributions. P values <0.05 were considered significant.

Results

Susceptibility of Primary HGEC and SCC Cell Lines to the Cdt. HGEC were isolated from gingival tissue and immortalized with SV40. These cells had a characteristic epithelial morphology, were judged to be free of fibroblasts by microscopic evaluation and contained the characteristic epithelial cell adhesion molecule (Ep-CAM; 13). Treatment of primary (FIG. 15, first column) and. Immortalized. HGEC, in culture, with reconstituted recombinant *A. actinomycetemcomitans* Cdt (CdtABC) resulted in growth arrest at the G2/M interphase of the cell cycle. There was an approximate 50% increase in the number of cells with a 4n DNA content following exposure to 10 µg/ml of the toxin for 36 h. When head and neck SCC cell lines CAL-27 (tongue), RPMI 2650 (nasal septum) and FaDu (pharynx) were exposed to the Cdt in culture, under the same conditions they arrested at the G2/M interphase. From 47 to 61% of each of the SCC cell populations had a 4n DNA content following exposure to the toxin as shown for CAL-27 (FIG. 15, middle column). These results were similar to those obtained with a HeLa cell (adenocarcinoma of the cervix) control (FIG. 15, last column).

Gene Expression and Cell Surface Display of CD133. Real-time (RT)-PCR showed that the RPMI 2650 cells expressed the prominin-1 gene at a level comparable to that of the colorectal adenocarcinoma Caco-2 positive control (FIG. 16A). The prominin-1 gene was also expressed by CAL-27 cells but at a level that was orders of magnitude, lower than that in RPMI 2650. Expression of the prominin-1 gene was not detected in primary HGEC A prominin-1 sequence was amplified from FaDu cDNA. However, the amount of amplicon made was not statistically significant.

CD133 was observed in cell lysates of RPMI 2650 and Caco-2, on western blots, using a CD133/1 (AC.133) mouse anti-human MAb (FIG. 16B) as well as MAb IgG purified in our laboratory from hybridoma (AC133.1) culture medium. CD133 was not detected in cell lysates of HGEC, FaDu or Cal-27 cells. These results were in excellent agreement with those of the RT-PCR analysis.

To assess the distribution of CD133$^+$ cells that displayed the antigen on the cell surface in culture, immunolabeled SCC cell lines were examined by fluorescence microscopy. CD133$^+$ cells detected with CD 133/1 (AC 133) mouse anti-human MAb were observed only in cultures of the RPMI 2650 cell line (FIG. 17A). There was no detectable staining of CAL-27 cells which correlated with the expression data obtained by RT-PCR. Presentation of the CD133 antigen on the surface of RPMI 2650 cells was confirmed by flow cytometry (FIG. 17B). RPMI 2650 was the only SCC cell line that exhibited a significant increase in fluorescence intensity when evaluated with the mouse anti-human CD 133 MAb IgG (AC 133.1) and a fluorescene-conjugated goat anti-mouse IgG reagent. This is indicated by the rightward shift of the red peak relative to the positions of the blue and green peaks representing unstained cells and cells treated with the fluorescene-conjugated second antibody (isotype FITC) alone, respectively. The positively stained RPMI 2650 cells exhibited a median fluorescence (MF) of 57.5. The Caco-2 positive control cells, FaDu cells and HGEC had MF values of 65.0, 5.1 and 12.7, respectively. Similar results were obtained when the RPMI 2650 cells were stained using a mouse anti-human CD 133 MAb conjugated to R-phycoerythrin (PE) (see inset; MF=64.8). Taken together the results of the four CD 133 assays established that the protein is a cell surface marker unique to certain SCC cell lines. Our findings are consistent with reports that subpopulations of tumor cell cultures contain CD133+ cells.

Targeting the Cdt to CD133$^+$ Cells. It is well established that the CdtA subunit binds the heterotrimer to host cells via a surface exposed receptor. The objective was to inhibit the formation of two predicted intrachain disulfides (C136/C149; C178/C197) in CdtA and to eliminate one of two surface exposed cysteines (FIG. 18A). Therefore, residues C149 and C178 were replaced with alanines. As shown in a CELISA, the double cysteine mutant, CdtA$^{c149A}$, c178A lost the ability to bind to RPMI 2650 and FaDu cells (FIG. 18B). The difference in cell binding, relative to that of the wild-type CdtA, was statistically significant and occurred over input protein concentrations of >250 ng per well.

Differential dialysis showed that the mutated CdtA subunit formed a heterotrimer with wild-type CdtB and CdtC (FIG. 18C). Following dialysis all three Cdt subunits were recovered from the dialysis tubing containing the sample reconstituted with CdtA$^{c149A,C178A}$. Heterotrimers, but not monomers and dimers, are retained by dialysis tubing having a molecular weight exclusion limit of 100 kDa. The disulfide coupling agent SMPT was conjugated through an amide linkage to the IgG isolated from the mouse B cell hybridoma AC 133.1. This conjugate was then coupled to CdtA$^{c149A,C178A}$ through a disulfide linkage using the remaining surface exposed C197.

Targeted Inhibition of SCC Cells. The CdtA$^{c149A,c178A}$-MAb conjugate was combined with wild-type CdtB and CdtC in refolding buffer to reconstitute active heterotoxin. The various SCC and Caco-2 cell lines as well as primary and immortalized HGEC were treated in culture with this reconstituted toxin. The cells were analyzed by flow cytometry after 36 h of exposure to CdtA$^{c149A,c178A}$BC-CD133MAb (FIG. 5). Among the tumor cell lines, only Caco-2 and RPMI 2650 cells underwent arrest at the G2/M interphase of the cell cycle. On average, 19 and 15% of these cells populations ($3.5 \times 10^6$ cells), respectively, had a 4n DNA content after exposure to 10 µg/ml of toxin protein. Control cultures treated with either the mouse anti-human CD 133 IgG MAb (AC133.1) alone or CdtA$^{c149A,C178A}$BC (reconstituted toxin containing the unconjugated mutated CdtA) were not arrested at G2/M. Primary and immortalized HGEC were not affected by CdtA$^{c149A,c178A}$BC-CD133MAb even though greater than 90% of these cells arrested at G2/M when treated with the wild-type Cdt.

The RPMI 2650 cell line responded in a dose dependent fashion to treatment with CdtA$^{c149A,c178A}$BC-CD133MAb (FIG. 19, last panel). Response to this toxin was linear over the range of 0 to 16 µg/ml of protein (R-squared=0.99). Maximum inhibition was obtained with approximately 16 µg/ml of protein. Higher concentrations of toxin showed saturation kinetics indicating that cell cycle arrest was specific. A portion (18%) of the total cell population had a 4n DNA content following exposure to the MAb-conjugated toxin. This response was about half the number of cells that were arrested after exposure to the wild-type Cdt.

Intoxication experiments were routinely performed using cell cultures that were 80-90% confluent. We found that younger cultures were more sensitive to both CdtABC and CdtA$^{c149A,c178A}$BC-CD133MAb. When replicate 50% confluent cultures of RPMI2650 cells were untreated and treated with 12 µg/ml of CdtABC or CdtA$^{c149A,c178A}$BC-CD133MAb, 8.5±0.7, 54.0±1.6 (P=0.001) and 26.4±0.6% (P=0.002) of cells, respectively, had a 4n DNA content. These results are indicative of increased accessibility of cells to the toxin.

Human epithelial cells and keratinocytes including HeLa, HEp-2, Caco-2, Vero, HaCat and Henle-407 are arrested at the G₂/M transition of the cell cycle when exposed to the Cdt from various bacterial genera. We found that the GMSM-K cell line was arrested at the S phase of the cell cycle when treated with recombinant *A. actinomycetemcomitans* Cdt. Those studies provided compelling evidence that epithelial cells may be in vivo targets of the toxin. The susceptibility of primary human epithelial cells to the Cdt had not been examined previously. In this study we showed that the toxin induced human gingival epithelial cells to arrest at the G2/M interphase. A similar result was obtained with three established head and neck SCC lines. Obtaining these data was an important first step in demonstrating that one can engineer the genotoxin to selectively inhibit the proliferation of specific types or subpopulations of cancerous epithelial cells.

The advantages of our method are twofold. First, the MAb was conjugated to the cell binding subunit (CdtA) of the heterotrimer rather than to the cytotoxic subunit (CdtB) leaving the active subunit of the toxin is unaltered. Second, application of the targeting strategy is unlimited since MAbs for other yet to be identified unique cancer cell surface markers can readily be conjugated to the surface exposed cysteine residue in CdtA$^{c149A,c178A}$ to tightly control target cell specificity. Our study serves as a "proof-of-concept" that the cellular tropism of the Cdt can be selectively altered and used to inhibit CSC in heterogeneous populations based on the expression of a unique cell surface antigen. Our findings show that the molecule can be useful in a specific antibody-based targeting of CSC that potentially outlines new prospects for more effective cancer treatments. Coupling of an anti-human CD 133 antibody with an agent capable of inducing cell death via a genotoxic mechanism may complement current cancer therapies by eliminating CSC responsible for tumor recurrence.

EXAMPLE 9

Oral Candidasis Therapeutics Using a Microbial Genotoxin

Oral candidiasis has an exceptionally widespread effect on health since it is the most common fungal infection in human populations. In the general population the disease is found more frequently in infants and older individuals (denture wearers) and is prevalent in immunocompromised patients that are undergoing cancer treatments, transplant procedures or are afflicted with HIV/AIDS.

Sufferers of oral candidiasis, which can include members of neonatal, pediatric, geriatric and immunosuppressed populations, are cared for by pediatric, geriatric and oral medicine dental practitioners. It is unknown, at this time if the cost of such treatment would be covered by medical insurance. Antifungal agents, primarily nystatin and triazoles such as fluconazole, are currently used for treatment. Accordingly, there exists a need for improved pharmaceutical compositions.

In one embodiment, the invention relates to a genetically and immunochemically modified bacterial-produced cytotoxin. The cytolethal distending toxin (Cdt) from the periodontal pathogen *Aggregatibacter actinomycetemcomitans* is a heterotrimer composed of CdtA, CdtB and CdtC subunits. The active subunit, CdtB, displays a type I deoxyribonuclease-like activity. While the primary function of CdtC is not clear, we have shown that the CdtA subunit recognizes a specific receptor on the surface of the target cell and that specific amino acids in an aromatic amino acid motif are required for binding. The CdtA subunit can be genetically engineered, without disrupting holotoxin assembly, to target the toxin specifically to pathogenic strains of *Candida albicans* that are the etiological agents of oral candidiasis. Additionally, the invention relates to a construct having a *Candida*-specific Cdt that can be used in a topical formulation to inhibit the pathogen and to alleviate the clinical symptoms such as pain, dysgeusia and dysphagia. The product can be designed to specifically target and inhibit the human fungal pathogen *C. albicans*. The product can be used in a topical formulation to treat oral candidiasis. The product may also be useful for the treatment of other forms of mucosal candidiasis, such as vaginal infections, that are amenable to topical application. The primary advantages of this potential agent, over common antifungals, will be a high degree of selective toxicity (a single species of yeast) and reduced likelihood of the development of resistant pathogenic *C. albicans* strains. There is an increasingly rapid dissemination of resistances to routinely used antifungal agents such as fluconazole.

Follow-on products can also be developed since any monoclonal antibody can be attached to the genetically-modified CdtA protein. Furthermore, the invention relates to a product which is an anti-cancer agent that targets the Prominin-1 antigen that has been found on the surface of some progenitor cancer cells.

It is a unique approach to adapt the Cdt to target a eukaryotic pathogen instead of primary mammalian cells. Many types of mammalian eukaryotic cells, such as epithelial cells, lymphocytes and macrophages appear to be the natural targets of the cytotoxin. However, there is evidence from published studies that yeast cells are sensitive to the DNA-damaging effect of the Cdt. The stringent connection between DNA damage and cell cycle arrest is an essential safety feature in eukaryotic cells that prevents cells with damaged DNA or chromatin from initiating cell division. The cells cannot readily enhance the DNA repair pathway or circumvent this checkpoint process by spontaneous mutation. Therefore, *Candida* can not be able to easily develop resistance to the cytotoxin. It is also a unique strategy to use the cell binding subunit of an A-B type heterotoxin to make the cytotoxin cell-specific. The main advantage of this approach is that the biologically active component of the heterotoxin (CdtB subunit) remains unaltered.

*Candida albicans*-specific monoclonal antibodies can also be required to create the final product. Several *C. albicans* monoclonal antibodies are commercially available (Millipore and Abeam). In addition, monoclonal antibodies that recognize antigens displayed on the surface of yeast cells are relatively easy to make and isolate. There are a number of companies that specialize in monoclonal antibody production.

We have constructed mutants of CdtA that no longer bind to mammalian epithelial cells and have a single molecular surface exposed cysteine for conjugation of the monoclonal antibodies. These mutated CdtA proteins form a heterotrimer complex, albeit inactive, with wild-type CdtB and CdtC. Our data shows that a binding-deficient CdtA-anti-Prominin-1 conjugate recognizes Prominin-1 expressing cell lines such as CaCo-2 as well as CAL-27, isolated from an oral squamous cell carcinoma.

Characterization of some of the binding-deficient and cysteine substitution mutants of CdtA has been published in: Cao, L., A. Volgina, C. M. Huang, J. Korostoff, and J. M. DiRienzo. 2005. *Mol Microbiol* 58:1303-1321 and Cao, L., A. Volgina, J. Korostoff, and J. M. DiRienzo. 2006. *Infect Immun* 74:4990-5002.

The key developmental steps in the process are: (1) To "knock out" the Cdt receptor-binding domain in CdtA. (2) To mutate several trivial cysteine residues in CdtA to prevent possible intrachain disulfide formation. (3) To conjugate a linker-modified *Candida* monoclonal antibody to the mutated CdtA via the remaining molecular surface-exposed cysteine. (4) To reconstitute and test heterotoxin using the mutated CdtA-*Candida* monoclonal antibody conjugated protein, wild-type CdtB and wild-type CdtC to confirm that this modified Cdt inhibits cells. (5) To demonstrate that the *Candida*-specific Cdt reduces numbers of *Candida* and alleviates the pathology associated with oral candidiasis in a rat model.

A battery of assays, previously published by us, can be used to test the effects of the modified heterotoxin on the growth of *C. albicans* in culture. An immortalized rat gingival epithelial cell line can also be used as a control to establish that the modified heterotoxin no longer inhibits the proliferation of epithelial cells.

Sprague-Dawley rats can be infected with *C. albicans*, using a well-characterized and published oral candidiasis rat model (Allen, C. M. 1994. *Oral Surg Oral Med Oral Pathol* 78:216-221 and Samaranayake, Y. H., and L. P. Samaranayake. 2001. *Clin Microbiol Rev* 14:398-429), and will test the efficacy of the modified heterotoxin in vivo. At the end point of the experiments, tissue from euthanized rats can be processed to obtain colony forming units of the yeast and stained to assess histological changes.

EXAMPLE 11

Cytolethal Distending Toxin Induces Cell Damage in Gingival Explants

The cytolethal distending toxin (Cdt), expressed by the periodontal pathogen *Aggregatibacter actinomycetemcomitans*, inhibits the proliferation of sensitive cells by arresting the cell cycle at the $G_2/M$ interphase. This bacterium colonizes the subgingival microenvironment in close proximity to sulcular and junctional epithelial cells. The gingival epithelium is the first line of defense against periodontal pathogens and, when damaged, allows bacteria to collectively gain entry into underlying connective tissue where the Cdt and other microbial products can affect infiltrating inflammatory cells leading to the destruction of the attachment apparatus. Histological evaluation of healthy human gingival tissue, exposed to the Cdt for 18 hours ex vivo, revealed more rapid detachment of the keratinized epithelial cell layer, disruption of rete pegs, dissolution of tight-junctions and distension of spinous and basal epithelial cells. Primary gingival epithelial cells, but not gingival fibroblasts, isolated from the same healthy tissue were cell cycle arrested when treated with the toxin and examined by flow cytometry. Our results: (i) show that the Cdt can make a significant contribution to tissue destruction characteristic of the early stages of periodontal disease and (ii) demonstrate that a gingival explant model can be used to further assess the virulence potential of this toxin.

Inventors of the instant application show that the epithelial layers in gingival explants obtained from periodontally healthy gingiva exhibit detachment of the keratinized epithelial cell layer, disruption of rete pegs, dissolution of tight-junctions and distension of spinous and basal epithelial cells when exposed to the Cdt. These data support the development of an ex vivo tissue model for assessing the effects of the Cdt on gingival epithelial cells in situ. Establishing that the Cdt of *A. actinomycetemcomitans* affects the integrity of the periodontium justifies targeting this toxin in therapeutic modalities designed to reduce the severity of periodontal diseases.

Materials and Methods

Gingival Tissue and Primary Cells

Gingival tissue was collected during routine periodontal surgeries conducted on healthy adults in the University of Pennsylvania School of Dental Medicine Graduate Periodontics Clinic. The protocol for tissue procurement received Institutional Review Board approval and all donors provided informed consent. In some experiments epithelial cells (HGEC) and fibroblasts (HGF) were isolated from tissue samples as described previously (Oda and Watson, 1990; Kanno et al., 2005). Cultures of HGEC and HGF were grown in serum-free keratinocyte medium and DMEM medium containing 10% FCS, respectively.

Protein Isolation and Toxin Reconstitution

Recombinant Cdt proteins were isolated by affinity chromatography as described previously (Cao et al., 2005). Heterotrimers were reconstituted, in a refolding buffer, from wild-type subunits (Mao and DiRienzo, 2002) or CdtB$^{H160A}$.

Histology and Immunostaining

Gingival tissue was immediately placed in F12 medium, supplemented with 5% fetal bovine serum and 1% Antibiotic-Antimycotic (Invitrogen, Carlsbad, Calif.). The tissue was cut into 5 mm pieces and treated, in separate experiments, with varying concentrations of reconstituted Cdt ranging from 0 to 10 µg/ml. The toxin-treated samples were incubated at 37° C., in an atmosphere containing 10% $CO_2$, for varying periods of time, ranging from 0 to 36 h. Samples were then fixed in 4% buffered formalin and processed for paraffin sections by the Tissue Processing Service at the School of Dental Medicine. Sections from each explant were routinely stained with hematoxylin and eosin. In some experiments additional sections were stained with pan-keratin Ab3 mouse monoclonal antibody (1:200; Lab Vision Products, Fremont, Calif.) and rabbit anti-CdtB polyclonal antibody (1:50,000; Cao et al., 2008) followed by goat anti-mouse Alexa Fluor 488 and goat anti-rabbit IgG Alexa Fluor 594 conjugate (1:400; Invitrogen). Cell nuclei were visualized with DAPI. The stained sections were viewed with a Nikon Eclipse 80i fluorescence microscope. Digital images were recorded with Spot Advanced 4.6 software (Diagnostic Instruments, Inc., Sterling Heights, Mich.). Experiments were performed a minimum of three times using tissue obtained from different patients.

Isolated primary cells were grown on 8-well chamber slides and incubated with either 1:100 dilution of mouse anti-human Ep-Cam (EBA-1) antibody (Santa Cruz Biotechnology, Santa Cruz, Calif.) or 1:500 dilution of anti-fibroblast CD90/Thy-1 antigen (Ab-1) antibody (Oncogene Research Products, La Jolla, Calif.), followed by Alexa Fluor 488 goat anti-mouse IgG conjugate (1:400 dilution; Invitrogen) to assay for expression of the epithelial cell adhesion molecule (Ep-CAM) and CD90/Thy-1 antigen, respectively. Cell nuclei were stained with DAPI. The stained cells were viewed with a laser scanning confocal microscope BioRad Radiance 2100 (BioRad Laboratories, Hercules, Calif.).

Cell Cycle Analysis

Cell cultures were untreated or treated with 10 µg/ml of wild-type toxin (CdtABC) or toxin reconstituted with CdtB$^{H160A}$ for 36 hours as described previously (Cao et al., 2005). Cell cycle arrest was determined by flow cytometry. Propidium iodide stained nuclei were examined on a FACS-Calibur four-color dual-laser flow cytometer (BD Biosciences) at the Abramson Cancer Center Flow Cytometry and Cell Sorting Resource Laboratory of the University of Pennsylvania. Data from 30,000 events were analyzed with ModFit LT 3.2 (Verity Software House, NH).

Results

Stability of Gingival Tissue Explants

The general morphology of explants, maintained in tissue culture medium for up to 24 h, was examined to establish that gingival tissue removed during periodontal surgery could be used to assess the effects of the Cdt on the integrity of epithelial cells in situ. The gingival epithelial layers (GE), rete pegs (RP) and connective tissue (CT) were intact in hematoxylin-eosin stained sections from freshly excised tissue (FIG. 20A). The appearance of the epithelial cells and tight-junctions, detected by staining for pan-keratin expression, was normal. The only clearly evident change in appearance of the tissue was some mechanical separation of the keratinized surface layer by 18 h of incubation (FIG. 20B). No further deterioration of the tissue was observed by 24 h (FIG. 20C).

Effects of the Cdt on Gingival Tissue

Previous studies showed that a histidine in the catalytic site of the CdtB subunit is essential for the cell cycle arrest activity of the Cdt (Elwell et al., 2001). Although our mutant CdtB$^{H160A}$ binds to wild-type CdtA and CdtC, the reconstituted heterotrimer fails to inhibit the proliferation of cells. No histological changes were observed in gingival tissue when treated, for up to 36 h, with 10 µg/ml of reconstituted toxin containing the mutated CdtB subunit (CdtAB$^{H160A}$C) (FIG. 21A-C). The appearance of tissue treated with CdtAB$^{H160A}$C was identical to that observed with the untreated specimen (FIG. 21D). Tissue exposed to 10 mg/ml of wild-type toxin (CdtABC) for 18 h exhibited significant histologic alterations. There was more pronounced peeling of the keratinized surface layer, extensive disruption of the epithelial layers and marked the loss of structural integrity of the rete pegs (FIG. 21E). In general, the epithelial layers appeared to be swollen and stained less intensely by hematoxylin-eosin. The epithelial cells were dramatically distended with an apparent loss of the tight-junctions (compare insets in FIGS. 21D and 21E). Tissue treated for 36 h with 5 µg/ml of Cdt exhibited the same effects (FIG. 20F). The results of dose response experiments indicated that tissue treated with as little as 2.5 µg/ml of Cdt for 24 h had less pronounced, but clearly detectable, morphological changes.

Co-Localization of the Cdt and Epithelial Cells

Epithelial cells in Cdt-treated tissue were localized by staining sections with anti-pan-keratin. When the same sections were co-stained with CdtB antibodies, the subunit was observed primarily in the epithelial layers (red fluorescence in FIG. 22A). Significantly less CdtB was detected on the keratinized outer surface layer of the gingival epithelium as well as in the underlying connective tissue. Similar results were obtained when the tissue was treated with CdtAB$^{H160A}$C (FIG. 22B). However, in this case no change in tissue morphology was observed as noted by the appearance of more well delineated rete pegs. CdtB was not detected in untreated control tissue (FIG. 22C).

Effect of the Cdt on Primary Gingival Epithelial Cells and Fibroblasts

To further support the observations that the Cdt was primarily affecting the epithelial and not connective tissue layers, we isolated primary HGEC and HGF from the same type of tissue as that used for the ex vivo experiments. The cultured primary HGEC had an epithelioid morphology, stained positive with a fluorescent-tagged Ep-CAM antibody and negative with an antibody that recognizes CD90/Thy-1 (FIG. 23A). The cultured HGF exhibited a morphology typical of fibroblasts and bound the CD90/Thy-1 (Ab-1) antibody. We previously showed that the Ab-1 marker is expressed in oral fibroblasts but not epithelial cells (Kang et al., 2005).

HGEC exposed to the Cdt were arrested at the $G_2$/M interphase of the cell cycle as indicated by a significant increase in the number of cells with a 4n DNA content (FIG. 23B). CdtAB$^{H160A}$C had no effect on the cell cycle. In contrast, there was no increase in the number of cells having a 4n DNA content when the HGF were treated with the Cdt.

When we co-incubated healthy gingival tissue with reconstituted recombinant Cdt severe histological changes were observed by 18 hours of exposure. The effects were observed well within the 48 hour window of tissue health. The swelling or distension of cells in the spinous and basal layers of the tissue was a clear indication of Cdt activity. The fact that the tissue was unaffected when exposed to toxin reconstituted with the biologically inactive CdtB$^{H160A}$ subunit for up to 36 hours, localization of CdtB in the epithelial layers and cell cycle arrest of Cdt-treated primary HGEC, supplied additional supporting evidence that the observed tissue damage was directly related to the toxin. There were no observed effects of the Cdt on cells in the connective tissue layer. This observation was supported by the data showing that very little CdtB was present in the connective tissue and that primary HGF were not affected by the Cdt.

In conclusion, gingival tissue exposed, in vitro, to the Cdt exhibited severe structural damage. The histologic changes were predominantly confined to the epithelial layers of the tissue making a strong case for the role of the Cdt in the breakdown of the protective epithelial barrier considered to be an early step in the initiation of periodontal disease. The gingival explant model has significant potential for studying the details of select interactions of the Cdt with gingival epithelial cells in situ.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A recombinant polypeptide comprising a chimera, wherein said chimera comprises a DNase I fragment or a homologue thereof and a cytolethal distending toxin (Cdt) fragment or a homologue thereof, wherein said Cdt fragment is a CdtB fragment, and wherein said DNase I fragment comprises the amino acid sequence set forth in SEQ ID NO.: 12, 14, or 16 and said CdtB fragment comprises the amino acid sequence set forth in SEQ ID NO.: 4, 5, 6, or 7.

2. The recombinant polypeptide of claim 1, wherein said CdtB fragment comprises a mutation.

3. The recombinant polypeptide of claim 2, wherein said mutation is G55R, L62E, S99Y, R100E, V134R, Y174P or their combination.

4. The recombinant polypeptide of claim 2, wherein said DNase I fragment comprises a substitution of SEQ ID NO: 58 for SEQ ID NO: 59.

5. The recombinant polypeptide of claim 1, wherein said chimera is $His_6$-tagged.

6. The recombinant polypeptide of claim 1, wherein said chimera comprises (a) said CdtB fragment in the amino terminus of said chimera and said DNase I fragment in the carboxy terminus of said chimera or (b) a homologue of a DNase I fragment in the carboxy terminus of said chimera and a Cdt fragment in the amino terminus of said chimera or (c) a DNase I in the carboxy terminus of said chimera and a homologue of a Cdt fragment in the amino terminus of said chimera or (d) a homologue of a DNase I fragment in the carboxy terminus of said chimera and a homologue of a Cdt fragment in the amino terminus of said chimera.

7. The recombinant polypeptide of claim 1, wherein said recombinant polypeptide binds both CdtA and CdtC.

8. The recombinant polypeptide of claim 1, wherein said recombinant polypeptide inhibits proliferation of a neoplastic cell.

9. The recombinant polypeptide of claim 1, wherein said recombinant polypeptide inhibits proliferation of a neoplastic cell and binds both CdtA and CdtC.

10. A method for inhibiting the proliferation of a neoplastic cell comprising the step of contacting said cell with a recombinant polypeptide according to claim 1 or a nucleic acid molecule encoding the same, thereby inhibiting the proliferation of a neoplastic cell.

11. A recombinant polypeptide comprising a chimera, wherein said chimera comprises a DNase I fragment or a homologue thereof and a cytolethal distending toxin (Cdt) fragment or a homologue thereof, wherein the amino acid sequence of said chimera is selected from the group consisting of amino acid sequences as set forth in SEQ ID NOs: 24-27 and SEQ ID NO: 29.

12. The recombinant polypeptide of claim 11, wherein the amino acid sequence of said recombinant polypeptide is as set forth in SEQ ID NO: 29.

13. A method for inhibiting the proliferation of an oral squamous cell carcinoma cell comprising the step of contacting said cell with a recombinant polypeptide according to claim 11 or a nucleic acid molecule encoding the same, thereby inhibiting the proliferation of said cell.

* * * * *

UNITED STATES PATENT AND TRADEMARK OFFICE
CERTIFICATE OF CORRECTION

| | | |
|---|---|---|
| PATENT NO. | : 8,920,809 B2 | Page 1 of 1 |
| APPLICATION NO. | : 12/858312 | |
| DATED | : December 30, 2014 | |
| INVENTOR(S) | : Joseph M. Dirienzo | |

It is certified that error appears in the above-identified patent and that said Letters Patent is hereby corrected as shown below:

In the Specification

In column 1, line 13, the following paragraph should be inserted:

-- GOVERNMENT INTEREST STATEMENT

This invention was made with government support under grant no. R21 DE017679 awarded by the National Institute of Health. The government has certain rights in the invention. --

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,920,809 B2 | Page 1 of 1 |
| APPLICATION NO. | : 12/858312 | |
| DATED | : December 30, 2014 | |
| INVENTOR(S) | : Joseph M. Dirienzo | |

It is certified that error appears in the above-identified patent and that said Letters Patent is hereby corrected as shown below:

In the Claims

In column 133, line 62 of Claim 1, delete "DNase I" and replace with --CdtB--.

In column 133, line 64 of Claim 1, delete "CdtB" and replace with --DNase I--.

Signed and Sealed this
Seventh Day of June, 2016

Michelle K. Lee
*Director of the United States Patent and Trademark Office*